US010583186B2

(12) United States Patent
Vedantam et al.

(10) Patent No.: US 10,583,186 B2
(45) Date of Patent: Mar. 10, 2020

(54) COMPOSITIONS COMPRISING RECOMBINANT PROBIOTIC BACTERIA AND METHODS OF USE THEREOF

(71) Applicants: ARIZONA BOARD OF REGENTS ON BEHALF OF THE UNIVERSITY OF ARIZONA, Tucson, AZ (US); THE UNITED STATES OF AMERICA AS REPRESENTED BY THE DEPARTMENT OF VETERANS AFFAIRS, Washington, DC (US)

(72) Inventors: Gayatri Vedantam, Tucson, AZ (US); Virinchipuram K. Viswanathan, Tucson, AZ (US); Michael Mallozzi, Tucson, AZ (US)

(73) Assignees: ARIZONA BOARD OF REGENTS ON BEHALF OF THE UNIVERSITY OF ARIZONA, Tucson, AZ (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 15/545,462

(22) PCT Filed: Jan. 22, 2016

(86) PCT No.: PCT/US2016/014590
§ 371 (c)(1),
(2) Date: Jul. 21, 2017

(87) PCT Pub. No.: WO2016/118900
PCT Pub. Date: Jul. 28, 2016

(65) Prior Publication Data

US 2018/0000919 A1 Jan. 4, 2018

Related U.S. Application Data

(60) Provisional application No. 62/107,224, filed on Jan. 23, 2015.

(51) Int. Cl.

| | |
|---|---|
| ***A61K 39/08*** | (2006.01) |
| ***A61K 35/747*** | (2015.01) |
| *A61K 39/00* | (2006.01) |

(52) U.S. Cl.
CPC ............ *A61K 39/08* (2013.01); *A61K 35/747* (2013.01); *A61K 2039/523* (2013.01)

(58) Field of Classification Search
None
See application file for complete search history.

(56) References Cited

U.S. PATENT DOCUMENTS

2005/0233408 A1 10/2005 Pouwels et al.

FOREIGN PATENT DOCUMENTS

WO WO-9632486 A1 * 10/1996 ........... C07K 14/005

OTHER PUBLICATIONS

Uniprot Accession #Q9AEM4 Jun. 1, 2001.*
Infect. Immun. 69:3442-3446 (2001).*
International Search Report and Written Opinion for PCT International Application No. PCT/US2016/014590 dated May 19, 2016.
UniProt Accession No. Q1JU94, S-layer protein Jun. 13, 2006 [Retrieved on May 3, 2016] Retrieved from the internet <http://www.uniprot.org/uniprot/Q1JU94>.
NCBI Accession No. CAJ69681, Feb. 6, 2015.
NCBI Accession No. WP_011254065, May 15, 2013.
Duong, et al., "Construction of vectors for inducible and constitutive gene expression in Lactobacillus", Microb Biotechnol. 4(3), 2011, 357-367.
Ferreira, et al., "Immunization of mice with Lactobacillus casei expressing intimin fragments produces antibodies able to inhibit the adhesion of enteropathogenic *Escherichia coli* to cultivated epithelial cells", FEMS Immunol Med Microbiol. 54(2), 2008, 245-254.
Gaspar, et al., "Engineering Lactococcus lactis for production of mannitol: high yields from food-grade strains deficient in lactate dehydrogenase and the mannitol transport system", Appl Environ Microbiol. 70(3), 2004, 1466-1474.
Leenhouts, et al., "Campbell-like integration of heterologous plasmid DNA into the chromosome of *Lactococcus lactis* subsp. *lactis*", Appl Environ Microbiol. 55(2), 1989, 394-400.
Merrigan, et al., "Surface-layer protein A (SlpA) is a major contributor to host-cell adherence of Clostridium difficile", PLoS One. 8(11), 2013, e78404.

* cited by examiner

*Primary Examiner* — Oluwatosin A Ogunbiyi
(74) *Attorney, Agent, or Firm* — Casimir Jones, S.C.; Robert A. Goetz

(57) ABSTRACT

The invention features probiotic bacteria expressing *Clostridium difficile* SlpA, or fragment thereof, and its use for the treatment or prevention of *Clostridium difficile* infection and gut colonization.

12 Claims, 26 Drawing Sheets

Specification includes a Sequence Listing.

FIG. 1C

★ 1338 BP codon-optimized synthesized slpA chimera fragment

GGATCCATGAAGAAAAATTTAAGAATCGTTAGCGCTGCTGCTGCTGCTTTACTTGCTGTTGCTCCA
GTTGCTGCTTCTGCTGTATCTACTGTTAGCGCTGCTGCACCTGTATTTGCTGCAACCACTGGTACAC
AAGGCTATACGGTGGTTAAGAATGATTGGAAAAAGGCTGTCAAACAATTACAAGATGGACTTAAA
GATAATAGTATTGGTAAGATTACGGTCAGTTTCAATGATGGTGTGGTAGGAGAAGTAGCACCTAAA
TCAGCGAATAAGAAAGCAGATCGAGATGCAGCCGCAGAAAAGTTGTATAATCTTGTAAATACACAA
TTAGACAAATTAGGCGATGGCGATTATGTAGATTTTTCTGTTGATTACAATCTAGAGAATAAGATTAT
CACCAATCAAGCCGATGCCGAAGCTATTGTTACTAAATTGAATTCGTTAAATGAAAAGACGCTAATT
GATATTGCAACTAAAGATACGTTTGGAATGGTGTCTAAAACGCAGGATTCTGAAGGAAAGAATGTT
GCGGCAACAAAAGCGTTAAAAGTAAAAGATGTGGCAACTTTTGGCTTAAAGAGTGGAGGTAGTG
AAGATACCGGATATGTTGTCGAAATGAAAGCGGGTGCTGTTGAAGATAAGTATGGTAAAGTAGGT
GATTCTACAGCTGGTATTGCAATCAATCTTCCATCAACAGGTTTAGAATATGCAGGCAAAGGAACA
ACTATTGATTTCAACAAAACCCTTAAAGTTGATGTAACTGGTGGTAGTACACCGAGTGCAGTTGCC
GTAAGTGGGTTTGTGACTAAAGATGATACAGATTTAGCATCAAATACTAATGGTAAGTCAGCTACTT
TGCCAGTAGTTGTTACTGTTCCTAATGTTGCTGAGCCAACTGTAGCCAGCGTAAGCAAGAGAATTA
TGCACAACGCATACTACTACGACAAGGACGCTAAGCGTGTTGGTACTGACAGCGTTAAGCGTTACA
ACTCAGTAAGCGTATTGCCAAACACTACTACTATCAACGGTAAGACTTACTACCAAGTAGTTGAAAA
CGGTAAGGCTGTTGACAAGTACATCAACGCTGCAAACATCGATGGTACTAAGCGTACTTTGAAGCA
CAACGCTTACGTTTACGCATCATCAAAGAAGCGTGCTAACAAGGTTGTATTGAAGAAGGGTGAAG
TTGTAACTACTTACGGTGCTTCATACACATTCAAGAACGGCCAAAAGTACTACAAGATCGGTGACA
ACACTGACAAGACTTACGTTAAGGTTGCAAACTTTAGATAATAAAGATCTTCGCGGCCGCATCACT
AGTGAATTCGCGGCCGC

FIG. 1D

TRANSLATED SlpA chimera fragment

```
MKKNLRIVSAAAAALLAVAPVAASAVSTVSAAAPVFAATTGTQGYTVVKN         50
DWKKAVKQLQDGLKDNSIGKITVSFNDGVVGEVAPKSANKKADRDAAAEK        100
LYNLVNTQLDKLGDGDYVDFSVDYNLENKIITNQADAEAIVTKLNSLNEK        150
TLIDIATKDTFGMVSKTQDSEGKNVAATKALKVKDVATFGLKSGGSEDTG        200
YVVEMKAGAVEDKYGKVGDSTAGIAINLPSTGLEYAGKGTTIDFNKTLKV        250
DVTGGSTPSAVAVSGFVTKDDTDLASNTNGKSATLPVVVTVPNVAEPTVA        300
SVSKRIMHNAYYYDKDAKRVGTDSVKRYNSVSVLPNTTTINGKTYYQVVE        350
NGKAVDKYINAANIDGTKRTLKHNAYVYASSKKRANKVVLKKGEVVTTYG        400
ASYTFKNGQKYYKIGDNTDKTYVKVANFR*
```

- Syrian Golden hamsters are safely and robustly colonized by recombinant Lactobacillus sp.
- Recombinant Lactobacillus protects hamsters from virulent *C. difficile* challenge Construct 1: *Lactobacillus casei* single-integration system (DNA sequence)

L casei camp int (3166 bp)

FIG. 6 (CONTIUED)
L casei camp int (3166 bp) (from 2141-3103 bp)
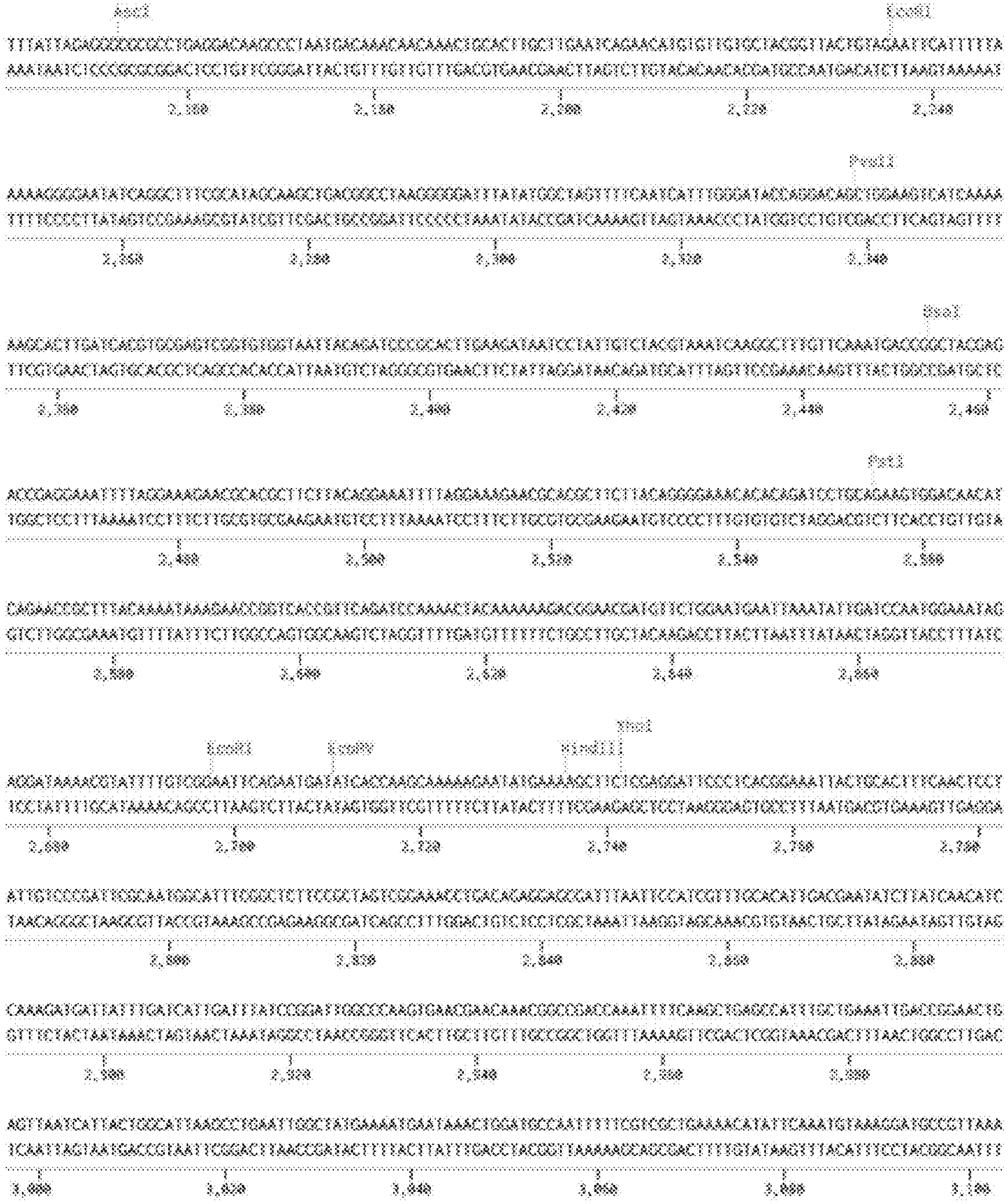

L. casei camp int (3166 bp) (from 3104-3166 bp)

```
                              PvuII          EcoRV    PmeI
GTGCTTCCGATTATGTAAAAAGATCCCGCTCACCCAGCTGGATCTTTCAGATATCGTTTAAAC
CACGAAGGCTAATACATTTTTCTAGGGCGAGTGGGTCGACCTAGAAAGTCTATAGCAAATTTG
         3,110    3,120    3,130    3,140    3,150    3,160
```

Construct 3: *Lactobacillus acidophilus* single-integration system (DNA sequence)

LA slpA Chi (3166 bp)

LA sipA Chi (3166 bp) (from 2141-3103 bp)

**Construct 4: *Lactobacillus acidophilus* doule-crossover ntegration system (DNA sequence)**

LA slpA double cross (3720 bp)

LA slpA double cross (3720 bp) (from 1071-2140 bp)

LA slpA double cross (3720 bp) (from 2141-3103 bp)

```
                          SEQUENCE LISTING

<160> NUMBER OF SEQ ID NOS: 28

<210> SEQ ID NO 1
<211> LENGTH: 244
<212> TYPE: PRT
<213> ORGANISM: Clostridium difficile

<400> SEQUENCE: 1

Ala Ala Pro Val Phe Ala Ala Thr Thr Gly Thr Gln Gly Tyr Thr Val
1               5                   10                  15

Val Lys Asn Asp Trp Lys Lys Ala Val Lys Gln Leu Gln Asp Gly Leu
            20                  25                  30

Lys Asp Asn Ser Ile Gly Lys Ile Thr Val Ser Phe Asn Asp Gly Val
        35                  40                  45

Val Gly Glu Val Ala Pro Lys Ser Ala Asn Lys Lys Ala Asp Arg Asp
    50                  55                  60

Ala Ala Ala Glu Lys Leu Tyr Asn Leu Val Asn Thr Gln Leu Asp Lys
65                  70                  75                  80

Leu Gly Asp Gly Asp Tyr Val Asp Phe Ser Val Asp Tyr Asn Leu Glu
                85                  90                  95

Asn Lys Ile Ile Thr Asn Gln Ala Asp Ala Glu Ala Ile Val Thr Lys
```

-continued

```
            100                 105                 110

Leu Asn Ser Leu Asn Glu Lys Thr Leu Ile Asp Ile Ala Thr Lys Asp
        115                 120                 125

Thr Phe Gly Met Val Ser Lys Thr Gln Asp Ser Glu Gly Lys Asn Val
    130                 135                 140

Ala Ala Thr Lys Ala Leu Lys Val Lys Asp Val Ala Thr Phe Gly Leu
145                 150                 155                 160

Lys Ser Gly Gly Ser Glu Asp Thr Gly Tyr Val Val Glu Met Lys Ala
                165                 170                 175

Gly Ala Val Glu Asp Lys Tyr Gly Lys Val Gly Asp Ser Thr Ala Gly
            180                 185                 190

Ile Ala Ile Asn Leu Pro Ser Thr Gly Leu Glu Tyr Ala Gly Lys Gly
        195                 200                 205

Thr Thr Ile Asp Phe Asn Lys Thr Leu Lys Val Asp Val Thr Gly Gly
    210                 215                 220

Ser Thr Pro Ser Ala Val Ala Val Ser Gly Phe Val Thr Lys Asp Asp
225                 230                 235                 240

Thr Asp Leu Ala


<210> SEQ ID NO 2
<211> LENGTH: 154
<212> TYPE: PRT
<213> ORGANISM: Lactobacillus acidophilus

<400> SEQUENCE: 2

Ser Asn Thr Asn Gly Lys Ser Ala Thr Leu Pro Val Val Val Thr Val
1               5                   10                  15

Pro Asn Val Ala Glu Pro Thr Val Ala Ser Val Ser Lys Arg Ile Met
            20                  25                  30

His Asn Ala Tyr Tyr Tyr Asp Lys Asp Ala Lys Arg Val Gly Thr Asp
        35                  40                  45

Ser Val Lys Arg Tyr Asn Ser Val Ser Val Leu Pro Asn Thr Thr Thr
    50                  55                  60

Ile Asn Gly Lys Thr Tyr Tyr Gln Val Val Glu Asn Gly Lys Ala Val
65                  70                  75                  80

Asp Lys Tyr Ile Asn Ala Ala Asn Ile Asp Gly Thr Lys Arg Thr Leu
                85                  90                  95

Lys His Asn Ala Tyr Val Tyr Ala Ser Ser Lys Lys Arg Ala Asn Lys
            100                 105                 110

Val Val Leu Lys Lys Gly Glu Val Val Thr Thr Tyr Gly Ala Ser Tyr
        115                 120                 125

Thr Phe Lys Asn Gly Gln Lys Tyr Tyr Lys Ile Gly Asp Asn Thr Asp
    130                 135                 140

Lys Thr Tyr Val Lys Val Ala Asn Phe Arg
145                 150


<210> SEQ ID NO 3
<211> LENGTH: 31
<212> TYPE: PRT
<213> ORGANISM: Lactobacillus acidophilus

<400> SEQUENCE: 3

Met Lys Lys Asn Leu Arg Ile Val Ser Ala Ala Ala Ala Ala Leu Leu
1               5                   10                  15

Ala Val Ala Pro Val Ala Ala Ser Ala Val Ser Thr Val Ser Ala
            20                  25                  30
```

-continued

<210> SEQ ID NO 4
<211> LENGTH: 429
<212> TYPE: PRT
<213> ORGANISM: Artificial Sequence
<220> FEATURE:
<223> OTHER INFORMATION: SlpA Chimeric protein

<400> SEQUENCE: 4

```
Met Lys Lys Asn Leu Arg Ile Val Ser Ala Ala Ala Ala Ala Leu Leu
1               5                   10                  15

Ala Val Ala Pro Val Ala Ala Ser Ala Val Ser Thr Val Ser Ala Ala
            20                  25                  30

Ala Pro Val Phe Ala Ala Thr Thr Gly Thr Gln Gly Tyr Thr Val Val
        35                  40                  45

Lys Asn Asp Trp Lys Lys Ala Val Lys Gln Leu Gln Asp Gly Leu Lys
    50                  55                  60

Asp Asn Ser Ile Gly Lys Ile Thr Val Ser Phe Asn Asp Gly Val Val
65                  70                  75                  80

Gly Glu Val Ala Pro Lys Ser Ala Asn Lys Lys Ala Asp Arg Asp Ala
                85                  90                  95

Ala Ala Glu Lys Leu Tyr Asn Leu Val Asn Thr Gln Leu Asp Lys Leu
            100                 105                 110

Gly Asp Gly Asp Tyr Val Asp Phe Ser Val Asp Tyr Asn Leu Glu Asn
        115                 120                 125

Lys Ile Ile Thr Asn Gln Ala Asp Ala Glu Ala Ile Val Thr Lys Leu
    130                 135                 140

Asn Ser Leu Asn Glu Lys Thr Leu Ile Asp Ile Ala Thr Lys Asp Thr
145                 150                 155                 160

Phe Gly Met Val Ser Lys Thr Gln Asp Ser Glu Gly Lys Asn Val Ala
                165                 170                 175

Ala Thr Lys Ala Leu Lys Val Lys Asp Val Ala Thr Phe Gly Leu Lys
            180                 185                 190

Ser Gly Gly Ser Glu Asp Thr Gly Tyr Val Val Glu Met Lys Ala Gly
        195                 200                 205

Ala Val Glu Asp Lys Tyr Gly Lys Val Gly Asp Ser Thr Ala Gly Ile
    210                 215                 220

Ala Ile Asn Leu Pro Ser Thr Gly Leu Glu Tyr Ala Gly Lys Gly Thr
225                 230                 235                 240

Thr Ile Asp Phe Asn Lys Thr Leu Lys Val Asp Val Thr Gly Gly Ser
                245                 250                 255

Thr Pro Ser Ala Val Ala Val Ser Gly Phe Val Thr Lys Asp Asp Thr
            260                 265                 270

Asp Leu Ala Ser Asn Thr Asn Gly Lys Ser Ala Thr Leu Pro Val Val
        275                 280                 285

Val Thr Val Pro Asn Val Ala Glu Pro Thr Val Ala Ser Val Ser Lys
    290                 295                 300

Arg Ile Met His Asn Ala Tyr Tyr Tyr Asp Lys Asp Ala Lys Arg Val
305                 310                 315                 320

Gly Thr Asp Ser Val Lys Arg Tyr Asn Ser Val Ser Val Leu Pro Asn
                325                 330                 335

Thr Thr Thr Ile Asn Gly Lys Thr Tyr Tyr Gln Val Val Glu Asn Gly
            340                 345                 350

Lys Ala Val Asp Lys Tyr Ile Asn Ala Ala Asn Ile Asp Gly Thr Lys
        355                 360                 365
```

-continued

Arg Thr Leu Lys His Asn Ala Tyr Val Tyr Ala Ser Ser Lys Lys Arg
    370                 375                 380

Ala Asn Lys Val Val Leu Lys Lys Gly Glu Val Val Thr Thr Tyr Gly
385                 390                 395                 400

Ala Ser Tyr Thr Phe Lys Asn Gly Gln Lys Tyr Tyr Lys Ile Gly Asp
                405                 410                 415

Asn Thr Asp Lys Thr Tyr Val Lys Val Ala Asn Phe Arg
            420                 425

<210> SEQ ID NO 5
<211> LENGTH: 1323
<212> TYPE: DNA
<213> ORGANISM: Artificial Sequence
<220> FEATURE:
<223> OTHER INFORMATION: SlpA Chimeric gene

<400> SEQUENCE: 5
ggatccatga agaaaaattt aagaatcgtt agcgctgctg ctgctgcttt acttgctgtt 60
gctccagttg ctgcttctgc tgtatctact gttagcgctg ctgcacctgt atttgctgca 120
accactggta cacaaggcta tacggtggtt aagaatgatt ggaaaaaggc tgtcaaacaa 180
ttacaagatg gacttaaaga taatagtatt ggtaagatta cggtcagttt caatgatggt 240
gtggtaggag aagtagcacc taaatcagcg aataagaaag cagatcgaga tgcagccgca 300
gaaaagttgt ataatcttgt aaatacacaa ttagacaaat taggcgatgg cgattatgta 360
gatttttctg ttgattacaa tctagagaat aagattatca ccaatcaagc cgatgccgaa 420
gctattgtta ctaaattgaa ttcgttaaat gaaaagacgc taattgatat tgcaactaaa 480
gatacgtttg gaatggtgtc taaaacgcag gattctgaag gaaagaatgt tgcggcaaca 540
aaagcgttaa aagtaaaaga tgtggcaact tttggcttaa agagtggagg tagtgaagat 600
accggatatg ttgtcgaaat gaaagcgggt gctgttgaag ataagtatgg taaagtaggt 660
gattctacag ctggtattgc aatcaatctt ccatcaacag gtttagaata tgcaggcaaa 720
ggaacaacta ttgatttcaa caaaaccctt aaagttgatg taactggtgg tagtacaccg 780
agtgcagttg ccgtaagtgg gtttgtgact aaagatgata cagatttagc atcaaatact 840
aatggtaagt cagctacttt gccagtagtt gttactgttc ctaatgttgc tgagccaact 900
gtagccagcg taagcaagag aattatgcac aacgcatact actacgacaa ggacgctaag 960
cgtgttggta ctgacagcgt taagcgttac aactcagtaa gcgtattgcc aaacactact 1020
actatcaacg gtaagactta ctaccaagta gttgaaaacg gtaaggctgt tgacaagtac 1080
atcaacgctg caaacatcga tggtactaag cgtactttga agcacaacgc ttacgtttac 1140
gcatcatcaa agaagcgtgc taacaaggtt gtattgaaga agggtgaagt tgtaactact 1200
tacggtgctt catacacatt caagaacggc caaaagtact acaagatcgg tgacaacact 1260
gacaagactt acgttaaggt tgcaaacttt agataataaa gatcttcgaa ttcccgcggc 1320
cgc 1323

<210> SEQ ID NO 6
<211> LENGTH: 719
<212> TYPE: PRT
<213> ORGANISM: Clostridium difficile

<400> SEQUENCE: 6

Met Asn Lys Lys Asn Ile Ala Ile Ala Met Ser Gly Leu Thr Val Leu
1               5                   10                  15

-continued

```
Ala Ser Ala Ala Pro Val Phe Ala Ala Thr Thr Gly Thr Gln Gly Tyr
            20                  25                  30

Thr Val Val Lys Asn Asp Trp Lys Lys Ala Val Lys Gln Leu Gln Asp
        35                  40                  45

Gly Leu Lys Asp Asn Ser Ile Gly Lys Ile Thr Val Ser Phe Asn Asp
    50                  55                  60

Gly Val Val Gly Glu Val Ala Pro Lys Ser Ala Asn Lys Lys Ala Asp
65                  70                  75                  80

Arg Asp Ala Ala Ala Glu Lys Leu Tyr Asn Leu Val Asn Thr Gln Leu
                85                  90                  95

Asp Lys Leu Gly Asp Gly Asp Tyr Val Asp Phe Ser Val Asp Tyr Asn
            100                 105                 110

Leu Glu Asn Lys Ile Ile Thr Asn Gln Ala Asp Ala Glu Ala Ile Val
        115                 120                 125

Thr Lys Leu Asn Ser Leu Asn Glu Lys Thr Leu Ile Asp Ile Ala Thr
    130                 135                 140

Lys Asp Thr Phe Gly Met Val Ser Lys Thr Gln Asp Ser Glu Gly Lys
145                 150                 155                 160

Asn Val Ala Ala Thr Lys Ala Leu Lys Val Lys Asp Val Ala Thr Phe
                165                 170                 175

Gly Leu Lys Ser Gly Gly Ser Glu Asp Thr Gly Tyr Val Val Glu Met
            180                 185                 190

Lys Ala Gly Ala Val Glu Asp Lys Tyr Gly Lys Val Gly Asp Ser Thr
        195                 200                 205

Ala Gly Ile Ala Ile Asn Leu Pro Ser Thr Gly Leu Glu Tyr Ala Gly
    210                 215                 220

Lys Gly Thr Thr Ile Asp Phe Asn Lys Thr Leu Lys Val Asp Val Thr
225                 230                 235                 240

Gly Gly Ser Thr Pro Ser Ala Val Ala Val Ser Gly Phe Val Thr Lys
                245                 250                 255

Asp Asp Thr Asp Leu Ala Lys Ser Gly Thr Ile Asn Val Arg Val Ile
            260                 265                 270

Asn Ala Lys Glu Glu Ser Ile Asp Ile Asp Ala Ser Ser Tyr Thr Ser
        275                 280                 285

Ala Glu Asn Leu Ala Lys Arg Tyr Val Phe Asp Pro Asp Glu Ile Ser
    290                 295                 300

Glu Ala Tyr Lys Ala Ile Val Ala Leu Gln Asn Asp Gly Ile Glu Ser
305                 310                 315                 320

Asn Leu Val Gln Leu Val Asn Gly Lys Tyr Gln Val Ile Phe Tyr Pro
                325                 330                 335

Glu Gly Lys Arg Leu Glu Thr Lys Ser Ala Asn Asp Thr Ile Ala Ser
            340                 345                 350

Gln Asp Thr Pro Ala Lys Val Val Ile Lys Ala Asn Lys Leu Lys Asp
        355                 360                 365

Leu Lys Asp Tyr Val Asp Asp Leu Lys Thr Tyr Asn Asn Thr Tyr Ser
    370                 375                 380

Asn Val Val Thr Val Ala Gly Glu Asp Arg Ile Glu Thr Ala Ile Glu
385                 390                 395                 400

Leu Ser Ser Lys Tyr Tyr Asn Ser Asp Asp Lys Asn Ala Ile Thr Asp
                405                 410                 415

Lys Ala Val Asn Asp Ile Val Leu Val Gly Ser Thr Ser Ile Val Asp
            420                 425                 430
```

-continued

```
Gly Leu Val Ala Ser Pro Leu Ala Ser Glu Lys Thr Ala Pro Leu Leu
        435                 440                 445

Leu Thr Ser Lys Asp Lys Leu Asp Ser Ser Val Lys Ser Glu Ile Lys
    450                 455                 460

Arg Val Met Asn Leu Lys Ser Asp Thr Gly Ile Asn Thr Ser Lys Lys
465                 470                 475                 480

Val Tyr Leu Ala Gly Gly Val Asn Ser Ile Ser Lys Asp Val Glu Asn
                485                 490                 495

Glu Leu Lys Asn Met Gly Leu Lys Val Thr Arg Leu Ser Gly Glu Asp
            500                 505                 510

Arg Tyr Glu Thr Ser Leu Ala Ile Ala Asp Glu Ile Gly Leu Asp Asn
        515                 520                 525

Asp Lys Ala Phe Val Val Gly Gly Thr Gly Leu Ala Asp Ala Met Ser
    530                 535                 540

Ile Ala Pro Val Ala Ser Gln Leu Lys Asp Gly Asp Ala Thr Pro Ile
545                 550                 555                 560

Val Val Val Asp Gly Lys Ala Lys Glu Ile Ser Asp Asp Ala Lys Ser
                565                 570                 575

Phe Leu Gly Thr Ser Asp Val Asp Ile Ile Gly Gly Lys Asn Ser Val
            580                 585                 590

Ser Lys Glu Ile Glu Glu Ser Ile Asp Ser Ala Thr Gly Lys Thr Pro
        595                 600                 605

Asp Arg Ile Ser Gly Asp Asp Arg Gln Ala Thr Asn Ala Glu Val Leu
    610                 615                 620

Lys Glu Asp Asp Tyr Phe Thr Asp Gly Glu Val Val Asn Tyr Phe Val
625                 630                 635                 640

Ala Lys Asp Gly Ser Thr Lys Glu Asp Gln Leu Val Asp Ala Leu Ala
                645                 650                 655

Ala Ala Pro Ile Ala Gly Arg Phe Lys Glu Ser Pro Ala Pro Ile Ile
            660                 665                 670

Leu Ala Thr Asp Thr Leu Ser Ser Asp Gln Asn Val Ala Val Ser Lys
        675                 680                 685

Ala Val Pro Lys Asp Gly Gly Thr Asn Leu Val Gln Val Gly Lys Gly
    690                 695                 700

Ile Ala Ser Ser Val Ile Asn Lys Met Lys Asp Leu Leu Asp Met
705                 710                 715


<210> SEQ ID NO 7
<211> LENGTH: 444
<212> TYPE: PRT
<213> ORGANISM: Lactobacillus acidophilus

<400> SEQUENCE: 7

Met Lys Lys Asn Leu Arg Ile Val Ser Ala Ala Ala Ala Ala Leu Leu
1               5                   10                  15

Ala Val Ala Pro Val Ala Ala Ser Ala Val Ser Thr Val Ser Ala Ala
            20                  25                  30

Thr Thr Ile Asn Ala Ser Ser Ser Ala Ile Asn Thr Asn Thr Asn Ala
        35                  40                  45

Lys Tyr Asp Val Asp Val Thr Pro Ser Val Ser Ala Val Ala Ala Asn
    50                  55                  60

Thr Ala Asn Asn Thr Pro Ala Ile Ala Gly Asn Leu Thr Gly Thr Ile
65                  70                  75                  80

Ser Ala Ser Tyr Asn Gly Lys Thr Tyr Thr Ala Asn Leu Lys Ala Asp
                85                  90                  95
```

Thr Glu Asn Ala Thr Ile Thr Ala Ala Gly Ser Thr Thr Ala Val Lys
100 105 110

Pro Ala Glu Leu Ala Ala Gly Val Ala Tyr Thr Val Thr Val Asn Asp
115 120 125

Val Ser Phe Asn Phe Gly Ser Glu Asn Ala Gly Lys Thr Val Thr Leu
130 135 140

Gly Ser Ala Asn Ser Asn Val Lys Phe Thr Gly Thr Asn Ser Asp Asn
145 150 155 160

Gln Thr Glu Thr Asn Val Ser Thr Leu Lys Val Lys Leu Asp Gln Asn
165 170 175

Gly Val Ala Ser Leu Thr Asn Val Ser Ile Ala Asn Val Tyr Ala Ile
180 185 190

Asn Thr Thr Asp Asn Ser Asn Val Asn Phe Tyr Asp Val Thr Ser Gly
195 200 205

Ala Thr Val Thr Asn Gly Ala Val Ser Val Asn Ala Asp Asn Gln Gly
210 215 220

Gln Val Asn Val Ala Asn Val Val Ala Ala Ile Asn Ser Lys Tyr Phe
225 230 235 240

Ala Ala Gln Tyr Ala Asp Lys Lys Leu Asn Thr Arg Thr Ala Asn Thr
245 250 255

Glu Asp Ala Ile Lys Ala Ala Leu Lys Asp Gln Lys Ile Asp Val Asn
260 265 270

Ser Val Gly Tyr Phe Lys Ala Pro His Thr Phe Thr Val Asn Val Lys
275 280 285

Ala Thr Ser Asn Thr Asn Gly Lys Ser Ala Thr Leu Pro Val Val Val
290 295 300

Thr Val Pro Asn Val Ala Glu Pro Thr Val Ala Ser Val Ser Lys Arg
305 310 315 320

Ile Met His Asn Ala Tyr Tyr Tyr Asp Lys Asp Ala Lys Arg Val Gly
325 330 335

Thr Asp Ser Val Lys Arg Tyr Asn Ser Val Ser Val Leu Pro Asn Thr
340 345 350

Thr Thr Ile Asn Gly Lys Thr Tyr Tyr Gln Val Val Glu Asn Gly Lys
355 360 365

Ala Val Asp Lys Tyr Ile Asn Ala Ala Asn Ile Asp Gly Thr Lys Arg
370 375 380

Thr Leu Lys His Asn Ala Tyr Val Tyr Ala Ser Ser Lys Lys Arg Ala
385 390 395 400

Asn Lys Val Val Leu Lys Lys Gly Glu Val Val Thr Thr Tyr Gly Ala
405 410 415

Ser Tyr Thr Phe Lys Asn Gly Gln Lys Tyr Tyr Lys Ile Gly Asp Asn
420 425 430

Thr Asp Lys Thr Tyr Val Lys Val Ala Asn Phe Arg
435 440

<210> SEQ ID NO 8
<211> LENGTH: 323
<212> TYPE: PRT
<213> ORGANISM: Clostridium difficile

<400> SEQUENCE: 8

Ala Gly Glu Asp Arg Ile Glu Thr Ala Ile Glu Leu Ser Ser Lys Tyr
1 5 10 15

Tyr Asn Ser Asp Asp Lys Asn Ala Ile Thr Asp Lys Ala Val Asn Asp

```
            20                  25                  30

Ile Val Leu Val Gly Ser Thr Ser Ile Val Asp Gly Leu Val Ala Ser
        35                  40                  45

Pro Leu Ala Ser Glu Lys Thr Ala Pro Leu Leu Leu Thr Ser Lys Asp
    50                  55                  60

Lys Leu Asp Ser Ser Val Lys Ser Glu Ile Lys Arg Val Met Asn Leu
65                  70                  75                  80

Lys Ser Asp Thr Gly Ile Asn Thr Ser Lys Lys Val Tyr Leu Ala Gly
                85                  90                  95

Gly Val Asn Ser Ile Ser Lys Asp Val Glu Asn Glu Leu Lys Asn Met
            100                 105                 110

Gly Leu Lys Val Thr Arg Leu Ser Gly Glu Asp Arg Tyr Glu Thr Ser
        115                 120                 125

Leu Ala Ile Ala Asp Glu Ile Gly Leu Asp Asn Asp Lys Ala Phe Val
    130                 135                 140

Val Gly Gly Thr Gly Leu Ala Asp Ala Met Ser Ile Ala Pro Val Ala
145                 150                 155                 160

Ser Gln Leu Lys Asp Gly Asp Ala Thr Pro Ile Val Val Val Asp Gly
                165                 170                 175

Lys Ala Lys Glu Ile Ser Asp Asp Ala Lys Ser Phe Leu Gly Thr Ser
            180                 185                 190

Asp Val Asp Ile Ile Gly Gly Lys Asn Ser Val Ser Lys Glu Ile Glu
        195                 200                 205

Glu Ser Ile Asp Ser Ala Thr Gly Lys Thr Pro Asp Arg Ile Ser Gly
    210                 215                 220

Asp Asp Arg Gln Ala Thr Asn Ala Glu Val Leu Lys Glu Asp Asp Tyr
225                 230                 235                 240

Phe Thr Asp Gly Glu Val Val Asn Tyr Phe Val Ala Lys Asp Gly Ser
                245                 250                 255

Thr Lys Glu Asp Gln Leu Val Asp Ala Leu Ala Ala Ala Pro Ile Ala
            260                 265                 270

Gly Arg Phe Lys Glu Ser Pro Ala Pro Ile Ile Leu Ala Thr Asp Thr
        275                 280                 285

Leu Ser Ser Asp Gln Asn Val Ala Val Ser Lys Ala Val Pro Lys Asp
    290                 295                 300

Gly Gly Thr Asn Leu Val Gln Val Gly Lys Gly Ile Ala Ser Ser Val
305                 310                 315                 320

Ile Asn Lys
```

<210> SEQ ID NO 9
<211> LENGTH: 1338
<212> TYPE: DNA
<213> ORGANISM: Artificial Sequence
<220> FEATURE:
<223> OTHER INFORMATION: SlpA Chimeric gene

<400> SEQUENCE: 9

```
ggatccatga agaaaaattt aagaatcgtt agcgctgctg ctgctgcttt acttgctgtt     60

gctccagttg ctgcttctgc tgtatctact gttagcgctg ctgcacctgt atttgctgca    120

accactggta cacaaggcta tacggtggtt aagaatgatt ggaaaaaggc tgtcaaacaa    180

ttacaagatg gacttaaaga taatagtatt ggtaagatta cggtcagttt caatgatggt    240

gtggtaggag aagtagcacc taaatcagcg aataagaaag cagatcgaga tgcagccgca    300

gaaaagttgt ataatcttgt aaatacacaa ttagacaaat taggcgatgg cgattatgta    360
```

gatttttctg ttgattacaa tctagagaat aagattatca ccaatcaagc cgatgccgaa 420
gctattgtta ctaaattgaa ttcgttaaat gaaaagacgc taattgatat tgcaactaaa 480
gatacgtttg gaatggtgtc taaaacgcag gattctgaag gaaagaatgt tgcggcaaca 540
aaagcgttaa aagtaaaaga tgtggcaact tttggcttaa agagtggagg tagtgaagat 600
accggatatg ttgtcgaaat gaaagcgggt gctgttgaag ataagtatgg taaagtaggt 660
gattctacag ctggtattgc aatcaatctt ccatcaacag gtttagaata tgcaggcaaa 720
ggaacaacta ttgatttcaa caaaaccctt aaagttgatg taactggtgg tagtacaccg 780
agtgcagttg ccgtaagtgg gtttgtgact aaagatgata cagatttagc atcaaatact 840
aatggtaagt cagctacttt gccagtagtt gttactgttc ctaatgttgc tgagccaact 900
gtagccagcg taagcaagag aattatgcac aacgcatact actacgacaa ggacgctaag 960
cgtgttggta ctgacagcgt taagcgttac aactcagtaa gcgtattgcc aaacactact 1020
actatcaacg gtaagactta ctaccaagta gttgaaaacg gtaaggctgt tgacaagtac 1080
atcaacgctg caaacatcga tggtactaag cgtactttga agcacaacgc ttacgtttac 1140
gcatcatcaa agaagcgtgc taacaaggtt gtattgaaga agggtgaagt tgtaactact 1200
tacggtgctt catacacatt caagaacggc caaaagtact acaagatcgg tgacaacact 1260
gacaagactt acgttaaggt tgcaaacttt agataataaa gatcttcgcg gccgcatcac 1320
tagtgaattc gcggccgc 1338

<210> SEQ ID NO 10
<211> LENGTH: 250
<212> TYPE: DNA
<213> ORGANISM: Lactobacillus acidophilus

<400> SEQUENCE: 10
tataaatggc aataccacaa aataactgtt gacaagttgt gaaagcgata ttatcattta 60
attgtaaatt gaaaacgttt ccaaagtgtt caaatagttt tttgctaaat aattattttt 120
ttgtagcgaa atagaaacgt ttcaattaat ttaaaacaat tagatcttag taggaaacct 180
tttaattttt gtgcaaaatt gaaacgtttc aaaaggagga aaaatgaaaa aatggaaatt 240
aggagttgca 250

<210> SEQ ID NO 11
<211> LENGTH: 7
<212> TYPE: PRT
<213> ORGANISM: Lactobacillus acidophilus

<400> SEQUENCE: 11

Ile Asn Gly Asn Thr Thr Lys
1               5

<210> SEQ ID NO 12
<211> LENGTH: 9
<212> TYPE: PRT
<213> ORGANISM: Lactobacillus acidophilus

<400> SEQUENCE: 12

Met Lys Lys Trp Lys Leu Gly Val Ala
1               5

<210> SEQ ID NO 13
<211> LENGTH: 250
<212> TYPE: DNA

-continued

<213> ORGANISM: Lactobacillus acidophilus

<400> SEQUENCE: 13

```
gttgtcatag ttaatttctt ttctttttaa aaaacttact tacgtttatt atacaaaata     60

tttactcaat tccaataaat attaatttta gcaaaaacaa atttttttaag aatcttcgta    120

ataaatattt tactgttttt agataaatat tttattttat tggttaattt tttatttggt    180

gatataataa aagcgttttc aaaaataatt tattatagaa atcaggtatt agtatgcaag    240

caaacataag                                                            250
```

<210> SEQ ID NO 14
<211> LENGTH: 5
<212> TYPE: PRT
<213> ORGANISM: Lactobacillus acidophilus

<400> SEQUENCE: 14

```
Met Gln Ala Asn Ile
1               5
```

<210> SEQ ID NO 15
<211> LENGTH: 250
<212> TYPE: DNA
<213> ORGANISM: Lactobacillus acidophilus

<400> SEQUENCE: 15

```
tcttgtgcaa taatgtctga ttttgattcc gtcatttatg tctttccttt ctttgtacat     60

ttattatatt cataaatgta tagacaagta aagcataatt taagttacta taaagtaaat    120

attgtgatcg ctttcaaaaa atatattgac aacttgtata tacaagttta atataatagc    180

taaatctaat gaaaacgctt tatacaggag aaaaacaatg aatgaaaaca atgaaattgc    240

aattctcgct                                                            250
```

<210> SEQ ID NO 16
<211> LENGTH: 11
<212> TYPE: PRT
<213> ORGANISM: Lactobacillus acidophilus

<400> SEQUENCE: 16

```
Gln Ala Ile Ile Asp Ser Lys Ser Glu Thr Met
1               5                   10
```

<210> SEQ ID NO 17
<211> LENGTH: 11
<212> TYPE: PRT
<213> ORGANISM: Lactobacillus acidophilus

<400> SEQUENCE: 17

```
Met Asn Glu Asn Asn Glu Ile Ala Ile Leu Ala
1               5                   10
```

<210> SEQ ID NO 18
<211> LENGTH: 200
<212> TYPE: DNA
<213> ORGANISM: Lactobacillus acidophilus

<400> SEQUENCE: 18

```
ttttgttttt catgattttt acacttctct tagtatgctt ttgttataag ttagcacaaa     60

aaagcagaaa ataaaaagta gaaataaaaa aagatgtttt tttgcccata tctctatgaa    120

aaaaactgtg aaatgtgtaa aatatggatg aaacattgaa tttaaaagga gatatttcat    180
```

gtcaaaatta gttttaatcc 200

<210> SEQ ID NO 19
<211> LENGTH: 4
<212> TYPE: PRT
<213> ORGANISM: Lactobacillus acidophilus

<400> SEQUENCE: 19

Lys Asn Lys Met
1

<210> SEQ ID NO 20
<211> LENGTH: 7
<212> TYPE: PRT
<213> ORGANISM: Lactobacillus acidophilus

<400> SEQUENCE: 20

Met Ser Lys Leu Val Leu Ile
1 5

<210> SEQ ID NO 21
<211> LENGTH: 3166
<212> TYPE: DNA
<213> ORGANISM: Artificial Sequence
<220> FEATURE:
<223> OTHER INFORMATION: Polynucleotide for Lactobacillus integration

<400> SEQUENCE: 21
ggccggcctt ggtgctcaaa tgcgctttga cttatcaaaa gggtttccaa ttttaaccac 60
taaaaaggtt ccattcggtt taattaaaag tgaactccta tggttcttac gaggggacac 120
taatattcgt tttttattag aacataaaaa tcatatttgg gatgagtggg catttaaaaa 180
ttgggttaac agtgatgaat atactggtcc tgatatgact gattttggtt tacgaagtca 240
aagtgatccg gaatttaata aaatttatca agctgaatta aaaaaatttg atcgacgtat 300
ccttgatgat gagaacttcg ccaaaaaata tggtaattta ggcgacgttt atggtgcaca 360
atggcgccat tggcaaaagc gagatggtag ctttattgat caaattgaag atctattaga 420
cttctttttc ctccgatcat atgatcggag gaaaaagaaa tctaatagtt ttacacttct 480
cttagtatgc ttttgttata agttagcaca aaaaagcaga aaataaaaag tagaaataaa 540
aaaagatgtt tttttgccca tatctctatg aaaaaaactg tgaaatgtgt aaaatatgga 600
tgaaacattg aatttaaaag gagatattat gaagaaaaat ttaagaatcg ttagcgctgc 660
tgctgctgct ttacttgctg ttgctccagt tgctgcttct gctgtatcta ctgttagcgc 720
tgctgcacct gtatttgctg caaccactgg tacacaaggc tatacggtgg ttaagaatga 780
ttggaaaaag gctgtcaaac aattacaaga tggacttaaa gataatagta ttggtaagat 840
tacggtcagt ttcaatgatg gtgtggtagg agaagtagca cctaaatcag cgaataagaa 900
agcagatcga gatgcagccg cagaaaagtt gtataatctt gtaaatacac aattagacaa 960
attaggcgat ggcgattatg tagatttttc tgttgattac aatctagaga ataagattat 1020
caccaatcaa gccgatgccg aagctattgt tactaaattg aattcgttaa atgaaaagac 1080
gctaattgat attgcaacta aagatacgtt tggaatggtg tctaaaacgc aggattctga 1140
aggaaagaat gttgcggcaa caaaagcgtt aaaagtaaaa gatgtggcaa cttttggctt 1200
aaagagtgga ggtagtgaag ataccggata tgttgtcgaa atgaaagcgg gtgctgttga 1260
agataagtat ggtaaagtag gtgattctac agctggtatt gcaatcaatc ttccatcaac 1320
aggtttagaa tatgcaggca aaggaacaac tattgatttc aacaaaaccc ttaaagttga 1380

-continued tgtaactggt ggtagtacac cgagtgcagt tgccgtaagt gggtttgtga ctaaagatga 1440
tacagattta gcatcaaata ctaatggtaa gtcagctact ttgccagtag ttgttactgt 1500
tcctaatgtt gctgagccaa ctgtagccag cgtaagcaag agaattatgc acaacgcata 1560
ctactacgac aaggacgcta agcgtgttgg tactgacagc gttaagcgtt acaactcagt 1620
aagcgtattg ccaaacacta ctactatcaa cggtaagact tactaccaag tagttgaaaa 1680
cggtaaggct gttgacaagt acatcaacgc tgcaaacatc gatggtacta agcgtacttt 1740
gaagcacaac gcttacgttt acgcatcatc aaagaagcgt gctaacaagg ttgtattgaa 1800
gaagggtgaa gttgtaacta cttacggtgc ttcatacaca ttcaagaacg gccaaaagta 1860
ctacaagatc ggtgacaaca ctgacaagac ttacgttaag gttgcaaact ttagataata 1920
agatcttatt aagattaccg ttatccgtga aaaacgagtg gtagcaattg ctaaataaca 1980
aaaagagtat gagtttttgc tcatactctt tttgttattt gtgcaaatac cgctctactt 2040
gtataattag aacaagtata taaggaaagt agccgaatat gtttaaaatt attgttgaat 2100
tattcttatt agtaattatt tcagctgctc aattacgcca tttattagag ggcgcgcctg 2160
aggacaagcc ctaatgacaa acaacaaact gcacttgctt gaatcagaac atgtgttgtg 2220
ctacggttac tgtagaattc atttttaaaa aggggaatat caggctttcg catagcaagc 2280
tgacggccta agggggattt atatggctag ttttcaatca tttgggatac caggacagct 2340
ggaagtcatc aaaaaagcac ttgatcacgt gcgagtcggt gtggtaatta cagatcccgc 2400
acttgaagat aatcctattg tctacgtaaa tcaaggcttt gttcaaatga ccggctacga 2460
gaccgaggaa attttaggaa agaacgcacg cttcttacag gaaattttag gaaagaacgc 2520
acgcttctta caggggaaac acacagatcc tgcagaagtg gacaacatca gaaccgcttt 2580
acaaaataaa gaaccggtca ccgttcagat ccaaaactac aaaaaagacg gaacgatgtt 2640
ctggaatgaa ttaaatattg atccaatgga aatagaggat aaaacgtatt ttgtcggaat 2700
tcagaatgat atcaccaagc aaaaagaata tgaaaagctt ctcgaggatt ccctcacgga 2760
aattactgca ctttcaactc ctattgtccc gattcgcaat ggcatttcgg ctcttccgct 2820
agtcggaaac ctgacagagg agcgatttaa ttccatcgtt tgcacattga cgaatatctt 2880
atcaacatcc aaagatgatt atttgatcat tgatttatcc ggattggccc aagtgaacga 2940
acaaacggcc gaccaaattt tcaagctgag ccatttgctg aaattgaccg gaactgagtt 3000
aatcattact ggcattaagc ctgaattggc tatgaaaatg aataaactgg atgccaattt 3060
ttcgtcgctg aaaacatatt caaatgtaaa ggatgccgtt aaagtgcttc cgattatgta 3120
aaaagatccc gctcacccag ctggatcttt cagatatcgt ttaaac 3166

<210> SEQ ID NO 22
<211> LENGTH: 3166
<212> TYPE: DNA
<213> ORGANISM: Artificial Sequence
<220> FEATURE:
<223> OTHER INFORMATION: Polynucleotide for Lactobacillus integration

<400> SEQUENCE: 22
gtttaaacga tatctgaaag atccagctgg gtgagcggga tctttttaca taatcggaag 60
cactttaacg gcatccttta catttgaata tgttttcagc gacgaaaaat tggcatccag 120
tttattcatt ttcatagcca attcaggctt aatgccagta atgattaact cagttccggt 180
caatttcagc aaatggctca gcttgaaaat ttggtcggcc gtttgttcgt tcacttgggc 240

-continued

```
caatccggat aaatcaatga tcaaataatc atctttggat gttgataaga tattcgtcaa    300
tgtgcaaacg atggaattaa atcgctcctc tgtcaggttt ccgactagcg gaagagccga    360
aatgccattg cgaatcggga caataggagt tgaaagtgca gtaatttccg tgagggaatc    420
ctcgagaagc ttttcatatt ctttttgctt ggtgatatca ttctgaattc cgacaaaata    480
cgttttatcc tctatttcca ttggatcaat atttaattca ttccagaaca tcgttccgtc    540
tttttgtag ttttggatct gaacggtgac cggttcttta ttttgtaaag cggttctgat    600
gttgtccact tctgcaggat ctgtgtgttt cccctgtaag aagcgtgcgt tctttcctaa    660
aatttcctgt aagaagcgtg cgttctttcc taaaatttcc tcggtctcgt agccggtcat    720
ttgaacaaag ccttgattta cgtagacaat aggattatct tcaagtgcgg gatctgtaat    780
taccacaccg actcgcacgt gatcaagtgc tttttttgatg acttccagct gtcctggtat    840
cccaaatgat tgaaaactag ccatataaat ccccccttagg ccgtcagctt gctatgcgaa    900
agcctgatat tcccctttt aaaaatgaat tctacagtaa ccgtagcaca acacatgttc    960
tgattcaagc aagtgcagtt tgttgtttgt cattagggct tgtcctcagg cgcgccctct   1020
aataaatggc gtaattgagc agctgaaata attactaata agaataattc aacaataatt   1080
ttaaacatat tcggctactt tccttatata cttgttctaa ttatacaagt agagcggtat   1140
ttgcacaaat aacaaaaaga gtatgagcaa aaactcatac tctttttgtt atttagcaat   1200
tgctaccact cgtttttcac ggataacggt aatcttaata agatcttatt atctaaagtt   1260
tgcaacctta acgtaagtct tgtcagtgtt gtcaccgatc ttgtagtact tttggccgtt   1320
cttgaatgtg tatgaagcac cgtaagtagt tacaacttca cccttcttca atacaacctt   1380
gttagcacgc ttctttgatg atgcgtaaac gtaagcgttg tgcttcaaag tacgcttagt   1440
accatcgatg tttgcagcgt tgatgtactt gtcaacagcc ttaccgtttt caactacttg   1500
gtagtaagtc ttaccgttga tagtagtagt gtttggcaat acgcttactg agttgtaacg   1560
cttaacgctg tcagtaccaa cacgcttagc gtccttgtcg tagtagtatg cgttgtgcat   1620
aattctcttg cttacgctgg ctacagttgg ctcagcaaca ttaggaacag taacaactac   1680
tggcaaagta gctgacttac cattagtatt tgatgctaaa tctgtatcat ctttagtcac   1740
aaacccactt acggcaactg cactcggtgt actaccacca gttacatcaa ctttaagggt   1800
tttgttgaaa tcaatagttg ttcctttgcc tgcatattct aaacctgttg atggaagatt   1860
gattgcaata ccagctgtag aatcacctac tttaccatac ttatcttcaa cagcacccgc   1920
tttcatttcg acaacatatc cggtatcttc actacctcca ctctttaagc caaaagttgc   1980
cacatctttt acttttaacg cttttgttgc cgcaacattc tttccttcag aatcctgcgt   2040
tttagacacc attccaaacg tatctttagt tgcaatatca attagcgtct tttcatttaa   2100
cgaattcaat ttagtaacaa tagcttcggc atcggcttga ttggtgataa tcttattctc   2160
tagattgtaa tcaacagaaa aatctacata atcgccatcg cctaatttgt ctaattgtgt   2220
atttacaaga ttatacaact tttctgcggc tgcatctcga tctgctttct tattcgctga   2280
tttaggtgct acttctccta ccacaccatc attgaaactg accgtaatct taccaatact   2340
attatcttta agtccatctt gtaattgttt gacagccttt ttccaatcat tcttaaccac   2400
cgtatagcct tgtgtaccag tggttgcagc aaatacaggt gcagcagcgc taacagtaga   2460
tacagcagaa gcagcaactg gagcaacagc aagtaaagca gcagcagcag cgctaacgat   2520
tcttaaattt ttcttcataa tatctccttt taaattcaat gtttcatcca tattttacac   2580
atttcacagt ttttttcata gagatatggg caaaaaaaca tcttttttta tttctacttt   2640
```

ttattttctg cttttttgtg ctaacttata acaaaagcat actaagagaa gtgtaaaact 2700
attagatttc tttttcctcc gatcatatga tcggaggaaa aagaagtcta atagatcttc 2760
aatttgatca ataaagctac catctcgctt ttgccaatgg cgccattgtg caccataaac 2820
gtcgcctaaa ttaccatatt ttttggcgaa gttctcatca tcaaggatac gtcgatcaaa 2880 ttttttttaat tcagcttgat aaattttatt aaattccgga tcactttgac ttcgtaaacc 2940
aaaatcagtc atatcaggac cagtatattc atcactgtta acccaatttt taaatgccca 3000
ctcatcccaa atatgatttt tatgttctaa taaaaaacga atattagtgt cccctcgtaa 3060
gaaccatagg agttcacttt taattaaacc gaatggaacc tttttagtgg ttaaaattgg 3120
aaaccctttt gataagtcaa agcgcatttg agcaccaagg ccggcc 3166

<210> SEQ ID NO 23
<211> LENGTH: 3667
<212> TYPE: DNA
<213> ORGANISM: Artificial Sequence
<220> FEATURE:
<223> OTHER INFORMATION: Polynucleotide for Lactobacillus integration

<400> SEQUENCE: 23
ggccggcccg ggcttgtcag gggactcatt aatgcggccc gtggtatgat caattaaatc 60
attgatggca aaaatgttta tccaacgact tggagatttt tcaacgatca agggggagtt 120
tcatatgacc gaatttttat gggcacagga tcgcaatggc attatcggca aggatggcca 180
cttgccttgg catctgccag acgatttgca ttattttcgg gcacaaacgg tgggcaaaat 240
catggttgtg ggtcggcgta cctacgaaag ctttcctaag cggccgctgc ctgagcgcac 300
gaatgttgtc ttgacccatc aagccgatta tcaggcgccg gggctgtgg tgctgcatga 360 tgtccccgag gtcttcgctt acgccaagca gcaccctgac caagatctcg ttatcgcagg 420
cggcgcacaa atctttacag cctttaaaga tgacgttaga tctattagac ttctttttcc 480
tccgatcata tgatcggagg aaaaagaaat ctaatagttt tacacttctc ttagtatgct 540
tttgttataa gttagcacaa aaaagcagaa aataaaaagt agaaataaaa aaagatgttt 600
ttttgcccat atctctatga aaaaaactgt gaaatgtgta aaatatggat gaaacattga 660
atttaaaagg agatattatg aagaaaaatt taagaatcgt tagcgctgct gctgctgctt 720
tacttgctgt tgctccagtt gctgcttctg ctgtatctac tgttagcgct gctgcacctg 780
tatttgctgc aaccactggt acacaaggct atacggtggt taagaatgat tggaaaaagg 840
ctgtcaaaca attacaagat ggacttaaag ataatagtat tggtaagatt acggtcagtt 900
tcaatgatgg tgtggtagga gaagtagcac ctaaatcagc gaataagaaa gcagatcgag 960
atgcagccgc agaaaagttg tataatcttg taaatacaca attagacaaa ttaggcgatg 1020
gcgattatgt agatttttct gttgattaca atctagagaa taagattatc accaatcaag 1080
ccgatgccga agctattgtt actaaattga attcgttaaa tgaaaagacg ctaattgata 1140
ttgcaactaa agatacgttt ggaatggtgt ctaaaacgca ggattctgaa ggaaagaatg 1200
ttgcggcaac aaaagcgtta aaagtaaaag atgtggcaac ttttggctta aagagtggag 1260
gtagtgaaga taccggatat gttgtcgaaa tgaaagcggg tgctgttgaa gataagtatg 1320
gtaaagtagg tgattctaca gctggtattg caatcaatct tccatcaaca ggtttagaat 1380
atgcaggcaa aggaacaact attgatttca acaaaaccct taaagttgat gtaactggtg 1440
gtagtacacc gagtgcagtt gccgtaagtg ggtttgtgac taaagatgat acagatttag 1500

-continued

```
catcaaatac taatggtaag tcagctactt tgccagtagt tgttactgtt cctaatgttg   1560
ctgagccaac tgtagccagc gtaagcaaga gaattatgca caacgcatac tactacgaca   1620
aggacgctaa gcgtgttggt actgacagcg ttaagcgtta caactcagta agcgtattgc   1680
caaacactac tactatcaac ggtaagactt actaccaagt agttgaaaac ggtaaggctg   1740
ttgacaagta catcaacgct gcaaacatcg atggtactaa gcgtactttg aagcacaacg   1800
cttacgttta cgcatcatca aagaagcgtg ctaacaaggt tgtattgaag aagggtgaag   1860
ttgtaactac ttacggtgct tcatacacat tcaagaacgg ccaaaagtac tacaagatcg   1920
gtgacaacac tgacaagact tacgttaagg ttgcaaactt tagataataa gatcttatta   1980
agattaccgt tatccgtgaa aaacgagtgg tagcaattgc taaataacaa aaagagtatg   2040
agtttttgct catactcttt ttgttatttg tgcaaatacc gctctacttg tataattaga   2100
acaagtatat aaggaaagta gccgaatatg tttaaaatta ttgttgaatt attcttatta   2160
gtaattattt cagctgctca attacgccat ttattagagt gaggacaagc cctaatgaca   2220
aacaacaaac tgcacttgct tgaatcagaa catgtgttgt gctacggtta ctgtagaatt   2280
catttttaaa aaggggaata tcaggctttc gcatagcaag ctgacggcct aaggggggatt   2340
tatatggcta gttttcaatc atttgggata ccaggacagc tggaagtcat caaaaaagca   2400
cttgatcacg tgcgagtcgg tgtggtaatt acagatcccg cacttgaaga taatcctatt   2460
gtctacgtaa atcaaggctt tgttcaaatg accggctacg agaccgagga aattttagga   2520
aagaacgcac gcttcttaca ggaaatttta ggaaagaacg cacgcttctt acaggggaaa   2580
cacacagatc ctgcagaagt ggacaacatc agaaccgctt tacaaaataa agaaccggtc   2640
accgttcaga tccaaaacta caaaaaagac ggaacgatgt tctggaatga attaaatatt   2700
gatccaatgg aaatagagga taaaacgtat tttgtcggaa ttcagaatga tatcaccaag   2760
caaaaagaat atgaaaagct tctcgaggat tccctcacgg aaattactgc actttcaact   2820
cctattgtcc cgattcgcaa tggcatttcg gctcttccgc tagtcggaaa cctgacagag   2880
gagcgattta attccatcgt ttgcacattg acgaatatct tatcaacatc caaagatgat   2940
tatttgatca ttgatttatc cggattggcc caagtgaacg aacaaacggc cgaccaaatt   3000
ttcaagctga gccatttgct gaaattgacc ggaactgagt taatcattac tggcattaag   3060
cctgaattgg ctatgaaaat gaataaactg gatgccaatt tttcgtcgct gaaaacatat   3120
tcaaatgtaa aggatgccgt taaagtgctt ccgattatgt aaaaagatcc cgctcaccca   3180
gctggatctt tcagatatct cattttcccg gcaccgtgat caccgtatcg catgatcgct   3240
attttcttga taaagtggcc gatcagctgc tgatcttcaa tggcaacggc cagattgacc   3300
gcgctgtggg tgaattttcc gattacctgg ctaagcaagc cgcgcaaccg acgacgccaa   3360
aagctaagcc tgtcgcaacc aaaccggcac cggaaaaagt tgcgccgaaa gcgaagtcga   3420
aactcacata cgctgaaaaa atagagtatg ataaactgca acaagaactc gatgaactcg   3480
acgagcgctt ggccaaagta aaggcggaaa tggccgatgt caacggcgaa gattacgtta   3540
agttaggtga tcttcaggca aagattgaca aaatcaacca gacgattgac aaaaaattcg   3600
accggttcgc cgagctggat caatatgtat gagcaataaa cgatagaagg ggaaagacgg   3660
tttaaac                                                             3667
```

<210> SEQ ID NO 24
<211> LENGTH: 3667
<212> TYPE: DNA
<213> ORGANISM: Artificial Sequence
<220> FEATURE:
<223> OTHER INFORMATION: Polynucleotide for Lactobacillus integration

<400> SEQUENCE: 24
gtttaaaccg tctttcccct tctatcgttt attgctcata catattgatc cagctcggcg 60
aaccggtcga attttttgtc aatcgtctgg ttgattttgt caatctttgc ctgaagatca 120
cctaacttaa cgtaatcttc gccgttgaca tcggccattt ccgcctttac tttggccaag 180
cgctcgtcga gttcatcgag ttcttgttgc agtttatcat actctatttt ttcagcgtat 240
gtgagtttcg acttcgcttt cggcgcaact ttttccggtg ccggtttggt tgcgacaggc 300
ttagcttttg gcgtcgtcgg ttgcgcggct tgcttagcca ggtaatcgga aaattcaccc 360
acagcgcggt caatctggcc gttgccattg aagatcagca gctgatcggc cactttatca 420
agaaaatagc gatcatgcga tacggtgatc acggtgccgg gaaaatgaga tatctgaaag 480
atccagctgg gtgagcggga tctttttaca taatcggaag cactttaacg gcatccttta 540
catttgaata tgttttcagc gacgaaaaat tggcatccag tttattcatt ttcatagcca 600
attcaggctt aatgccagta atgattaact cagttccggt caatttcagc aaatggctca 660
gcttgaaaat ttggtcggcc gtttgttcgt tcacttgggc caatccggat aaatcaatga 720
tcaaataatc atctttggat gttgataaga tattcgtcaa tgtgcaaacg atggaattaa 780
atcgctcctc tgtcaggttt ccgactagcg gaagagccga aatgccattg cgaatcggga 840
caataggagt tgaaagtgca gtaatttccg tgagggaatc ctcgagaagc ttttcatatt 900
ctttttgctt ggtgatatca ttctgaattc cgacaaaata cgttttatcc tctatttcca 960
ttggatcaat atttaattca ttccagaaca tcgttccgtc ttttttgtag ttttggatct 1020
gaacggtgac cggttcttta ttttgtaaag cggttctgat gttgtccact tctgcaggat 1080
ctgtgtgttt cccctgtaag aagcgtgcgt tctttcctaa aatttcctgt aagaagcgtg 1140
cgttctttcc taaaatttcc tcggtctcgt agccggtcat ttgaacaaag ccttgattta 1200
cgtagacaat aggattatct tcaagtgcgg gatctgtaat taccacaccg actcgcacgt 1260
gatcaagtgc tttttttgatg acttccagct gtcctggtat cccaaatgat tgaaaactag 1320
ccatataaat ccccccttagg ccgtcagctt gctatgcgaa agcctgatat tcccctttttt 1380
aaaaatgaat tctacagtaa ccgtagcaca acacatgttc tgattcaagc aagtgcagtt 1440
tgttgtttgt cattagggct tgtcctcact ctaataaatg gcgtaattga gcagctgaaa 1500
taattactaa taagaataat tcaacaataa ttttaaacat attcggctac tttccttata 1560
tacttgttct aattatacaa gtagagcggt atttgcacaa ataacaaaaa gagtatgagc 1620
aaaaactcat actcttttg ttatttagca attgctacca ctcgtttttc acggataacg 1680
gtaatcttaa taagatctta ttatctaaag tttgcaacct taacgtaagt cttgtcagtg 1740
ttgtcaccga tcttgtagta cttttggccg ttcttgaatg tgtatgaagc accgtaagta 1800
gttacaactt cacccttctt caatacaacc ttgttagcac gcttctttga tgatgcgtaa 1860
acgtaagcgt tgtgcttcaa agtacgctta gtaccatcga tgtttgcagc gttgatgtac 1920
ttgtcaacag ccttaccgtt ttcaactact tggtagtaag tcttaccgtt gatagtagta 1980
gtgtttggca atacgcttac tgagttgtaa cgcttaacgc tgtcagtacc aacacgctta 2040
gcgtccttgt cgtagtagta tgcgttgtgc ataattctct tgcttacgct ggctacagtt 2100
ggctcagcaa cattaggaac agtaacaact actggcaaag tagctgactt accattagta 2160
tttgatgcta aatctgtatc atctttagtc acaaacccac ttacggcaac tgcactcggt 2220
gtactaccac cagttacatc aactttaagg gttttgttga aatcaatagt tgttcctttg 2280
cctgcatatt ctaaacctgt tgatggaaga ttgattgcaa taccagctgt agaatcacct 2340
actttaccat acttatcttc aacagcaccc gctttcattt cgacaacata tccggtatct 2400
tcactacctc cactctttaa gccaaaagtt gccacatctt ttacttttaa cgcttttgtt 2460
gccgcaacat tctttccttc agaatcctgc gttttagaca ccattccaaa cgtatcttta 2520
gttgcaatat caattagcgt cttttcattt aacgaattca atttagtaac aatagcttcg 2580
gcatcggctt gattggtgat aatcttattc tctagattgt aatcaacaga aaaatctaca 2640
taatcgccat cgcctaattt gtctaattgt gtatttacaa gattatacaa cttttctgcg 2700
gctgcatctc gatctgcttt cttattcgct gatttaggtg ctacttctcc taccacacca 2760
tcattgaaac tgaccgtaat cttaccaata ctattatctt taagtccatc ttgtaattgt 2820
ttgacagcct tttccaatc attcttaacc accgtatagc cttgtgtacc agtggttgca 2880
gcaaatacag gtgcagcagc gctaacagta gatacagcag aagcagcaac tggagcaaca 2940
gcaagtaaag cagcagcagc agcgctaacg attcttaaat ttttcttcat aatatctcct 3000
tttaaattca atgtttcatc catattttac acatttcaca gttttttca tagagatatg 3060 ggcaaaaaaa catctttttt tatttctact ttttatttc tgcttttttg tgctaactta 3120
taacaaaagc atactaagag aagtgtaaaa ctattagatt tctttttcct ccgatcatat 3180
gatcggagga aaaagaagtc taatagatct aacgtcatct ttaaaggctg taaagatttg 3240
tgcgccgcct gcgataacga gatcttggtc agggtgctgc ttggcgtaag cgaagacctc 3300
ggggacatca tgcagcacca cagcccccgg cgcctgataa tcggcttgat gggtcaagac 3360
aacattcgtg cgctcaggca gcggccgctt aggaaagctt tcgtaggtac gccgacccac 3420
aaccatgatt ttgcccaccg tttgtgcccg aaaataatgc aaatcgtctg gcagatgcca 3480
aggcaagtgg ccatccttgc cgataatgcc attgcgatcc tgtgcccata aaaattcggt 3540
catatgaaac tccccccttga tcgttgaaaa atctccaagt cgttggataa acatttttgc 3600
catcaatgat ttaattgatc ataccacggg ccgcattaat gagtcccctg acaagcccgg 3660
gccggcc 3667

<210> SEQ ID NO 25
<211> LENGTH: 3166
<212> TYPE: DNA
<213> ORGANISM: Artificial Sequence
<220> FEATURE:
<223> OTHER INFORMATION: Polynucleotide for Lactobacillus integration

<400> SEQUENCE: 25
ggccggcctt ggtgctcaaa tgcgctttga cttatcaaaa gggtttccaa ttttaaccac 60
taaaaaggtt ccattcggtt taattaaaag tgaactccta tggttcttac gaggggacac 120
taatattcgt tttttattag aacataaaaa tcatatttgg gatgagtggg catttaaaaa 180
ttgggttaac agtgatgaat atactggtcc tgatatgact gattttggtt tacgaagtca 240
aagtgatccg gaatttaata aaatttatca agctgaatta aaaaaatttg atcgacgtat 300
ccttgatgat gagaacttcg ccaaaaaata tggtaattta ggcgacgttt atggtgcaca 360
atggcgccat tggcaaaagc gagatggtag ctttattgat caaattgaag atctattaga 420
cttctttttc ctccgatcat atgatcggag gaaaaagaaa tctaatagtt ttacacttct 480
cttagtatgc ttttgttata agttagcaca aaaaagcaga aaataaaaag tagaaataaa 540
aaaagatgtt tttttgccca tatctctatg aaaaaaactg tgaaatgtgt aaaatatgga 600

-continued

```
tgaaacattg aatttaaaag gagatattat gaagaaaaat ttaagaatcg ttagcgctgc    660
tgctgctgct ttacttgctg ttgctccagt tgctgcttct gctgtatcta ctgttagcgc    720
tgctgcacct gtatttgctg caaccactgg tacacaaggc tatacggtgg ttaagaatga    780
ttggaaaaag gctgtcaaac aattacaaga tggacttaaa gataatagta ttggtaagat    840
tacggtcagt ttcaatgatg gtgtggtagg agaagtagca cctaaatcag cgaataagaa    900
agcagatcga gatgcagccg cagaaaagtt gtataatctt gtaaatacac aattagacaa    960
attaggcgat ggcgattatg tagatttttc tgttgattac aatctagaga ataagattat   1020
caccaatcaa gccgatgccg aagctattgt tactaaattg aattcgttaa atgaaaagac   1080
gctaattgat attgcaacta aagatacgtt tggaatggtg tctaaaacgc aggattctga   1140
aggaaagaat gttgcggcaa caaaagcgtt aaaagtaaaa gatgtggcaa cttttggctt   1200
aaagagtgga ggtagtgaag ataccggata tgttgtcgaa atgaaagcgg gtgctgttga   1260
agataagtat ggtaaagtag gtgattctac agctggtatt gcaatcaatc ttccatcaac   1320
aggtttagaa tatgcaggca aaggaacaac tattgatttc aacaaaaccc ttaaagttga   1380
tgtaactggt ggtagtacac cgagtgcagt tgccgtaagt gggtttgtga ctaaagatga   1440
tacagattta gcatcaaata ctaatggtaa gtcagctact ttgccagtag ttgttactgt   1500
tcctaatgtt gctgagccaa ctgtagccag cgtaagcaag agaattatgc acaacgcata   1560
ctactacgac aaggacgcta agcgtgttgg tactgacagc gttaagcgtt acaactcagt   1620
aagcgtattg ccaaacacta ctactatcaa cggtaagact tactaccaag tagttgaaaa   1680
cggtaaggct gttgacaagt acatcaacgc tgcaaacatc gatggtacta agcgtacttt   1740
gaagcacaac gcttacgttt acgcatcatc aaagaagcgt gctaacaagg ttgtattgaa   1800
gaagggtgaa gttgtaacta cttacggtgc ttcatacaca ttcaagaacg gccaaaagta   1860
ctacaagatc ggtgacaaca ctgacaagac ttacgttaag gttgcaaact ttagataata   1920
agatcttatt aagattaccg ttatccgtga aaaacgagtg gtagcaattg ctaaataaca   1980
aaaagagtat gagtttttgc tcatactctt tttgttattt gtgcaaatac cgctctactt   2040
gtataattag aacaagtata taaggaaagt agccgaatat gtttaaaatt attgttgaat   2100
tattcttatt agtaattatt tcagctgctc aattacgcca tttattagag ggcgcgcctg   2160
aggacaagcc ctaatgacaa acaacaaact gcacttgctt gaatcagaac atgtgttgtg   2220
ctacggttac tgtagaattc atttttaaaa aggggaatat caggctttcg catagcaagc   2280
tgacggccta agggggattt atatggctag ttttcaatca tttgggatac caggacagct   2340
ggaagtcatc aaaaaagcac ttgatcacgt gcgagtcggt gtggtaatta cagatcccgc   2400
acttgaagat aatcctattg tctacgtaaa tcaaggcttt gttcaaatga ccggctacga   2460
gaccgaggaa attttaggaa agaacgcacg cttcttacag gaaattttag gaaagaacgc   2520
acgcttctta caggggaaac acacagatcc tgcagaagtg gacaacatca gaaccgcttt   2580
acaaaataaa gaaccggtca ccgttcagat ccaaaactac aaaaaagacg gaacgatgtt   2640
ctggaatgaa ttaaatattg atccaatgga aatagaggat aaaacgtatt ttgtcggaat   2700
tcagaatgat atcaccaagc aaaaagaata tgaaaagctt ctcgaggatt ccctcacgga   2760
aattactgca ctttcaactc ctattgtccc gattcgcaat ggcatttcgg ctcttccgct   2820
agtcggaaac ctgacagagg agcgatttaa ttccatcgtt tgcacattga cgaatatctt   2880
atcaacatcc aaagatgatt atttgatcat tgatttatcc ggattggccc aagtgaacga   2940
```

-continued

```
acaaacggcc gaccaaattt tcaagctgag ccatttgctg aaattgaccg gaactgagtt   3000

aatcattact ggcattaagc ctgaattggc tatgaaaatg aataaactgg atgccaattt   3060

ttcgtcgctg aaaacatatt caaatgtaaa ggatgccgtt aaagtgcttc cgattatgta   3120

aaaagatccc gctcacccag ctggatcttt cagatatcgt ttaaac                  3166
```

<210> SEQ ID NO 26
<211> LENGTH: 3166
<212> TYPE: DNA
<213> ORGANISM: Artificial Sequence
<220> FEATURE:
<223> OTHER INFORMATION: Polynucleotide for Lactobacillus integration

<400> SEQUENCE: 26

```
gtttaaacga tatctgaaag atccagctgg gtgagcggga tctttttaca taatcggaag     60

cactttaacg gcatccttta catttgaata tgttttcagc gacgaaaaat tggcatccag    120

tttattcatt ttcatagcca attcaggctt aatgccagta atgattaact cagttccggt    180

caatttcagc aaatggctca gcttgaaaat ttggtcggcc gtttgttcgt tcacttgggc    240

caatccggat aaatcaatga tcaaataatc atctttggat gttgataaga tattcgtcaa    300

tgtgcaaacg atggaattaa atcgctcctc tgtcaggttt ccgactagcg gaagagccga    360

aatgccattg cgaatcggga caataggagt tgaaagtgca gtaatttccg tgagggaatc    420

ctcgagaagc ttttcatatt ctttttgctt ggtgatatca ttctgaattc cgacaaaata    480

cgttttatcc tctatttcca ttggatcaat atttaattca ttccagaaca tcgttccgtc    540

tttttgtag ttttggatct gaacggtgac cggttcttta ttttgtaaag cggttctgat     600

gttgtccact tctgcaggat ctgtgtgttt cccctgtaag aagcgtgcgt tctttcctaa    660

aatttcctgt aagaagcgtg cgttctttcc taaaatttcc tcggtctcgt agccggtcat    720

ttgaacaaag ccttgattta cgtagacaat aggattatct tcaagtgcgg gatctgtaat    780

taccacaccg actcgcacgt gatcaagtgc tttttttgatg acttccagct gtcctggtat   840

cccaaatgat tgaaaactag ccatataaat ccccccttagg ccgtcagctt gctatgcgaa   900

agcctgatat tccccttttt aaaaatgaat tctacagtaa ccgtagcaca acacatgttc    960

tgattcaagc aagtgcagtt tgttgtttgt cattagggct tgtcctcagg cgcgccctct   1020

aataaatggc gtaattgagc agctgaaata attactaata agaataattc aacaataatt   1080

ttaaacatat tcggctactt tccttatata cttgttctaa ttatacaagt agagcggtat   1140

ttgcacaaat aacaaaaaga gtatgagcaa aaactcatac tctttttgtt atttagcaat   1200

tgctaccact cgtttttcac ggataacggt aatcttaata agatcttatt atctaaagtt   1260

tgcaacctta acgtaagtct tgtcagtgtt gtcaccgatc ttgtagtact tttggccgtt   1320

cttgaatgtg tatgaagcac cgtaagtagt tacaacttca cccttcttca atacaacctt   1380

gttagcacgc ttctttgatg atgcgtaaac gtaagcgttg tgcttcaaag tacgcttagt   1440

accatcgatg tttgcagcgt tgatgtactt gtcaacagcc ttaccgtttt caactacttg   1500

gtagtaagtc ttaccgttga tagtagtagt gtttggcaat acgcttactg agttgtaacg   1560

cttaacgctg tcagtaccaa cacgcttagc gtccttgtcg tagtagtatg cgttgtgcat   1620

aattctcttg cttacgctgg ctacagttgg ctcagcaaca ttaggaacag taacaactac   1680

tggcaaagta gctgacttac cattagtatt tgatgctaaa tctgtatcat ctttagtcac   1740

aaacccactt acggcaactg cactcggtgt actaccacca gttacatcaa ctttaagggt   1800

tttgttgaaa tcaatagttg ttcctttgcc tgcatattct aaacctgttg atggaagatt   1860
```

```
gattgcaata ccagctgtag aatcacctac tttaccatac ttatcttcaa cagcacccgc   1920

tttcatttcg acaacatatc cggtatcttc actacctcca ctctttaagc caaaagttgc   1980

cacatctttt acttttaacg cttttgttgc cgcaacattc tttccttcag aatcctgcgt   2040

tttagacacc attccaaacg tatctttagt tgcaatatca attagcgtct tttcatttaa   2100

cgaattcaat ttagtaacaa tagcttcggc atcggcttga ttggtgataa tcttattctc   2160

tagattgtaa tcaacagaaa aatctacata atcgccatcg cctaatttgt ctaattgtgt   2220

atttacaaga ttatacaact tttctgcggc tgcatctcga tctgctttct tattcgctga   2280

tttaggtgct acttctccta ccacaccatc attgaaactg accgtaatct taccaatact   2340

attatcttta agtccatctt gtaattgttt gacagccttt ttccaatcat tcttaaccac   2400

cgtatagcct tgtgtaccag tggttgcagc aaatacaggt gcagcagcgc taacagtaga   2460

tacagcagaa gcagcaactg gagcaacagc aagtaaagca gcagcagcag cgctaacgat   2520

tcttaaattt ttcttcataa tatctccttt taaattcaat gtttcatcca tattttacac   2580

atttcacagt ttttttcata gagatatggg caaaaaaaca tcttttttta tttctacttt   2640

ttattttctg ctttttttgtg ctaacttata acaaaagcat actaagagaa gtgtaaaact   2700

attagatttc tttttcctcc gatcatatga tcggaggaaa aagaagtcta atagatcttc   2760

aatttgatca ataaagctac catctcgctt ttgccaatgg cgccattgtg caccataaac   2820

gtcgcctaaa ttaccatatt ttttggcgaa gttctcatca tcaaggatac gtcgatcaaa   2880

ttttttttaat tcagcttgat aaattttatt aaattccgga tcactttgac ttcgtaaacc   2940

aaaatcagtc atatcaggac cagtatattc atcactgtta acccaatttt taaatgccca   3000

ctcatcccaa atatgatttt tatgttctaa taaaaaacga atattagtgt cccctcgtaa   3060

gaaccatagg agttcacttt taattaaacc gaatggaacc tttttagtgg ttaaaattgg   3120

aaacccttttt gataagtcaa agcgcatttg agcaccaagg ccggcc                  3166
```

<210> SEQ ID NO 27
<211> LENGTH: 3720
<212> TYPE: DNA
<213> ORGANISM: Artificial Sequence
<220> FEATURE:
<223> OTHER INFORMATION: Polynucleotide for Lactobacillus integration

<400> SEQUENCE: 27

```
ggccggccgg tgaagtaatg attgaatatg tttgggcaga agataaagaa aaaaatattg     60

gcttgaatgg acatttacca tggtatttgc cggctgatat gaagcatttt aaagaagtaa    120

caattaatca tccaataatt atgggaagaa aaacatttga aagttttcct aatttgttac    180

ctaaaagaaa acatattgtt ttaactcata atgaagagct aaaaaataaa tatcaaaata    240

atgatcaagt gactatttta cccacagttg aagatttaca taattttgtg gcagaacatc    300

aagatgagcg gatgtgtgca attggtggag tgtcgatttt taacgcttta atggaccaag    360

tagaagtatt agaaaaaacg gagatagatg cgatttttga agcagatact aaaatgcctg    420

aaattgatta tagccgtttt aatttagtag cagatcatta gacttctttt tcctccgatc    480

atatgatcgg aggaaaaaga aatctaatag ttttacactt ctcttagtat gcttttgtta    540

taagttagca caaaaaagca gaaaataaaa agtagaaata aaaaaagatg tttttttgcc    600

catatctcta tgaaaaaaac tgtgaaatgt gtaaaatatg gatgaaacat tgaatttaaa    660

aggagatatt atgaagaaaa atttaagaat cgttagcgct gctgctgctg ctttacttgc    720
```

-continued

```
tgttgctcca gttgctgctt ctgctgtatc tactgttagc gctgctgcac ctgtatttgc    780

tgcaaccact ggtacacaag gctatacggt ggttaagaat gattggaaaa aggctgtcaa    840

acaattacaa gatggactta aagataatag tattggtaag attacggtca gtttcaatga    900

tggtgtggta ggagaagtag cacctaaatc agcgaataag aaagcagatc gagatgcagc    960

cgcagaaaag ttgtataatc ttgtaaatac acaattagac aaattaggcg atggcgatta   1020

tgtagatttt tctgttgatt acaatctaga gaataagatt atcaccaatc aagccgatgc   1080

cgaagctatt gttactaaat tgaattcgtt aaatgaaaag acgctaattg atattgcaac   1140

taaagatacg tttggaatgg tgtctaaaac gcaggattct gaaggaaaga atgttgcggc   1200

aacaaaagcg ttaaaagtaa aagatgtggc aacttttggc ttaaagagtg gaggtagtga   1260

agataccgga tatgttgtcg aaatgaaagc gggtgctgtt gaagataagt atggtaaagt   1320

aggtgattct acagctggta ttgcaatcaa tcttccatca acaggtttag aatatgcagg   1380

caaaggaaca actattgatt tcaacaaaac ccttaaagtt gatgtaactg gtggtagtac   1440

accgagtgca gttgccgtaa gtgggtttgt gactaaagat gatacagatt tagcatcaaa   1500

tactaatggt aagtcagcta ctttgccagt agttgttact gttcctaatg ttgctgagcc   1560

aactgtagcc agcgtaagca agagaattat gcacaacgca tactactacg acaaggacgc   1620

taagcgtgtt ggtactgaca gcgttaagcg ttacaactca gtaagcgtat tgccaaacac   1680

tactactatc aacggtaaga cttactacca agtagttgaa aacggtaagg ctgttgacaa   1740

gtacatcaac gctgcaaaca tcgatggtac taagcgtact ttgaagcaca acgcttacgt   1800

ttacgcatca tcaaagaagc gtgctaacaa ggttgtattg aagaagggtg aagttgtaac   1860

tacttacggt gcttcataca cattcaagaa cggccaaaag tactacaaga tcggtgacaa   1920

cactgacaag acttacgtta aggttgcaaa ctttagataa taagatctta ttaagattac   1980

cgttatccgt gaaaaacgag tggtagcaat tgctaaataa caaaaagagt atgagttttt   2040

gctcatactc tttttgttat ttgtgcaaat accgctctac ttgtataatt agaacaagta   2100

tataaggaaa gtagccgaat atgtttaaaa ttattgttga attattctta ttagtaatta   2160

tttcagctgc tcaattacgc catttattag agtgaggaca agccctaatg acaaacaaca   2220

aactgcactt gcttgaatca gaacatgtgt tgtgctacgg ttactgtaga attcattttt   2280

aaaaagggga atatcaggct ttcgcatagc aagctgacgg cctaaggggg atttatatgg   2340

ctagttttca atcatttggg ataccaggac agctggaagt catcaaaaaa gcacttgatc   2400

acgtgcgagt cggtgtggta attacagatc ccgcacttga agataatcct attgtctacg   2460

taaatcaagg ctttgttcaa atgaccggct acgagaccga ggaaatttta ggaaagaacg   2520

cacgcttctt acaggaaatt ttaggaaaga acgcacgctt cttacagggg aaacacacag   2580

atcctgcaga agtggacaac atcagaaccg ctttacaaaa taaagaaccg gtcaccgttc   2640

agatccaaaa ctacaaaaaa gacggaacga tgttctggaa tgaattaaat attgatccaa   2700

tggaaataga ggataaaacg tattttgtcg gaattcagaa tgatatcacc aagcaaaaag   2760

aatatgaaaa gcttctcgag gattccctca cggaaattac tgcactttca actcctattg   2820

tcccgattcg caatggcatt tcggctcttc cgctagtcgg aaacctgaca gaggagcgat   2880

ttaattccat cgtttgcaca ttgacgaata tcttatcaac atccaaagat gattatttga   2940

tcattgattt atccggattg gcccaagtga acgaacaaac ggccgaccaa attttcaagc   3000

tgagccattt gctgaaattg accggaactg agttaatcat tactggcatt aagcctgaat   3060

tggctatgaa aatgaataaa ctggatgcca atttttcgtc gctgaaaaca tattcaaatg   3120
```

```
taaaggatgc cgttaaagtg cttccgatta tgtaaaaaga tcccgctcac ccagctggat   3180

ctttcagata tccctgatcg cgccattatg ggatttctg gtgggatttt tattgggttt   3240

attttaaata taattgcatc tcaatttaat cattcggcat cagatttatt tgtgattgtc   3300

ttcagttcat cagttttacc aggaatgatt ccatggtttg taattctatt ggctgagtta   3360

agatttagaa gacataatca agatatgatg aaagatcacc cgttcaaatt gccgttatat   3420

ccattttcta attacttcgc atttttaatg ctgttagtaa ttgttatctt tatgtttatt   3480

aatccagata ctagaatttc agtaattacc ggagcattgg tattaattgt ggctacaatt   3540

gtttatttag ttagacataa agatgaattt agtaaaaata attaatgatt aagaagtctt   3600

gaaatttcag ggctttttat ttttaccaaa tactaaatat tgatacttgc attatcaaaa   3660

atactagatc tatggtatct taaaaagaaa tgatacttaa agggtgagat aagtttaaac   3720
```

<210> SEQ ID NO 28
<211> LENGTH: 3720
<212> TYPE: DNA
<213> ORGANISM: Artificial Sequence
<220> FEATURE:
<223> OTHER INFORMATION: Polynucleotide for Lactobacillus integration

<400> SEQUENCE: 28

```
gtttaaactt atctcaccct ttaagtatca tttcttttta agataccata gatctagtat     60

ttttgataat gcaagtatca atatttagta tttggtaaaa ataaaaagcc ctgaaatttc    120

aagacttctt aatcattaat tatttttact aaattcatct ttatgtctaa ctaaataaac    180

aattgtagcc acaattaata ccaatgctcc ggtaattact gaaattctag tatctggatt    240

aataaacata aagataacaa ttactaacag cattaaaaat gcgaagtaat tagaaaatgg    300

atataacggc aatttgaacg ggtgatcttt catcatatct tgattatgtc ttctaaatct    360

taactcagcc aatagaatta caaaccatgg aatcattcct ggtaaaactg atgaactgaa    420

gacaatcaca aataaatctg atgccgaatg attaaattga gatgcaatta tatttaaaat    480

aaacccaata aaaatcccac cagaaatccc cataatggcg cgatcaggga tatctgaaag    540

atccagctgg gtgagcggga tctttttaca taatcggaag cactttaacg gcatccttta    600

catttgaata tgttttcagc gacgaaaaat tggcatccag tttattcatt ttcatagcca    660

attcaggctt aatgccagta atgattaact cagttccggt caatttcagc aaatggctca    720

gcttgaaaat ttggtcggcc gtttgttcgt tcacttgggc caatccggat aaatcaatga    780

tcaaataatc atctttggat gttgataaga tattcgtcaa tgtgcaaacg atggaattaa    840

atcgctcctc tgtcaggttt ccgactagcg gaagagccga aatgccattg cgaatcggga    900

caataggagt tgaaagtgca gtaatttccg tgagggaatc ctcgagaagc ttttcatatt    960

ctttttgctt ggtgatatca ttctgaattc cgacaaaata cgttttatcc tctatttcca   1020

ttggatcaat atttaattca ttccagaaca tcgttccgtc ttttttgtag ttttggatct   1080

gaacggtgac cggttcttta ttttgtaaag cggttctgat gttgtccact tctgcaggat   1140

ctgtgtgttt cccctgtaag aagcgtgcgt tctttcctaa aatttcctgt aagaagcgtg   1200

cgttctttcc taaaatttcc tcggtctcgt agccggtcat ttgaacaaag ccttgattta   1260

cgtagacaat aggattatct tcaagtgcgg gatctgtaat taccacaccg actcgcacgt   1320

gatcaagtgc ttttttgatg acttccagct gtcctggtat cccaaatgat tgaaaactag   1380

ccatataaat ccccccttagg ccgtcagctt gctatgcgaa agcctgatat tcccctttt   1440
```

-continued

```
aaaaatgaat tctacagtaa ccgtagcaca acacatgttc tgattcaagc aagtgcagtt   1500
tgttgtttgt cattagggct tgtcctcact ctaataaatg gcgtaattga gcagctgaaa   1560
taattactaa taagaataat tcaacaataa ttttaaacat attcggctac tttccttata   1620
tacttgttct aattatacaa gtagagcggt atttgcacaa ataacaaaaa gagtatgagc   1680
aaaaactcat actcttttg ttatttagca attgctacca ctcgttttc acggataacg   1740
gtaatcttaa taagatctta ttatctaaag tttgcaacct taacgtaagt cttgtcagtg   1800
ttgtcaccga tcttgtagta cttttggccg ttcttgaatg tgtatgaagc accgtaagta   1860
gttacaactt cacccttctt caatacaacc ttgttagcac gcttctttga tgatgcgtaa   1920
acgtaagcgt tgtgcttcaa agtacgctta gtaccatcga tgtttgcagc gttgatgtac   1980
ttgtcaacag ccttaccgtt ttcaactact tggtagtaag tcttaccgtt gatagtagta   2040
gtgtttggca atacgcttac tgagttgtaa cgcttaacgc tgtcagtacc aacacgctta   2100
gcgtccttgt cgtagtagta tgcgttgtgc ataattctct tgcttacgct ggctacagtt   2160
ggctcagcaa cattaggaac agtaacaact actggcaaag tagctgactt accattagta   2220
tttgatgcta aatctgtatc atctttagtc acaaacccac ttacggcaac tgcactcggt   2280
gtactaccac cagttacatc aactttaagg gttttgttga aatcaatagt tgttcctttg   2340
cctgcatatt ctaaacctgt tgatggaaga ttgattgcaa taccagctgt agaatcacct   2400
actttaccat acttatcttc aacagcaccc gctttcattt cgacaacata tccggtatct   2460
tcactacctc cactctttaa gccaaaagtt gccacatctt ttacttttaa cgcttttgtt   2520
gccgcaacat tctttccttc agaatcctgc gttttagaca ccattccaaa cgtatcttta   2580
gttgcaatat caattagcgt cttttcattt aacgaattca atttagtaac aatagcttcg   2640
gcatcggctt gattggtgat aatcttattc tctagattgt aatcaacaga aaaatctaca   2700
taatcgccat cgcctaattt gtctaattgt gtatttacaa gattatacaa cttttctgcg   2760
gctgcatctc gatctgcttt cttattcgct gatttaggtg ctacttctcc taccacacca   2820
tcattgaaac tgaccgtaat cttaccaata ctattatctt taagtccatc ttgtaattgt   2880
ttgacagcct ttttccaatc attcttaacc accgtatagc cttgtgtacc agtggttgca   2940
gcaaatacag gtgcagcagc gctaacagta gatacagcag aagcagcaac tggagcaaca   3000
gcaagtaaag cagcagcagc agcgctaacg attcttaaat ttttcttcat aatatctcct   3060
tttaaattca atgtttcatc catattttac acatttcaca gtttttttca tagagatatg   3120
ggcaaaaaaa catctttttt tatttctact ttttattttc tgcttttttg tgctaactta   3180
taacaaaagc atactaagag aagtgtaaaa ctattagatt tctttttcct ccgatcatat   3240
gatcggagga aaaagaagtc taatgatctg ctactaaatt aaaacggcta taatcaattt   3300
caggcatttt agtatctgct tcaaaaatcg catctatctc cgttttttct aatacttcta   3360
cttggtccat taaagcgtta aaaatcgaca ctccaccaat tgcacacatc cgctcatctt   3420
gatgttctgc cacaaaatta tgtaaatctt caactgtggg taaaatagtc acttgatcat   3480
tattttgata tttatttttt agctcttcat tatgagttaa aacaatatgt tttcttttag   3540
gtaacaaatt aggaaaactt tcaaatgttt ttcttcccat aattattgga tgattaattg   3600
ttacttcttt aaaatgcttc atatcagccg gcaaatacca tggtaaatgt ccattcaagc   3660
caatattttt ttctttatct tctgcccaaa catattcaat cattacttca ccggccggcc   3720
```

COMPOSITIONS COMPRISING RECOMBINANT PROBIOTIC BACTERIA AND METHODS OF USE THEREOF

CROSS REFERENCE TO RELATED APPLICATIONS

This application is a 35 U.S.C. § 371 national phase application from, and claims priority to, International Application No. PCT/US2016/014590, filed Jan. 22, 2016, and published under PCT Article 21(2) in English, which claims priority to and benefit of U.S. Provisional Application Ser. No. 62/107,224, filed Jan. 23, 2015, the contents of which are incorporated by reference herein in their entireties.

STATEMENT OF RIGHTS TO INVENTIONS MADE UNDER FEDERALLY SPONSORED RESEARCH

This invention was made with government support Grant No. 2101BX001183-05A1, awarded by VA and Grant No. ARZT-570410-A-02-139, awarded by USDA. The government has certain rights in the invention.

BACKGROUND OF THE INVENTION

*Clostridium difficile* infection (CDI) is a leading cause of antibiotic-associated diarrhea in humans and animals, including agriculturally relevant animals such as calves, foals, and piglets. In the U.S., 400,000 human cases are diagnosed annually, and its treatment and prevention imposes over $3 billion in healthcare-associated costs.

CDI is precipitated when commensal flora are suppressed following antibiotic treatment. The use of antibiotics can suppress the protective normal microbiota causing susceptibility to infection. Exposure to *C. difficile* spores results in colonization of the host gastrointestinal tract. Current treatments include use of antibiotics, which have the potential to alter the bacterial composition of the gut microbiome. Vaccines are being developed for preventing *C. difficile* disease, but do not protect against *C. difficile* colonization.

At present, effective treatments and preventatives for *Clostridium difficile* infection and colonization are lacking. New methods of treatment are urgently required.

SUMMARY OF THE INVENTION

As described below, the present invention features probiotic bacteria (e.g., *Lactoccocus lactis* and *Lactobacillus acidophilus*) expressing the *Clostridium difficile* surface protein SlpA, or fragment or chimera thereof, and its use in treating or preventing *Clostridium difficile* infection and colonization.

In one aspect, the invention provides an isolated polypeptide having a bacterial secretion signal, *C. difficile* SlpA variable domain, and *Lactobacillus* SlpA cell wall binding domain.

In another aspect, the invention provides an isolated nucleic acid molecule encoding a polypeptide having a bacterial secretion signal, *C. difficile* SlpA variable domain, and *Lactobacillus* SlpA cell wall binding domain.

In still another aspect, the invention provides a vector having a nucleic acid sequence encoding a polypeptide having a bacterial secretion signal, *C. difficile* SlpA variable domain, and *Lactobacillus* SlpA cell wall binding domain.

In yet another aspect, the invention provides an isolated cell (e.g., bacterial cell) containing a nucleic acid molecule encoding a polypeptide having a bacterial secretion signal, *C. difficile* SlpA variable domain, and *Lactobacillus* SlpA cell wall binding domain or a vector having a nucleic acid sequence encoding a polypeptide having a bacterial secretion signal, *C. difficile* SlpA variable domain, and *Lactobacillus* SlpA cell wall binding domain.

In one aspect, the invention provides a method of treating or preventing *Clostridium difficile* infection in a subject, the method involving administering one or more *Lactococcus* or *Lactobacillus* bacterial strains expressing a chimeric SlpA polypeptide to the gut of the subject, where the chimeric SlpA polypeptide has a bacterial secretion signal, *C. difficile* SlpA variable domain, and *Lactobacillus* SlpA cell wall binding domain, thereby treating or preventing *Clostridium difficile* infection in the subject.

In another aspect, the invention provides a method of colonizing the gut of a subject with one or more *Lactococcus* or *Lactobacillus* bacterial strains, the method comprising administering one or more *Lactococcus* or *Lactobacillus* bacterial strains expressing a chimeric SlpA polypeptide to the gut of the subject, where the chimeric SlpA polypeptide comprises a bacterial secretion signal, *C. difficile* SlpA variable domain, and *Lactobacillus* SlpA cell wall binding domain, thereby colonizing the gut of a subject with *Lactococcus* or *Lactobacillus*.

In another aspect, the invention provides a composition (e.g., a therapeutic or pharmaceutical composition) containing an effective amount of one or more *Lactoccocus* or *Lactobacillus* bacterial strains expressing a chimeric SlpA polypeptide, where the chimeric SlpA polypeptide has a bacterial secretion signal, *C. difficile* SlpA variable domain, and *Lactobacillus* SlpA cell wall binding domain.

In still another aspect, the invention provides a kit for treating or preventing *Clostridium difficile* infection in a subject, the kit comprising one or more *Lactoccocus* or *Lactobacillus* bacterial strains expressing a chimeric SlpA polypeptide, where the chimeric SlpA polypeptide has a bacterial secretion signal, *C. difficile* SlpA variable domain, and *Lactobacillus* SlpA cell wall binding domain and optionally directions for the use of the kit (e.g., in the methods of any aspect of the invention).

In yet another aspect, the invention provides kit for colonizing the gut of a subject with *Lactoccocus* or *Lactobacillus*, the kit containing one or more *Lactoccocus* or *Lactobacillus* bacterial strains expressing a chimeric SlpA polypeptide, where the chimeric SlpA polypeptide has a bacterial secretion signal, *C. difficile* SlpA variable domain, and *Lactobacillus* SlpA cell wall binding domain and optionally directions for the use of the kit (e.g., in the methods of any aspect of the invention).

In various embodiments of any of the aspects delineated herein, the SlpA variable domain has the amino acid sequence (SEQ ID NO: 1):

```
AAPVFAATTGTQGYTVVKNDWKKAVKQLQDGLKDNSIGKITVSENDGVVG

EVAPKSANKKADRDAAAEKLYNLVNTQLDKLGDGDYVDFSVDYNLENKII

TNQADAEAIVTKLNSLNEKTLIDIATKDTFGMVSKTQDSEGKNVAATKAL

KVKDVATFGLKSGGSEDTGYVVEMKAGAVEDKYGKVGDSTAGIAINLPST

GLEYAGKGTTIDFNKTLKVDVTGGSTPSAVAVSGFVTKDDTDLA
```

In various embodiments of any of the aspects delineated herein, the SlpA cell wall binding domain is a *Lactobacillus acidophilus* or *Lactobacillus casei* SlpA cell wall binding domain. In certain embodiments, the SlpA cell wall binding domain has the amino acid sequence (SEQ ID NO: 2):

```
SNTNGKSATLPVVVTVPNVAEPTVASVSKRIMHNAYYYDKDAKRVGTDSV

KRYNSVSVLPNTTTINGKTYYQVVENGKAVDKYINAANIDGTKRTLKHNA

YVYASSKKRANKVVLKKGEVVTTYGASYTFKNGQKYYKIGDNTDKTYVKV

ANFR
```

In various embodiments of any of the aspects delineated herein, the bacterial secretion signal is a *Lactococcus, Lactobacillus, Lactobacillus acidophilus*, or *Lactobacillus casei* secretion signal. In certain embodiments, the bacterial secretion signal has the amino acid sequence (SEQ ID NO: 3):

```
MKKNLRIVSAAAAALLAVAPVAASAVSTVSA
```

-continued

```
TAAAGTAGGTGATTCTACAGCTGGTATTGCAATCAATCTTCCATCAACAG

GTTTAGAATATGCAGGCAAAGGAACAACTATTGATTTCAACAAAACCCTT

AAAGTTGATGTAACTGGTGGTAGTACACCGAGTGCAGTTGCCGTAAGTGG

GTTTGTGACTAAAGATGATACAGATTTAGCATCAAATACTAATGGTAAGT

CAGCTACTTTGCCAGTAGTTGTTACTGTTCCTAATGTTGCTGAGCCAACT

GTAGCCAGCGTAAGCAAGAGAATTATGCACAACGCATACTACTACGACAA

GGACGCTAAGCGTGTTGGTACTGACAGCGTTAAGCGTTACAACTCAGTAA

GCGTATTGCCAAACACTACTACTATCAACGGTAAGACTTACTACCAAGTA

GTTGAAAACGGTAAGGCTGTTGACAAGTACATCAACGCTGCAAACATCGA

TGGTACTAAGCGTACTTTGAAGCACAACGCTTACGTTTACGCATCATCAA

AGAAGCGTGCTAACAAGGTTGTATTGAAGAAGGGTGAAGTTGTAACTACT

TACGGTGCTTCATACACATTCAAGAACGGCCAAAAGTACTACAAGATCGG
```

In particular embodiments, the isolated polypeptide has the amino acid sequence (SEQ ID NO: 4):

```
MKKNLRIVSAAAAALLAVAPVAASAVSTVSAAAPVFAATTGIQGYTVVKN    50

DWKKAVKQLQDGLKDNSIGKITVSFNDGVVGEVAPKSANKKADRDAAAEK   100

LYNLVNTQLDKLGDGDYVDFSVDYNLENKIITNQADAEAIVIKLNSLNEK   150

TLIDIATKDTFGMVSKTQDSEGKNVAATKALKVKDVATFGLKSGGSEDTG   200

YVVEMKAGAVEDKYGKVGDSTAGIAINLPSTGLEYAGKGTTIDFNKTLKV   250

DVTGGSTPSAVAVSGFVTKDDTDLASNTNGKSATLPVVVTVPNVAEPTVA   300

SVSKRIMHNAYYYDKDAKRVGTDSVKRYNSVSVLPNTTTINGKTYYQVVE   350

NGKAVDKYINAANIDGTKRTLKHNAYVYASSKKRANKVVLKKGEVVTTYG   400

ASYTFKNGQKYYKIGDNTDKTYVKVANFR*
```

In various embodiments of any of the aspects delineated herein, the isolated nucleic acid molecule contains a sequence optimized for expression in *Lactococcus, Lactococcus lactis, Lactobacillus, Lactobacillus acidophilus*, or *Lactobacillus casei*. In specific embodiments, the isolated nucleic acid has the nucleic acid sequence (SEQ ID NO: 5):

```
GGATCCATGAAGAAAAATTTAAGAATCGTTAGCGCTGCTGCTGCTGCTTT

ACTTGCTGTTGCTCCAGTTGCTGCTTCTGCTGTATCTACTGTTAGCGCTG

CTGCACCTGTATTTGCTGCAACCACTGGTACACAAGGCTATACGGTGGTT

AAGAATGATTGGAAAAAGGCTGTCAAACAATTACAAGATGGACTTAAAGA

TAATAGTATTGGTAAGATTACGGTCAGTTTCAATGATGGTGTGGTAGGAG

AAGTAGCACCTAAATCAGCGAATAAGAAAGCAGATCGAGATGCAGCCGCA

GAAAAGTTGTATAATCTTGTAAATACACAATTAGACAAATTAGGCGATGG

CGATTATGTAGATTTTTCTGTTGATTACAATCTAGAGAATAAGATTATCA

CCAATCAAGCCGATGCCGAAGCTATTGTTACTAAATTGAATTCGTTAAAT

GAAAAGACGCTAATTGATATTGCAACTAAAGATACGTTTGGAATGGTGTC

TAAAACGCAGGATTCTGAAGGAAAGAATGTTGCGGCAACAAAAGCGTTAA

AAGTAAAAGATGTGGCAACTTTTGGCTTAAAGAGTGGAGGTAGTGAAGAT

ACCGGATATGTTGTCGAAATGAAAGCGGGTGCTGTTGAAGATAAGTATGG
```

-continued

```
TGACAACACTGACAAGACTTACGTTAAGGTTGCAAACTTTAGATAATAAA

GATCTTCGAATTCCCGCGGCCGC
```

In various embodiments of any of the aspects delineated herein, the vector is a *Lactoccocus, Lactobacillus, Lactobacillus acidophilus*, or *Lactobacillus casei* expression vector. In certain embodiments, the vector has a *Lactococcus* or *Lactobacillus* origin of replication. In specific embodiments, the vector is pMGM10, pMGM11, pTRK848, or pTRK882.

In various embodiments of any of the aspects delineated herein, the vector comprises a first sequence identical to a sequence of a first fragment in a *Lactobacillus* genome, wherein the first fragment is located at the 5' or 3' terminus of thyA gene, or within the thyA gene of *Lactobacillus*. In various embodiments of any of the aspects delineated herein, the vector comprises a second sequence identical to a sequence of a second fragment in a *Lactobacillus* genome, wherein the second fragment is located at the 5' or 3' terminus of a thyA gene. In various embodiments of any of the aspects delineated herein, the vector has a sequence identical to a sequence of a fragment in *Lactobacillus acidophilus*, or *Lactobacillus casei* genome.

In various embodiments of any of the aspects delineated herein, the cell is a *Lactoccocus, Lactoccocus lactis, Lactobacillus, Lactobacillus acidophilus*, or *Lactobacillus casei* cell. In various embodiments of any of the aspects delineated herein, the nucleic acid sequence encoding the chimeric SlpA peptide is integrated into the chromosome of the isolated cell.

In various embodiments of any of the aspects delineated herein, the subject is a human or animal.

In various embodiments of any of the aspects delineated herein, the subject has undergone or is undergoing treatment provided at NCBI Accession No. CAJ69681 or WP_011254065 and having bacterial adherence activity. Exemplary SlpA amino acid sequences are provided below (SEQ ID NO: 6) and SEQ ID NO: 7, respectively:

```
Clostridium difficile SlpA (full length sequence)
  1   mnkkniaiam sgltvlasaa pvfaattgtq gytvvkndwk kavkqlqdgl kdnsigkitv

 61   sfndgvvgev apksankkad rdaaaeklyn lvntqldklg dgdyvdfsvd ynlenkiitn

121   qadaeaivtk lnslnektli diatkdtfgm vsktqdsegk nvaatkalkv kdvatfglks

181   ggsedtgyvv emkagavedk ygkvgdstag iainlpstgl eyagkgttid fnktlkvdvt

241   ggstpsavav sgfvtkddtd laksgtinvr vinakeesid idassytsae nlakryvfdp

301   deiseaykai valqndgies nlvqlvngky qvifypegkr letksandti asqdtpakvv

361   ikanklkdlk dyvddlktyn ntysnvvtva gedrietaie lsskyynsdd knaitdkavn

421   divlvgstsi vdglvaspla sektaplllt skdkldssvk seikrvmnlk sdtgintskk

481   vylaggvnsi skdvenelkn mglkvtrlsg edryetslai adeigldndk afvvggtgla

541   damsiapvas qlkdgdatpi vvvdgkakei sddaksflgt sdvdiiggkn syskeieesi

601   dsatgktpdr isgddrqatn aevlkeddyf tdgevvnyfv akdgstkedq lvdalaaapi

661   agrfkespap iilatdtlss dqnvayskav pkdggtnlvq vgkgiassvi nkmkdlldm

Lactobacillus acidophilus
  1   mkknlrivsa aaaallavap vaasaystvs aattinasss aintntnaky dvdvtpsvsa

 61   vaantanntp aiagnitgti sasyngktyt anlkadtena titaagstta vkpaelaagv

121   aytvtvndvs fnfgsenagk tvtlgsansn vkftgtnsdn qtetnvstlk vkldqngvas

181   ltnvsianvy ainttdnsnv nfydvtsgat vtngaysvna dngggvnvan vvaainskyf

241   aagyadkkln trtantedai kaalkdqkid vnsvgyfkap htftvnvkat sntngksatl

301   pvvvtvpnva eptvasyskr imhnayyydk dakrvgtdsv krynsysvlp ntttingkty

361   yqvvengkav dkyinaanid gtkrtlkhna yvyasskkra nkvvlkkgev vttygasytf

421   kngqkyykig dntdktyvkv anfr
```

with one or more antibiotics (e.g., a cephalosporin, metronidazole, fluoroquinolone, such as moxifloxacin or vancomycin and fidaxomycin and the like). In various embodiments of any of the aspects delineated herein, the administration of the *Lactoccocus* or *Lactobacillus* expressing a chimeric SlpA polypeptide is by oral administration.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Surface-Layer Protein A (SlpA)" is meant a polypeptide or fragment thereof having at least about 85% or greater amino acid identity to the amino acid sequence By "SlpA nucleic acid molecule" is meant a polynucleotide encoding SlpA.

By "SlpA variable domain" is meant a polypeptide having 85% identity to the following sequence (SEQ ID NO: 1):

```
AAPVFAATTGTQGYTVVKNDWKKAVKQLQDGLKDNSIGKITVSENDGVVG

EVAPKSANKKADRDAAAEKLYNLVNTQLDKLGDGDYVDFSVDYNLENKII

TNQADAEAIVTKLNSLNEKTLIDIATKDTFGMVSKTQDSEGKNVAATKAL

KVKDVATFGLKSGGSEDTGYVVEMKAGAVEDKYGKVGDSTAGTATNLPST

GLEYAGKGTTIDFNKTLKVDVTGGSTPSAVAVSGFVTKDDTDLA
```

In one embodiment, the SlpA variable domain is from *C. difficile* SlpA.

By "SlpA cell wall binding domain" is meant a polypeptide having 85% identity to the following sequence (SEQ ID NO: 8):

```
agedrietaielsskyynsddknaitdkavndivlvgstsivdglvaspl

asektaplllt skdkldssykseikrymnlksdtgintskkvylaggvns

iskdvenelknmglkvtrlsgedryetslaiadeigldndkafvvggtgl
```

-continued

```
adamsiapvasqlkdgdatpivvvdgkakeisddaksflgtsdvdiiggk

nsyskeieesidsatgktpdrisgddrqatnaevlkeddyftdgevvnyf

vakdgstkedqlvdalaaapiagrfkespapiilatdtlssdqnvayska

vpkdggtnlvqvgkgiassvink
```

In one embodiment, the SlpA cell wall binding domain is from *Lactobacillus* (e.g., *Lactobacillus acidophilus*).

By "chimeric SlpA" is meant a polypeptide having two or more SlpA sequences from two or more bacterial strains. In one embodiment, a chimeric SlpA has an SlpA variable domain from *C. difficile* SlpA and an SlpA cell wall binding from *Lactobacillus acidophilus. In another embodiment, a chimeric SlpA has an SlpA signal sequence from Lactobacillus acidophilus*, an SlpA variable domain from *C. difficile* SlpA and an SlpA cell wall binding from *Lactobacillus acidophilus*. An exemplary chimeric SlpA sequence is provided below (SEQ ID NO: 7):

```
MKKNLRIVSAAAAALLAVAPVAASAVSTVSAAAPVFAATTGTQGYTVVKN   50

DWKKAVKQLQDGLKDNSIGKITVSFNDGVVGEVAPKSANKKADRDAAAEK  100

LYNLVNTQLDKLGDGDYVDFSVDYNLENKIITNQADAEAIVTKLNSLNEK  150

TLIDIATKDTFGMVSKTQDSEGKNVAATKALKVKDVATFGLKSGGSEDTG  200

YVVEMKAGAVEDKYGKVGDSTAGIAINLPSTGLEYAGKGTTIDFNKTLKV  250

DVTGGSTPSAVAVSGFVTKDDTDLASNTNGKSATLPVVVTVPNVAEPTVA  300

SVSKRIMHNAYYYDKDAKRVGTDSVKRYNSVSVLPNTTTINGKTYYQVVE  350

NGKAVDKYINAANIDGTKRTLKHNAYVYASSKKRANKVVLKKGEVVTTYG  400

ASYTFKNGQKYYKIGDNTDKTYVKVANFR*
```

A codon-optimized nucleic acid sequence of the above chimeric SlpA sequence for expression in *Lactobacillus* is provided below at FIG. 1C.

By "undesirable gut microbiome" is meant a community of microbes comprising a pathogen or having a biological activity associated with a pathogenic process. In one embodiment, an undesirable gut microbiome comprises an increased number or percentage of *Clostridium difficile* relative to the number or percentage of *C. difficile* present in the gut of a healthy control subject.

By "normal gut flora" is meant a population of microbes that is substantially similar to the population of microbes present in the gut of a healthy control subject.

By "ameliorate" is meant decrease, suppress, attenuate, diminish, arrest, or stabilize the development or progression of a disease.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "effective amount" is meant the amount of a composition of the invention (e.g., comprising a probiotic bacteria expressing *Clostridium difficile* SlpA, or fragment thereof) required to ameliorate the symptoms of a disease relative to an untreated patient. The effective amount of probiotic bacteria of the invention varies depending upon the manner of administration, the age, body weight, and general health of the subject. Ultimately, the attending physician or veterinarian will decide the appropriate amount and dosage regimen. Such amount is referred to as an "effective" amount.

By "expression vector" is meant a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as plasmids, cosmids, and viruses that incorporate the recombinant polynucleotide.

By "fragment" is meant a portion of a polypeptide or nucleic acid molecule. This portion contains, preferably, at least 10%, 20%, 30%, 40%, 50%, 60%, 70%, 80%, or 90% of the entire length of the reference polypeptide or nucleic acid molecule. A fragment may contain 5, 10, 15, 20, 30, 40, 50, 60, 70, 80, 90, or 100 amino acids or nucleotides.

The terms "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. Thus, a purified isolated bacterium that is part of a culture or inoculum is at least about 90%, 95% or 100% free of bacteria, fungi, viruses, or other undefined microbes.

By "marker" is meant any analyte associated with a disease or disorder.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

By "reference" is meant a standard or control condition.

A "reference sequence" is a defined sequence used as a basis for sequence comparison.

By "subject" is meant a mammal, including, but not limited to, a human or non-human mammal, such as a bovine, equine, canine, ovine, or feline.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1E depict the generation of plasmid constructs and the biological sequences used. FIG. 1A depicts the construction of plasmid pMGM10. FIG. 1B depicts the construction of plasmid pMGM11. FIG. 1C depicts the codon-optimized slpA chimera nucleic acid sequence that was cloned into the plasmids pMGM10 and pMGM11. FIG. 1D depicts the amino acid sequence of the SlpA chimera polypeptide. FIG. 1E depicts the promoter sequences used in constructing the plasmids: fructooligosaccharides (Fos) promoter in plasmid pTRK848/pMGM11 and phosphoglycerate mutase (pgm) promoter pTRK882/pMGM10.

DETAILED DESCRIPTION OF THE INVENTION

Figure 1A:
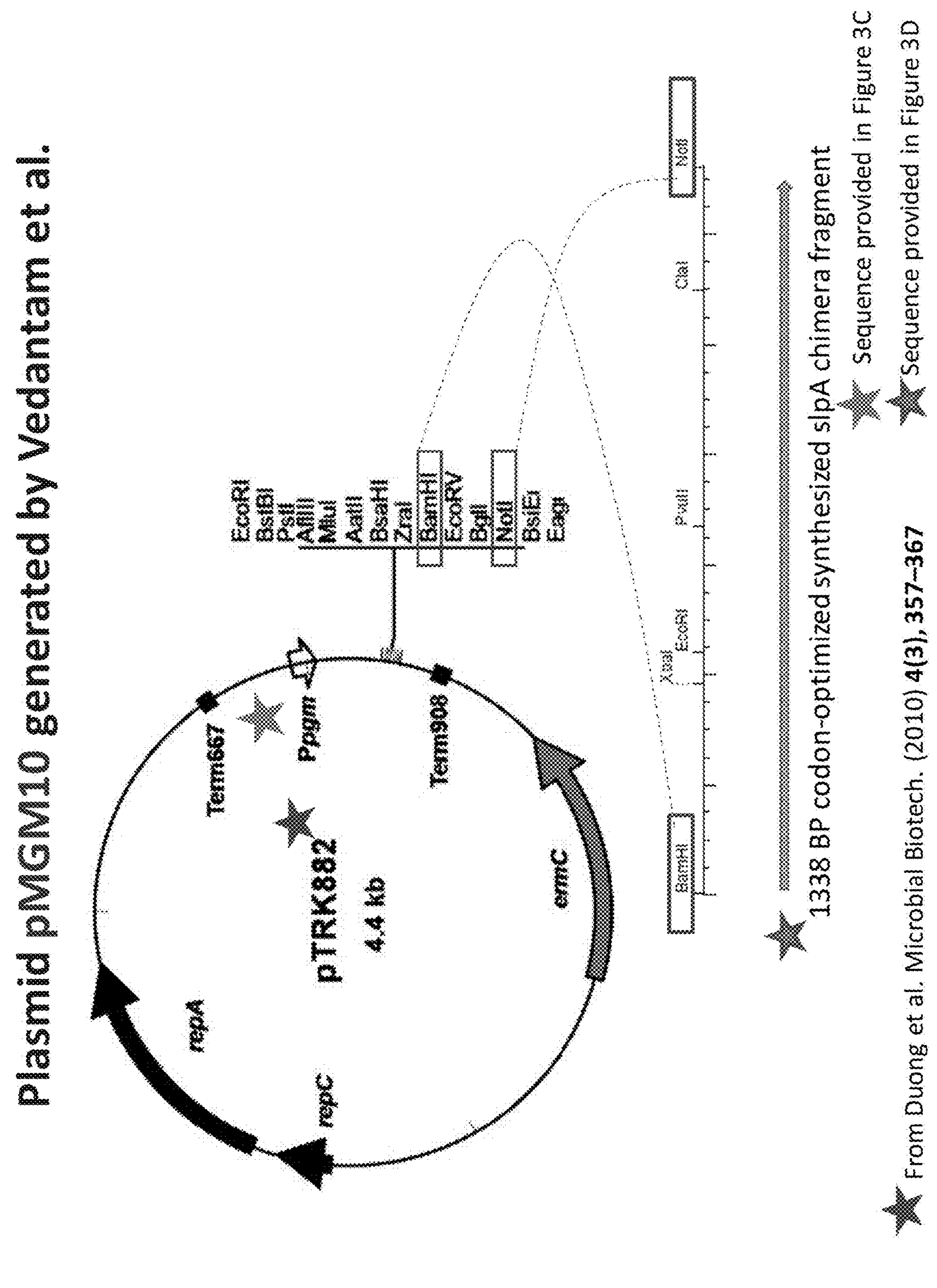
Figure 1B:
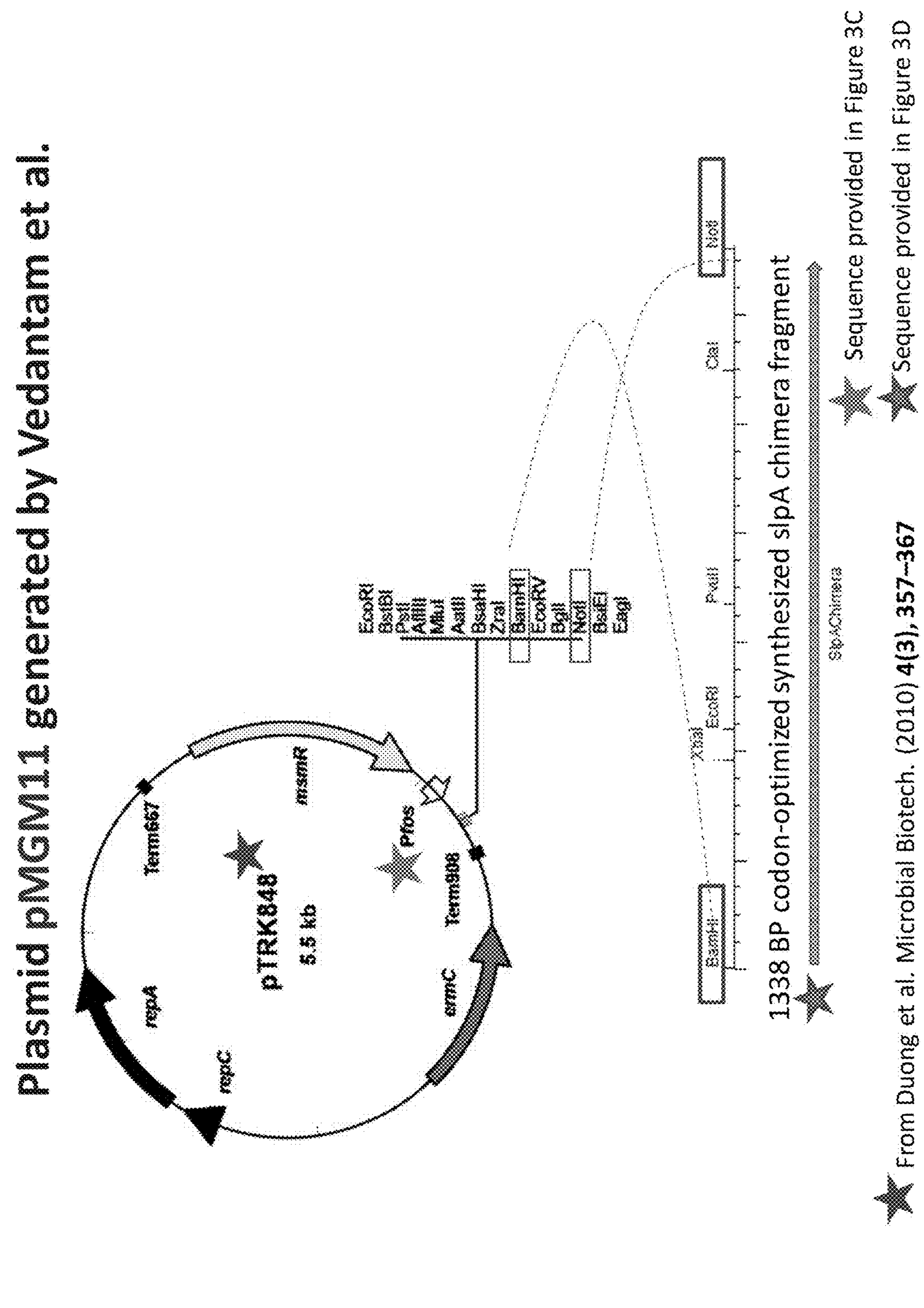
Figure 1E:
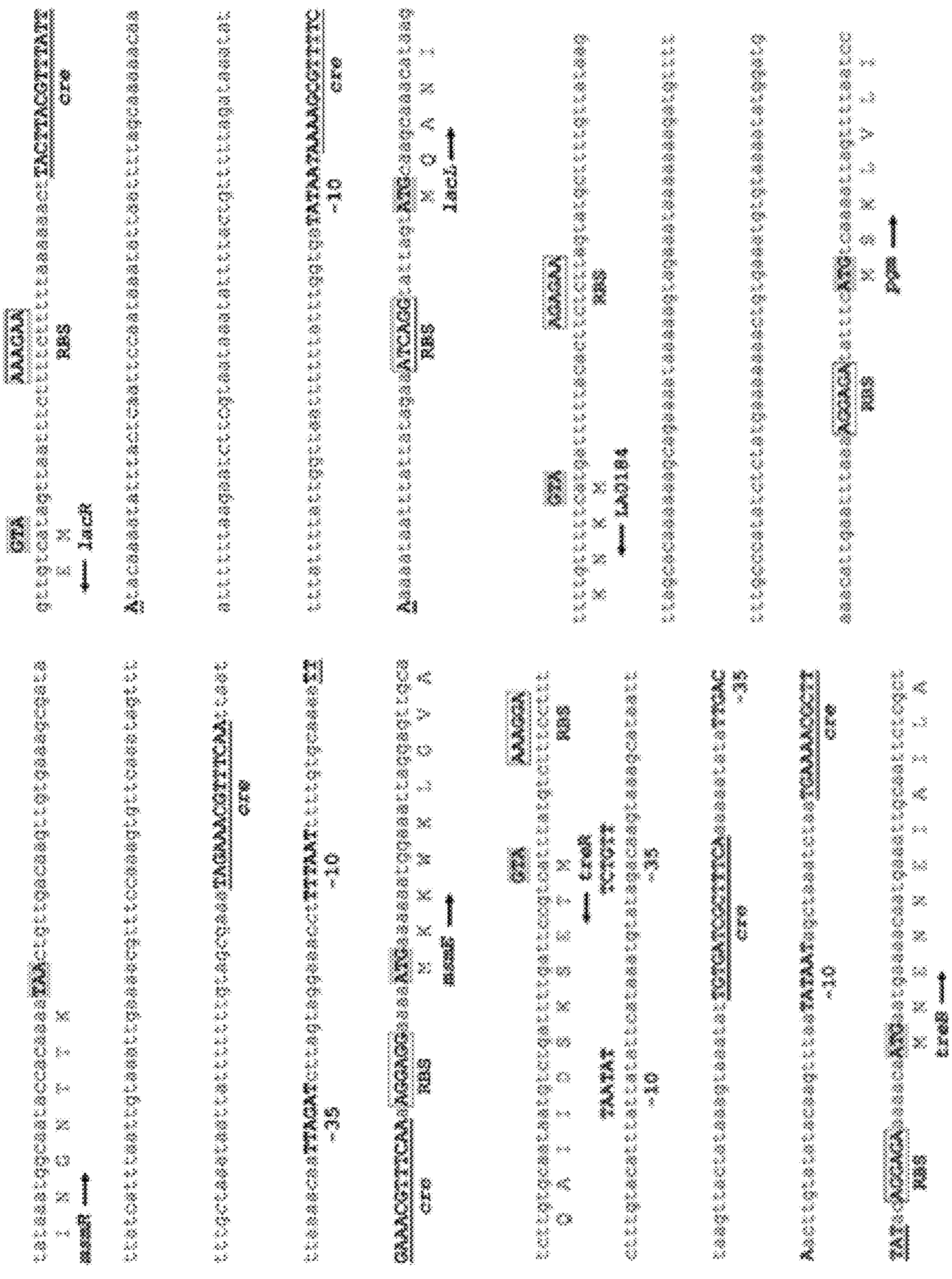

The invention provides a probiotic bacteria (e.g., *Lactobacillus, Lactococcus*) expressing the *Clostridium difficile* surface protein SlpA, or a fragment or chimeric polypeptide thereof, and its use for colonizing the gut or digestive tract of a subject. The invention also provides a method of treating or preventing *Clostridium difficile* infection and colonization. The invention features use of the probiotic bacteria of the invention for the replacement of a gut microbiome associated with disease.

The invention is based, at least in part, on the discovery that expression of *Clostridium difficile* SlpA (e.g., chimeric SlpA), or fragment thereof, in *Lactobacillus* or *Lactococcus* is effective for colonizing the gut with the recombinant bacteria. It was also found that recombinant *Lactobacillus* protected the gut from virulent *Clostridium difficile* challenge. These findings indicate that administration of gut recombinantly expressing *Clostridium difficile* SlpA, or fragment thereof can be used to treat or prevent *Clostridium difficile* infection and colonization.

*Clostridium difficile*

*Clostridium difficile* is a gram-positive, anaerobic, spore-forming bacterium, and causes the antibiotic-associated diarrheal disease, *C. difficile* infection (CDI). It is also a leading cause of bacterial healthcare-associated infections in hospitals in the United States. Like many enteric pathogens, *Clostridium difficile* must associate with the intestinal mucosa to begin the process of host colonization.

Multiple *C. difficile* adhesins have been described, including the flagellin FliC, the flagellar cap protein FliD, fibronectin-binding proteins, a heat-shock protein, GroEL, the surface associated, heat-shock-induced adhesin, Cwp66, and the surface layer protein, SlpA. SlpA contains two biologically distinct entities, the high-molecular weight (HMW) and the low molecular weight (LMW) subunits, which are derived via Cwp84-mediated cleavage of a single precursor protein, and assemble on the bacterial surface into a paracrystalline lattice. The two subunits associate with high affinity through the N-terminus of the HMW protein and the C-terminus of the LMW protein.

Cwp66 and SlpA are encoded by two genes in a 17-gene cluster that encodes many surface-associated proteins. Such S-layer proteins (SLPs) provide structural integrity to the cells, act as molecular sieves, bind to host tissues and extracellular matrix proteins, and contribute to host cell adhesion and immune evasion.

Surface-Layer Protein A (SlpA)

Many gram-positive bacteria including *C. difficile* possess a surface-layer that covers the peptidoglycan-rich cell wall. This "S-layer" consists of many proteins that form a paracrystalline lattice around the bacterial cell. The most abundant S-layer protein in *C. difficile* is SlpA, a major contributor of adhesion to, and colonization of, intestinal epithelial cells. (Merrigan et al. PLoS ONE 8(11): e78404). Individual subunits of the protein (varying in sequence between strains) mediated host-cell attachment to different extents. Pre-treatment of host cells with crude or purified SlpA subunits, or incubation of vegetative bacteria with anti-SlpA antisera significantly reduce *C. difficile* attachment. SlpA-mediated adherence-interference correlates with the attachment efficiency of the strain from which the protein was derived, with maximal blockage observed when SlpA is derived from highly adherent strains. In addition, SlpA-containing preparations from a non-toxigenic strain effectively blocked adherence of a phylogenetically distant, epidemic-associated strain, and vice-versa. Taken together, these results suggest that SlpA plays a major role in *C. difficile* infection, and that it may represent an attractive target for interventions aimed at abrogating gut colonization by this pathogen.

Therapeutic Compositions

The invention features probiotic bacteria expressing *Clostridium difficile* SlpA or fragment thereof (e.g., chimeric SlpA). In particular, *Clostridium difficile* SlpA, or fragment thereof, is expressed in *Lactoccocus* (e.g., *Lactoccocus lactis*) or *Lactobacillus* cells (e.g., *Lactobacillus acidophilus* or *Lactobacillus casei*). In additional embodiments, one or more strains of probiotic bacteria expressing a chimeric SlpA polypeptide are administered or formulated as a therapeutic composition. In certain embodiments, the SlpA expressed is a chimeric SlpA comprising a *C. difficile* SlpA variable domain and *Lactobacillus* (e.g., *Lactobacillus acidophilus* or *Lactobacillus casei*) SlpA cell wall binding domain. The SlpA additionally includes a bacterial secretion signal that is appropriate for surface expression in its host cell (e.g., *Lactoccocus, Lactobacillus, Lactobacillus acidophilus* or *Lactobacillus casei*). In various embodiments, the invention also includes nucleic acid molecules and vectors encoding a chimeric SlpA polypeptide. Vectors encoding the chimeric SlpA polypeptide can be used to direct or regulate the expression of the chimeric SlpA by the cell (see e.g., Duong et al., Microbial Biotechnoloy 2010, 4(3): 357-367 which is herein incorporated in its entirety by reference). Such vectors contain one or more origin of replication sequences that can be used by a bacterial cell, promoter sequences for expression in a bacterial cell (e.g., constitutive or inducible), genetic markers for selection (e.g., antibiotic resistance); origin of transfer sequences for bacterial conjugation (e.g., traJ), and may also be codon optimized for protein expression.

Alternatively, nucleic acid sequences encoding chimeric SlpA may be integrated into the *Lactobacillus* or *Lactococcus* genome. In certain embodiments, nucleic acid sequences encoding the chimeric SlpA can be integrated into the *Lactobacillus* or *Lactococcus* genome through recombination between vectors comprising the nucleic acid sequence encoding the chimeric SlpA poly peptide and bacterial chromosome. Such techniques are well known in the art (see e.g., Leenhouts, et al., Appl. Environ. Microbiol. 1989, 55(2): 394-400, and Gaspar, et al., Appl. Environ. Microbiol. 2004, 70(3): 1466-74 which are herein incorporated in their entirety by reference).

Probiotic strains may also be engineered with auxotrophic selection, for example requiring thiamine or thymine supplementation for survival.

Methods of the Invention

The present invention provides methods of treating diseases or symptoms thereof associated with the presence of one or more undesirable bacteria in the gut of a subject. Accordingly, the invention provides compositions and methods for treating a subject having or at risk of developing a disease associated with undesirable changes in the gut microbiome, the method involving administering a therapeutically effective amount of a composition comprising a probiotic bacteria of the invention to a subject (e.g., a mammal, such as a human). In particular, the compositions and methods of the invention are effective for treating or preventing *Clostridium difficile* infection, colonization, or diseases and symptoms thereof (e.g., diarrhea). Without being bound to theory, *Lactobacillus* or *Lactococcus* expressing *Clostridium difficile* SlpA or fragment thereof (e.g., chimeric SlpA) colonize the gut and compete with *Clostridium difficile* for binding and colonization. Accordingly, the method includes the step of administering to a mammal a therapeutic amount of an amount of a composition comprising one or more probiotic bacteria strains of the invention sufficient to treat the disease or disorder or symptom thereof, under conditions such that the disease or disorder is treated.

Identifying a subject in need of treatment for a disease associated with the gut microbiome can be in the judgment of a health care professional and can be subjective (e.g. opinion) or objective (e.g. measurable by a test or diagnostic method). In certain embodiments, the subject has undergone or is undergoing treatment with antibiotics. As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of a composition comprising the probiotic bacteria of the invention to a subject (e.g., human) in need thereof. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The compositions herein may be also used in the treatment of any other disorders in which a microbial imbalance in the digestive tract may be implicated.

Methods of Delivery

Compositions comprising the probiotic bacteria of the invention may be administered orally, rectally, or enterally. Preferably compositions administered to a subject in tablet form, by feeding tube, by enema, or by colonoscopy. Preferably, the probiotic bacteria of the invention are diluted in a suitable excipient (e.g., saline solution). An effective dose may include $10^6$-$10^9$ colony forming units of bacteria per day).

Expression of Recombinant Polypeptides

In order to express the fusion protein of the invention, DNA molecules obtained by any of the methods described herein or those that are known in the art, can be inserted into appropriate expression vectors by techniques well known in the art. For example, a double stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding an SlpA chimeric polypeptide operatively linked to regulatory sequences, e.g., promoter sequences, terminator sequences, and the like, as defined herein. Recombinant vectors which allow for expression of the genes or nucleic acids included in them are referred to as "expression vectors."

In some of the molecules of the invention described herein, one or more DNA molecules having a nucleotide sequence encoding one or more polypeptides of the invention are operatively linked to one or more regulatory sequences, which are capable of integrating the desired DNA molecule into a prokaryotic host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

After the introduction of one or more vector(s), host cells are usually grown in a selective medium, which selects for the growth of vector-containing cells. Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

Kits

The invention provides kits for colonizing probiotic bacteria of the invention in the gut of a host. The invention also provides kits for the treatment or prevention of *Clostridium difficile* infection or colonization. In particular embodiments, the kit comprises a sterile container which contains a therapeutic or prophylactic composition comprising the probiotic bacteria of the invention; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

The kit preferably contains instructions that generally include information about the use of the composition for the expansion of the microbial consortia in the gut of the subject. The kit further contains precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Probiotic Bacterial Strains Expressing Chimeric SlpA are Effective at Gut Colonization and Protecting Against *C. difficile* Challenge Developing novel interventions that avoid the use of antibiotics is important in the treatment of *C. difficile* infection (CDI). Many gram-positive bacteria including *C. difficile* possess a surface-layer that covers the peptidoglycan-rich cell wall. This "S-layer" consists of many proteins that form a paracrystalline lattice around the bacterial cell. Surface layer protein A (SlpA), an adhesin and a major component of the cell surface layer (or S-layer) of *C. difficile*, facilitates gut colonization. Novel probiotic organisms were designed and engineered to express *C. difficile* SlpA on their cell surface (FIGS. 1A-1E). Without being bound to a particular theory, the engineered probiotic colonizes gut niches specifically occupied by virulent infecting *C. difficile* strains, thus preventing disease.

Figure 2:
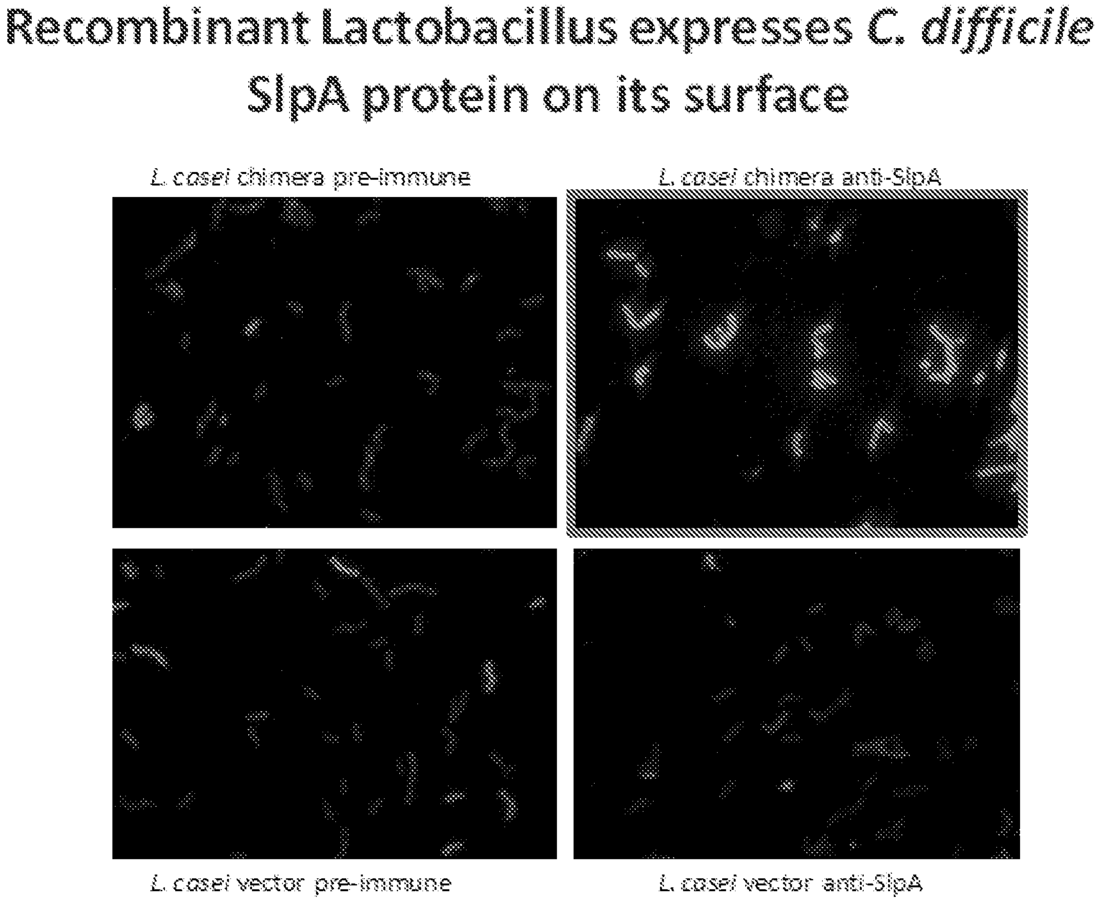
FIG. 2 are immunofluorescence images showing the surface expression of *C. difficile* SlpA in *Lactobacillus casei* compared to pre-immune serum and vector only controls.

A chimeric SlpA polypeptide was created that included *C. difficile* SlpA sequences for bacterial adherence. The chimeric SlpA polypeptide was designed with a *L. acidophilus* cell-wall binding domain and secretion signal sequence and the host-cell binding domain of *C. difficile*. Plasmid vectors were constructed to express the slpA chimera either constitutively or in response to a fructose oligosaccharide inducer. Plasmid vectors encoding SlpA chimeras were designed and introduced into probiotic bacterial strains *Lactoccocus lactis* and *Lactobacillus acidophilus* via three methods, electroporation, bacterial conjugation (pMTL82151 with pTRK848 comprising traJ; pMTL82151 with pTRK882 comprising traJ), and protoplasting. Transformants were assessed for stable carriage of introduced plasmids, and tested for SlpA surface expression. Western blot analysis and cell surface immunofluorescence showed that the chimeric SlpA was expressed by the probiotic bacterial cells (FIG. 2).

Figure 3:
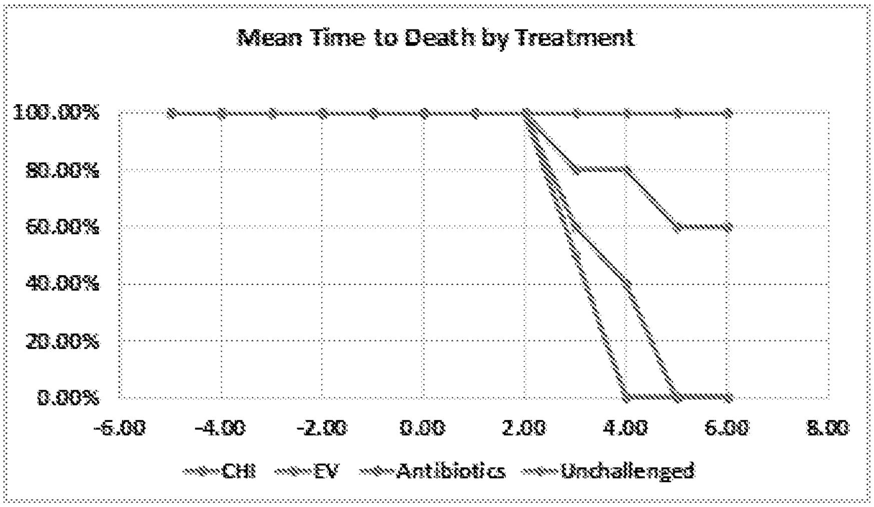
FIG. 3 is a graph showing mean time to death in Syrian Golden hamsters challenged with virulent *Clostridium difficile* and treated with recombinant *Lactobacillus* expressing a chimeric SlpA (CHI) or *Lactobacillus* carrying an empty vector (EV) or undergoing antibiotic treatment (Antibiotics), compared to animals that were unchallenged (Unchallenged).

To test the ability of the recombinant bacteria expressing the chimeric SlpA to occlude *C. difficile* competitively, a study was performed in Syrian Golden hamsters (FIG. 3). Animals were treated with recombinant *Lactobacillus* expressing a chimeric SlpA or *Lactobacillus* carrying an empty vector. Another group of animals underwent treatment with antibiotics. animals that were administered *Lactobacillus* expressing chimeric SlpA showed extended survival and overall survival at the conclusion of the experiment. By comparison, none of the animals that were treated with antibiotics or administered *Lactobacillus* with empty vector survived to the end of the experiment. All animals that were not challenged with virulent *C. difficile* survived to the end of the experiment. These results show that *Lactobacillus* expressing the chimeric SlpA colonized the gut and was able to protect against virulent *C. difficile* challenge. Thus, this indicates that administration of probiotic bacteria expressing chimeric SlpA has the potential to be an effective treatment or preventative for *C. difficile* infection and/or colonization.

Figure 4:
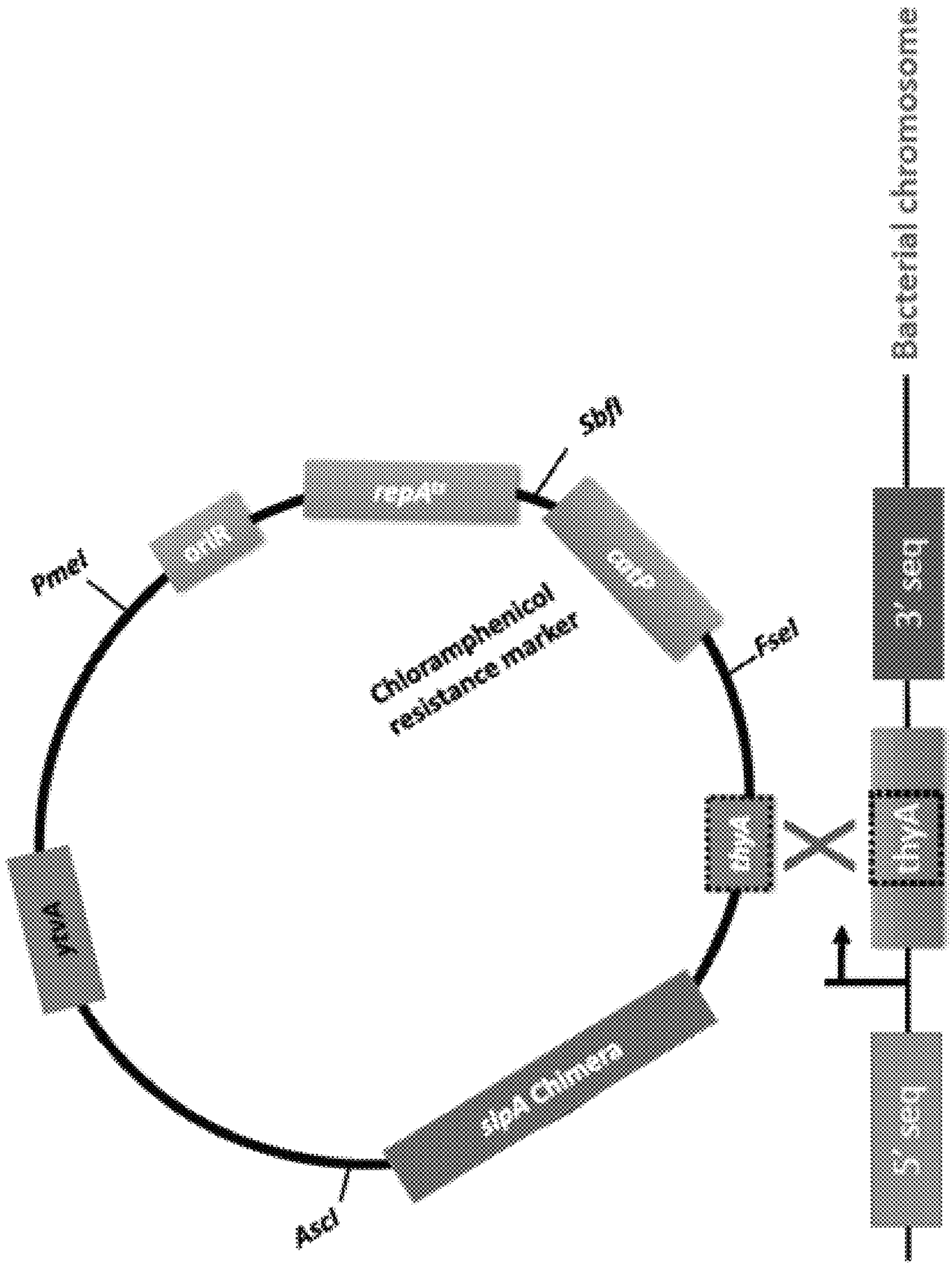
FIG. 4 provides a schematic diagram of a plasmid encoding SlpA chimeric protein. The internal fragment of a thyA directs the chimera integration into the genome and concomitantly insertionally inactivates the thyA, which encodes an essential enzyme thymidylate synthase (ThyA). *Lactobacillus casei* and *Lactobacillus acidophilus* specific constructs were made. A gene catP encodes an enzyme Chloramphenicol acetyltransferase, which is an effector of chloramphenicol resistance in bacteria. A region including an oriR gene and a $repA^{ts}$ gene constitutes a temperature sensitive broad host replicon based on a pWVO1 plasmid. YtvA is an anaerobic fluorescent protein used to confirm transformation of *Lactobacillus* sp and monitor colonization.
Figure 5:
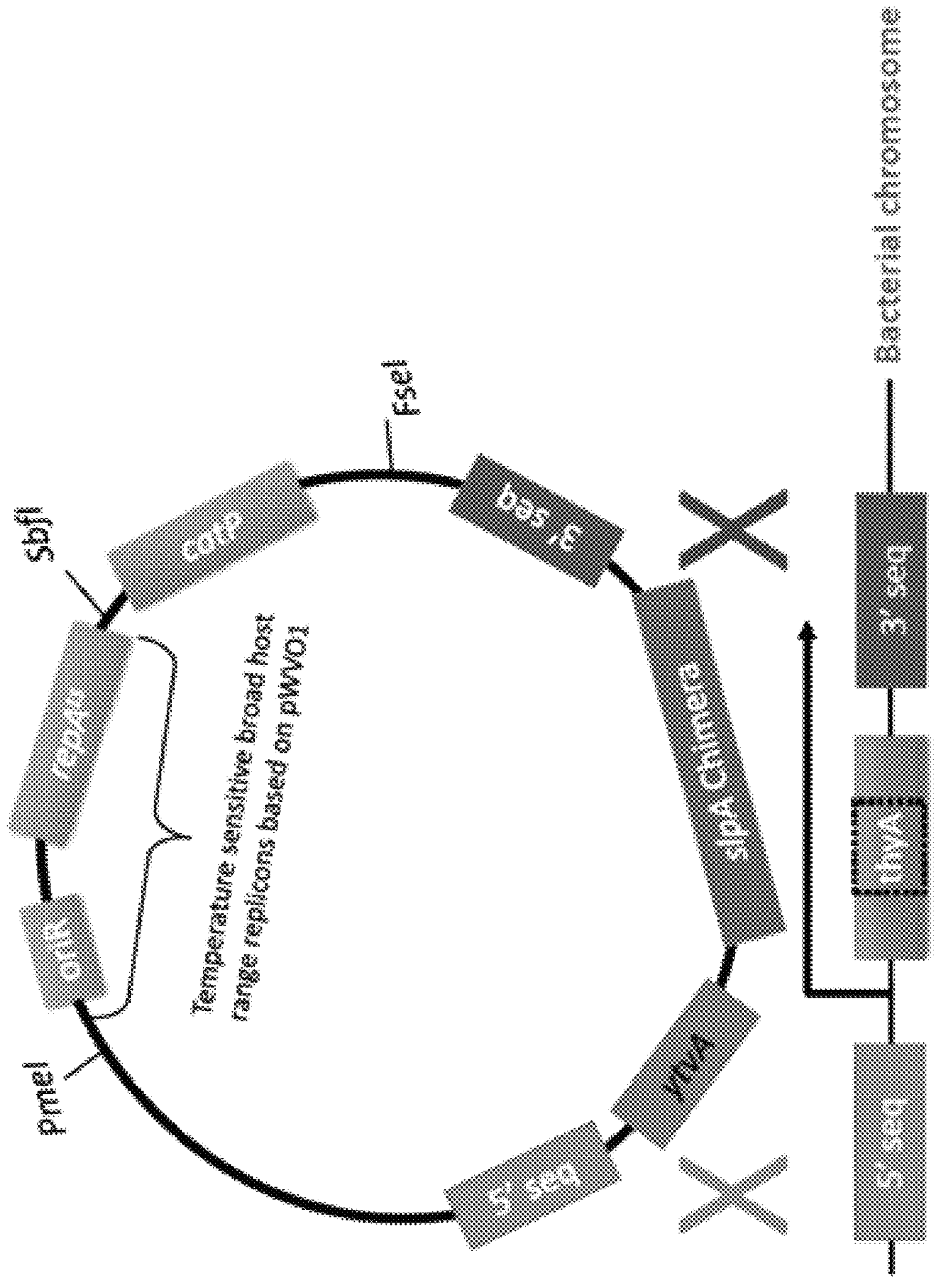
FIG. 5 provides a schematic diagram of a plasmid encoding SlpA chimeric protein. A 5' seq and a 3' seq are two fragments located at 5' and 3' terminus of a thyA gene, respectively, and direct the double homologous recombination to replace the thyA gene in the bacterial chromosome with a SlpA chimeric protein encoding sequence and a YtvA fluorescent reporter encoding sequence. *Lactobacillus casei* and *Lactobacillus acidophilus* specific constructs were made. The thyA gene encodes an essential enzyme thymidylate synthase (ThyA). The YtvA is an anaerobic fluorescent protein used to confirm transformation of *Lactobacillus* sp and monitor colonization. A gene catP encodes an enzyme Chloramphenicol acetyltransferase, which is an effector of chloramphenicol resistance in bacteria. A region including an oriR and a $repA^{ts}$ genes constitutes a temperature sensitive broad host replicon based on pWVO1 plasmid.

Example 2: A Chimeric SlpA Polynucleotide can be Integrated into the *Lactobacillus* Genome Probiotic organisms can include biocontainment features for eventual clinical use and, concomitantly, obviating the requirement of antibiotics for in vivo plasmid maintenance and stable SlpA expression. The SlpA expression may also be controlled. The biological containment can be achieved via a two-step mechanism, where both SlpA expression and *Lactobacillus* sp. survival can be controlled. Novel vectors were designed to allow probiotic organisms to express chimeric SlpA stably and under control (FIGS. 4 and 5). In one embodiment, the nucleic acid sequence encoding a chimeric SlpA peptide can be integrated into a bacterial chromosome to allow stability of SlpA expression in the absence of selection pressure. The chimeric SlpA expression can be expressed under the control of a fructo-oligosaccharide (FOS) promoter. FOSs are well-tolerated, safe and widely-used supplements in humans and agriculturally-relevant animals.

Probiotic organisms expressing the chimeric SlpA protein, such as the lactic acid bacterium, including both *L. casei* and *L. acidophilus*, can be genetically modified such that complete lethality of the probiotic organisms occurs in the absence of thymine supplementation. This “thymineless death” is predicated on the absolute requirement of deoxythymidine triphosphate (dTTP) for DNA synthesis in all living organisms. Of the two pathways for dTTP synthesis in most bacteria, the de novo pathway involves conversion of dUMP to dTMP by the essential enzyme thymidylate synthase (ThyA). The less-used “salvage” pathway involves the conversion of supplemented thymidine into dTMP by thymidine kinase. dTMP is then converted to dTTP. Disruption or mutation of thyA in bacteria results in immediate auxotrophy and, in vitro, can be tolerated only by addition of exogenous thymidine that is utilized by the salvage pathway. Withdrawal of thymidine results in rapid, total cell death. Free thymidine is not abundant or bio-available in vivo (in the gut), and is unable to support growth of thyA auxotrophs. Therefore, the probiotic organisms with thyA gene disrupted will necessarily be lost from the gut unless continually administered.

Figure 6:
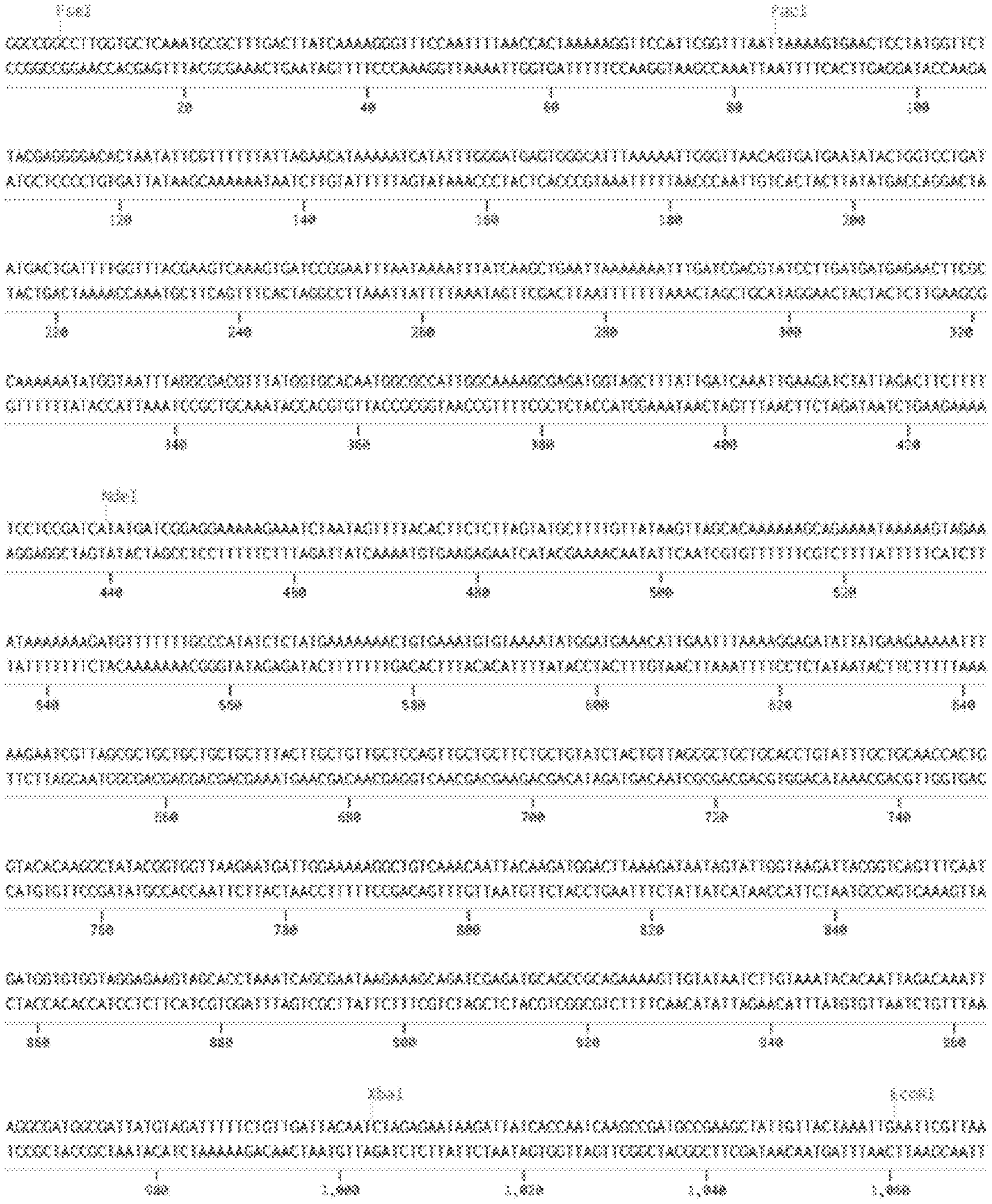
FIG. 6 provides a partial sequence of a plasmid used for a thyA directed integration of a SlpA chimeric protein encoding sequence into a bacterial genome and concomitantly insertionally inactivates thyA in *Lactobacillus casei*.
Figure 6:
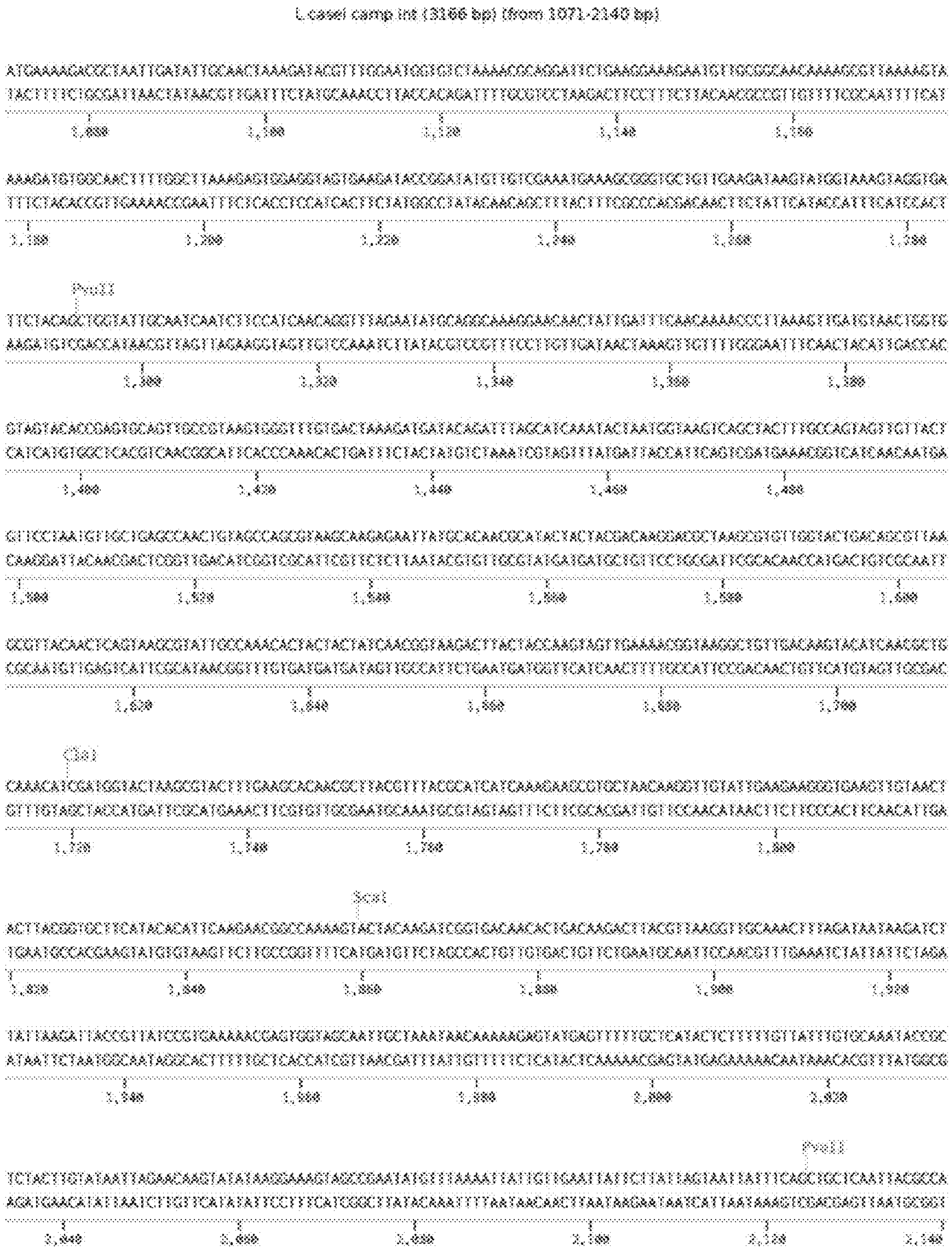
Figure 6:
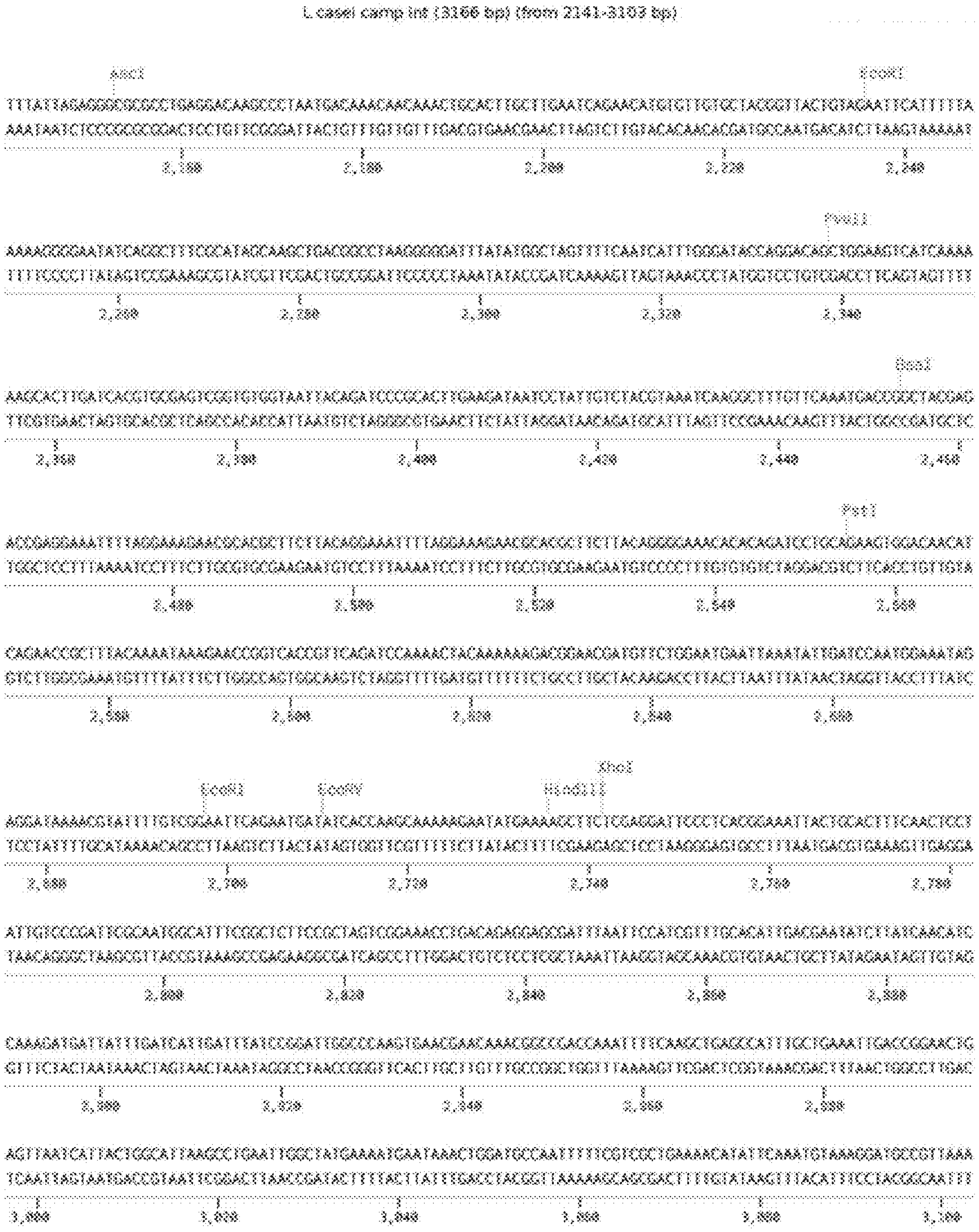
Figure 6:
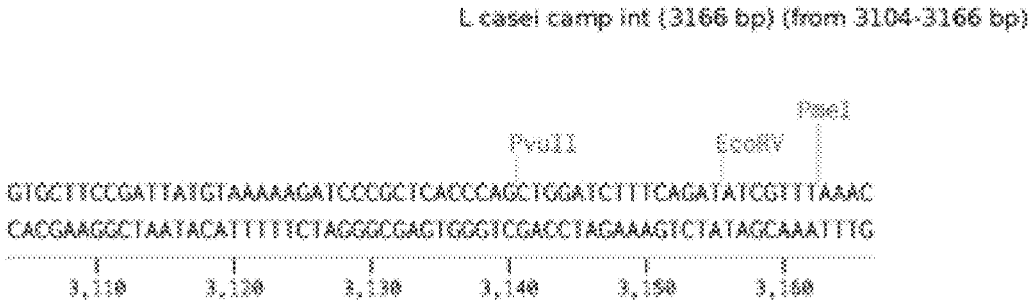
Figure 8:
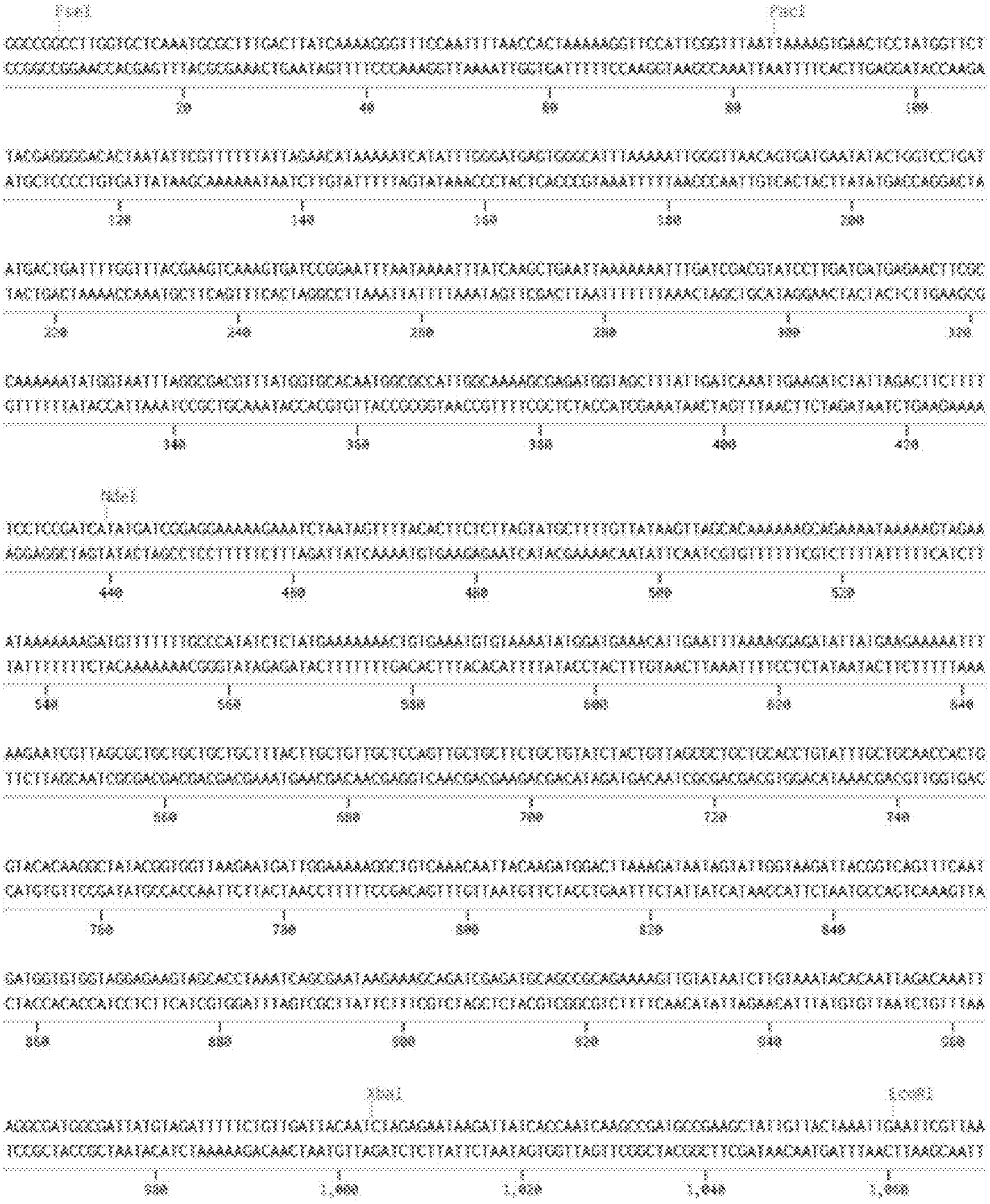
FIG. 8 provides a partial sequence of a plasmid used for a thyA directed integration of a SlpA chimeric protein encoding sequence into a bacterial genome and concomitantly insertionally inactivates thyA in *Lactobacillus acidophilus*.
Figure 8:
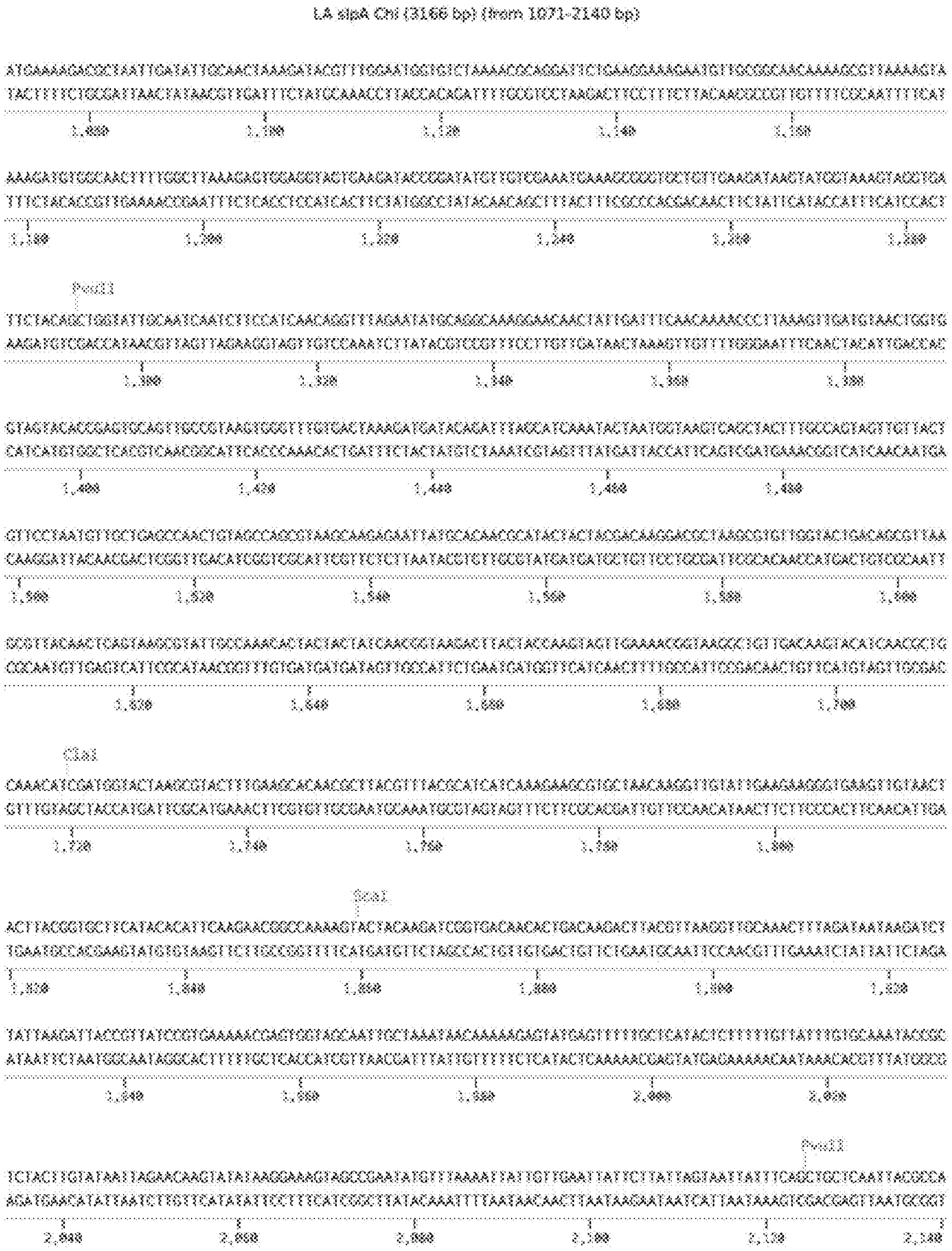
Figure 8:
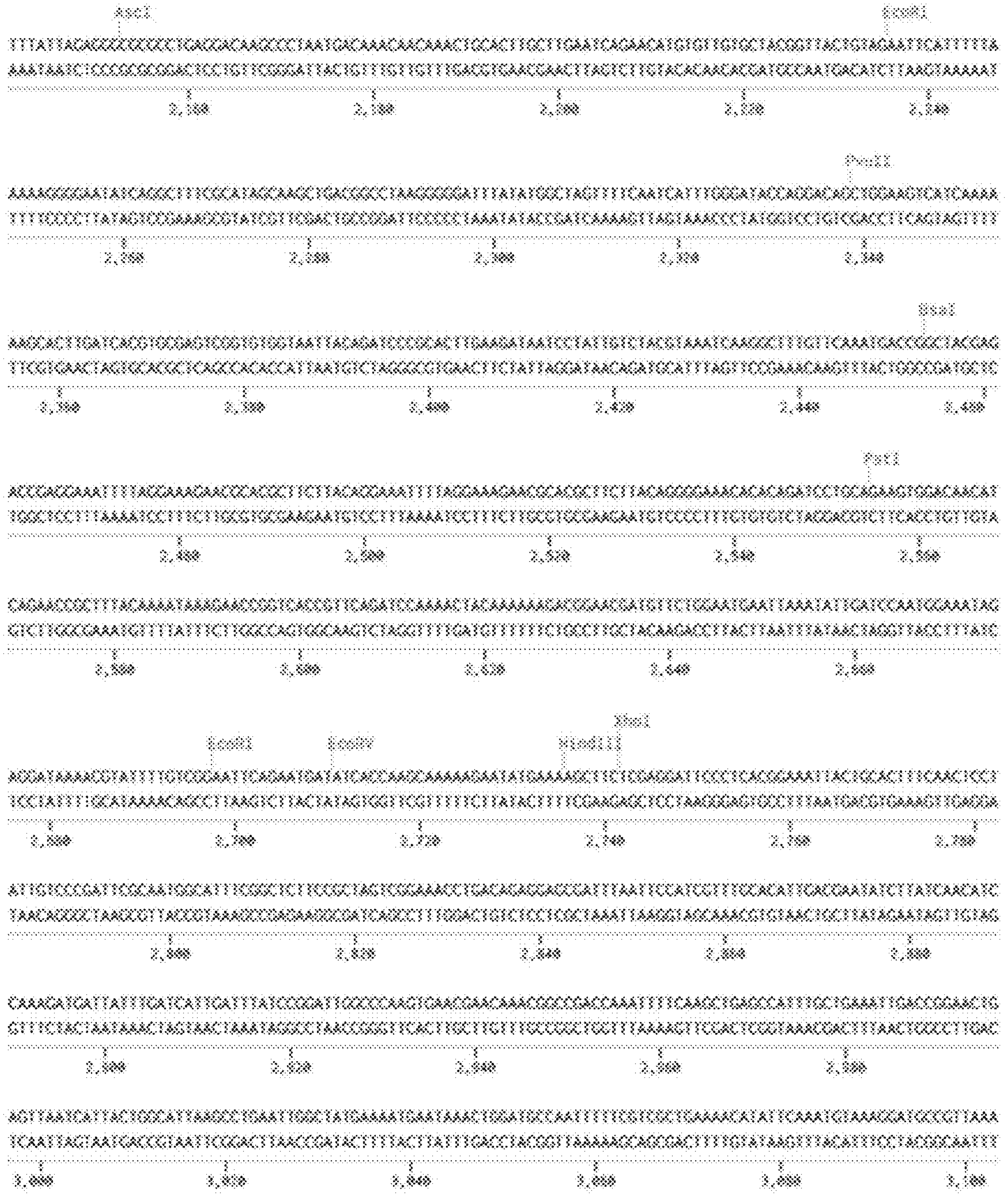
Figure 8:
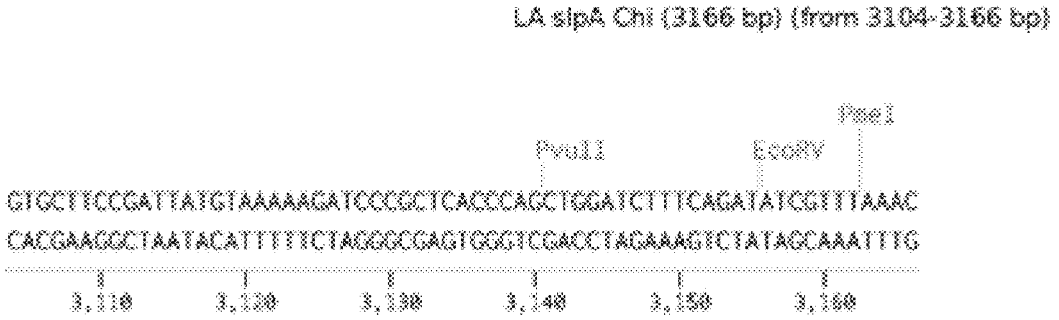

The nucleic acid sequence encoding the chimeric SlpA can be integrated into the *Lactobacillus* sp. through a single homologous recombination at a single site (FIG. 4) or a double homologous recombination (FIG. 5). For the single homologous recombination, one vector is constructed for each species. Thus, a vector is constructed for specific use in *L. casei*, such that the vector includes a nucleic acid sequence that is identical to a nucleic acid sequence of a fragment of the thyA gene in *L. casei*. Another vector is constructed for specific use in *L. acidophilus*, such that the vector includes a nucleic acid sequence that is identical to a nucleic acid sequence of a fragment of the thyA gene in *L. acidophilus*. The sequence of the vector for the specific use in *L. casei* for single recombination is shown in FIG. 6 and the sequence of the vector for the specific use in *L. acidophilus* for single recombination is shown in FIG. 8.

Figure 7:
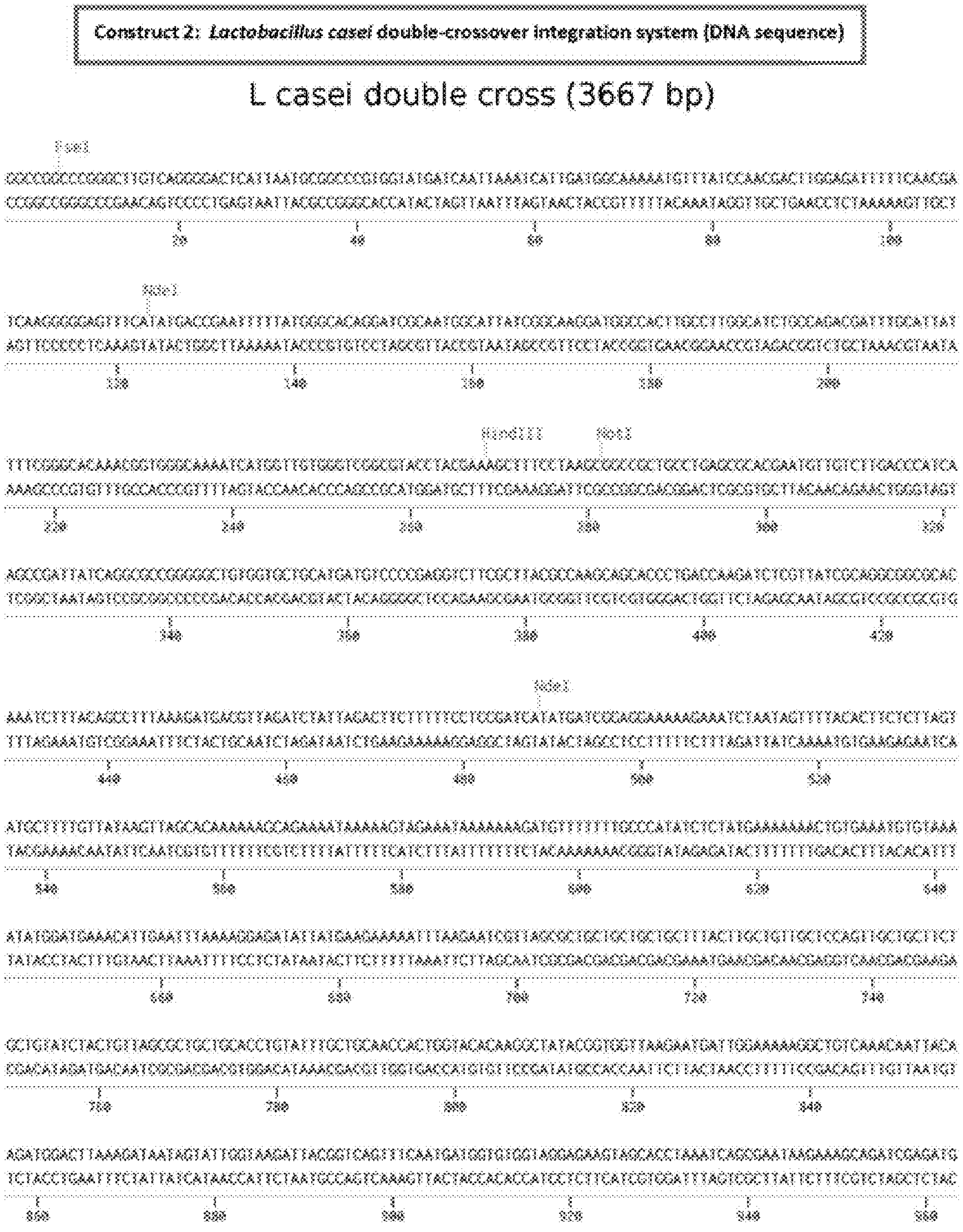
FIG. 7 provides a partial sequence of a plasmid used for double homologous recombination-based system for replacing a thyA gene in a bacterial chromosome with a SlpA chimeric protein encoding sequence and a YtvA fluorescent reporter encoding sequence in *Lactobacillus casei*.
Figure 7:
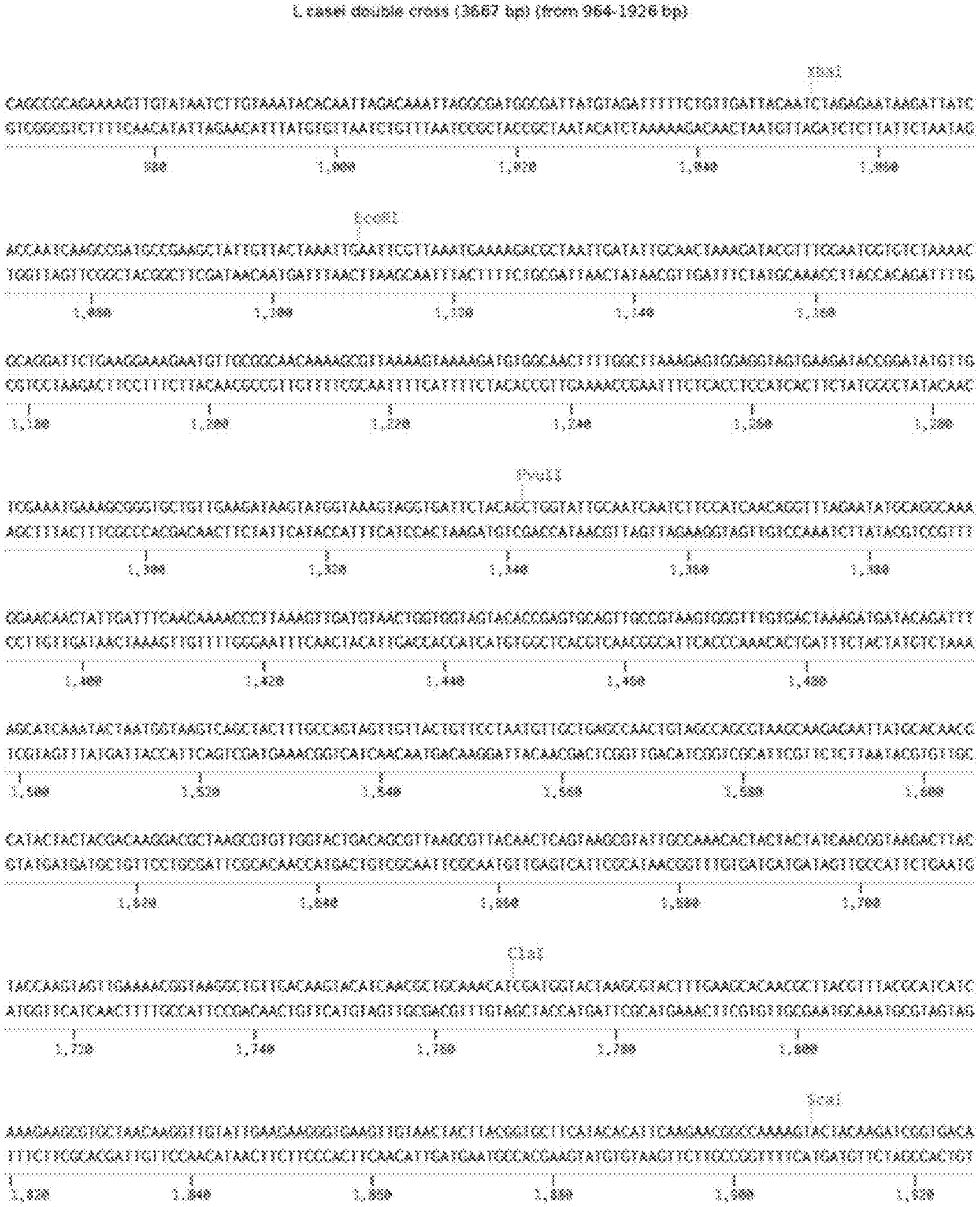
Figure 7:
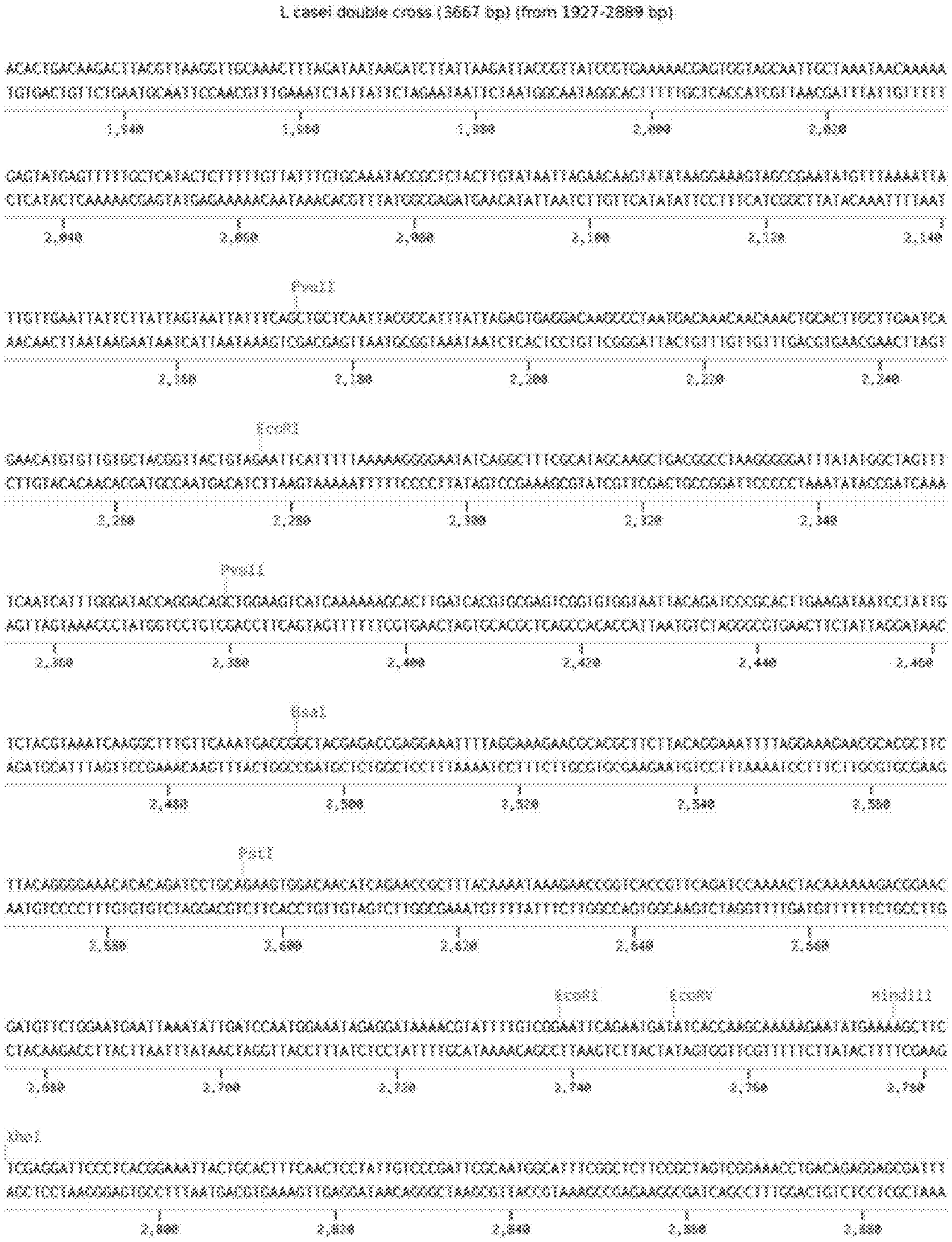
Figure 7:
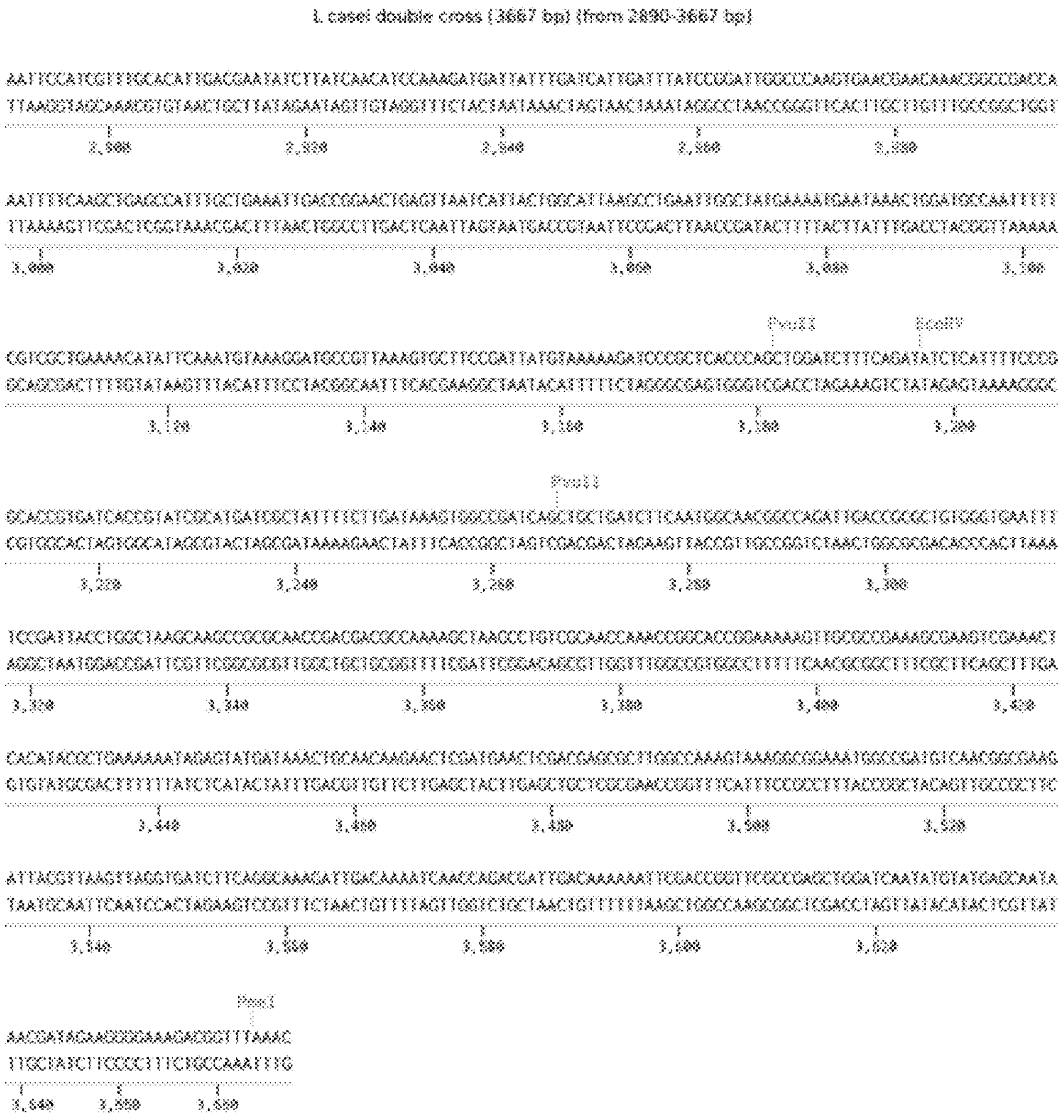
Figure 9:
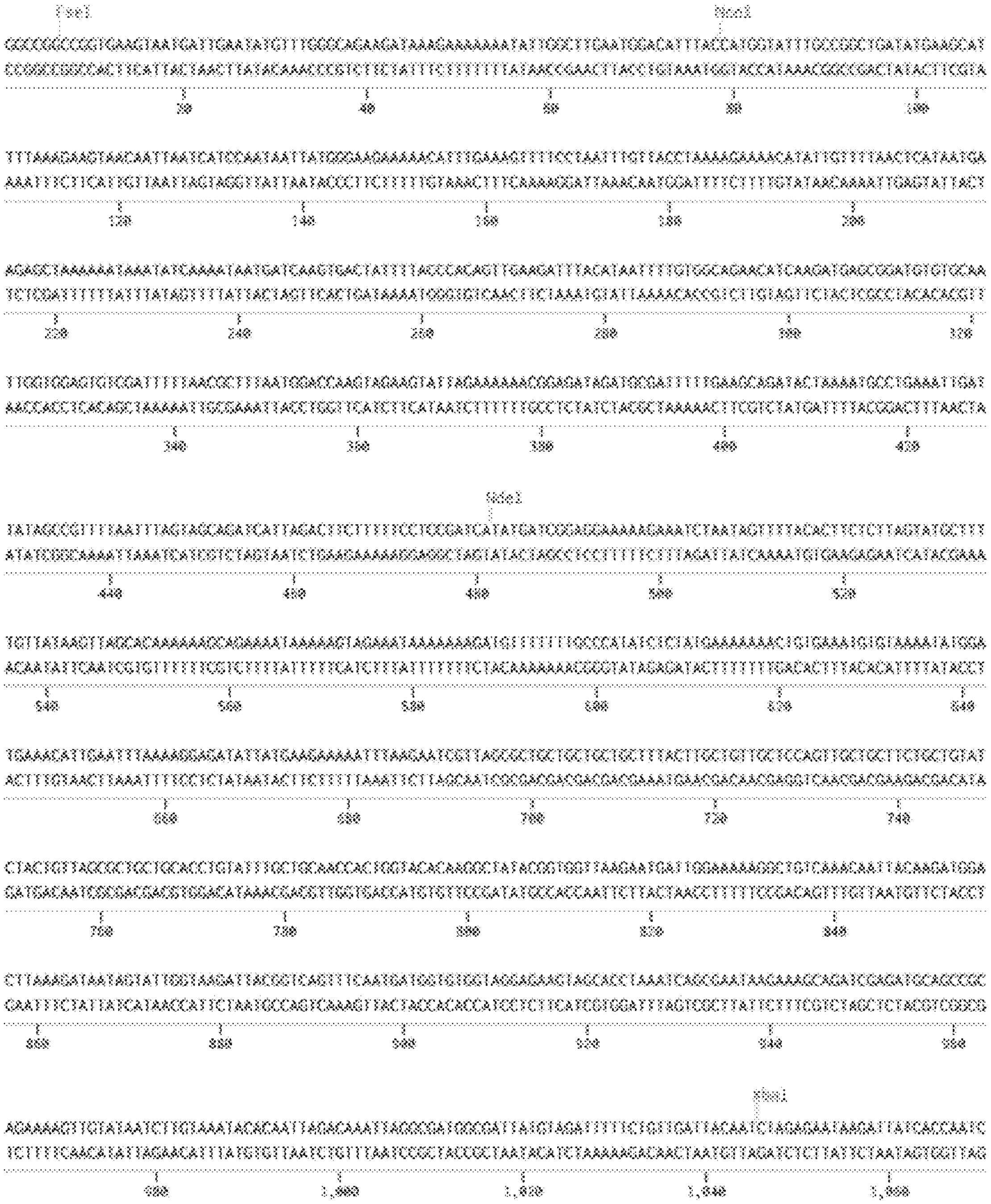
FIG. 9 provides a partial sequence of a plasmid used for double homologous recombination-based system for replacing a thyA gene in a bacterial chromosome with a SlpA chimeric protein encoding sequence and a YtvA fluorescent reporter encoding sequence in *Lactobacillus acidophilus*.
Figure 9:
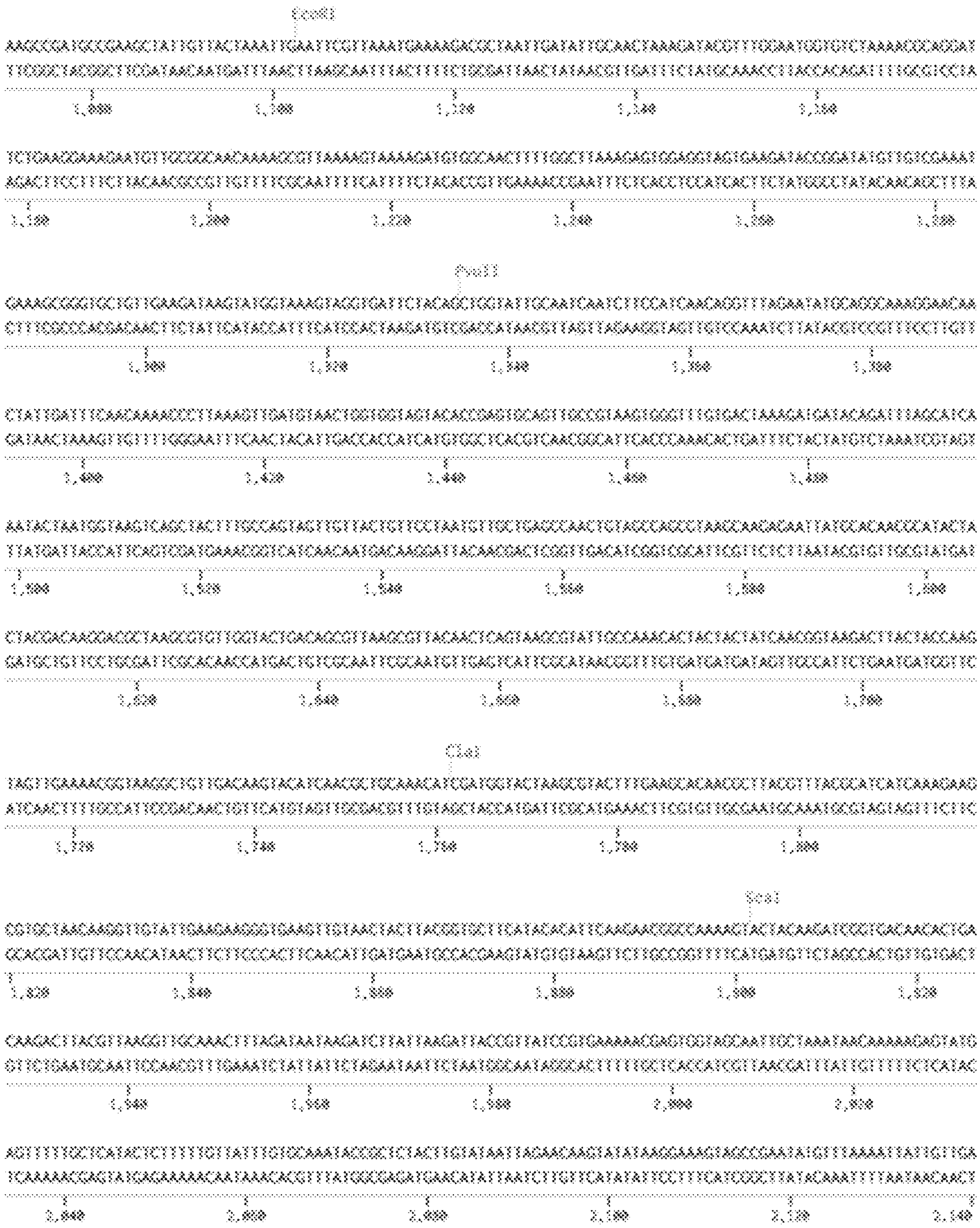
Figure 9:
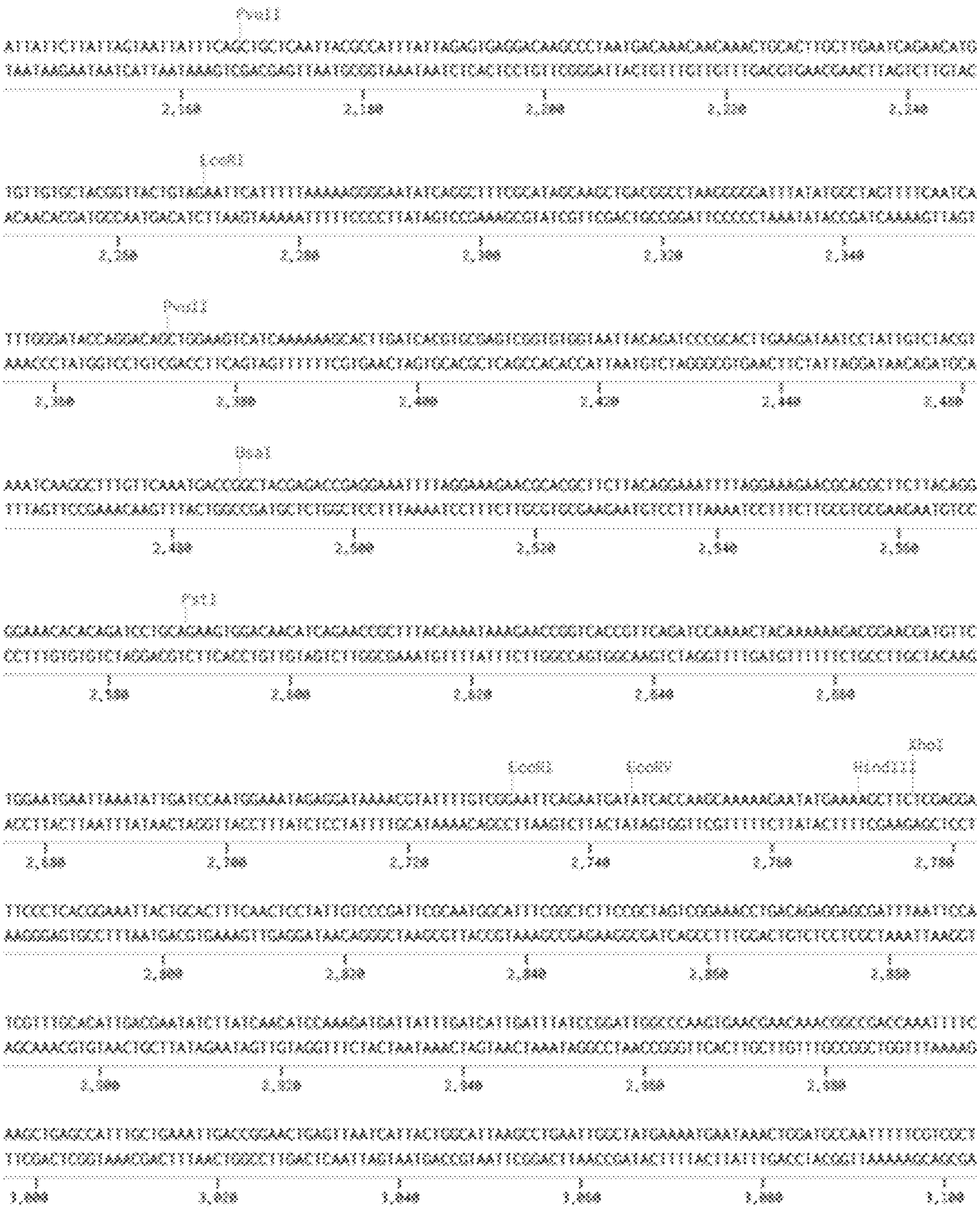
Figure 9:
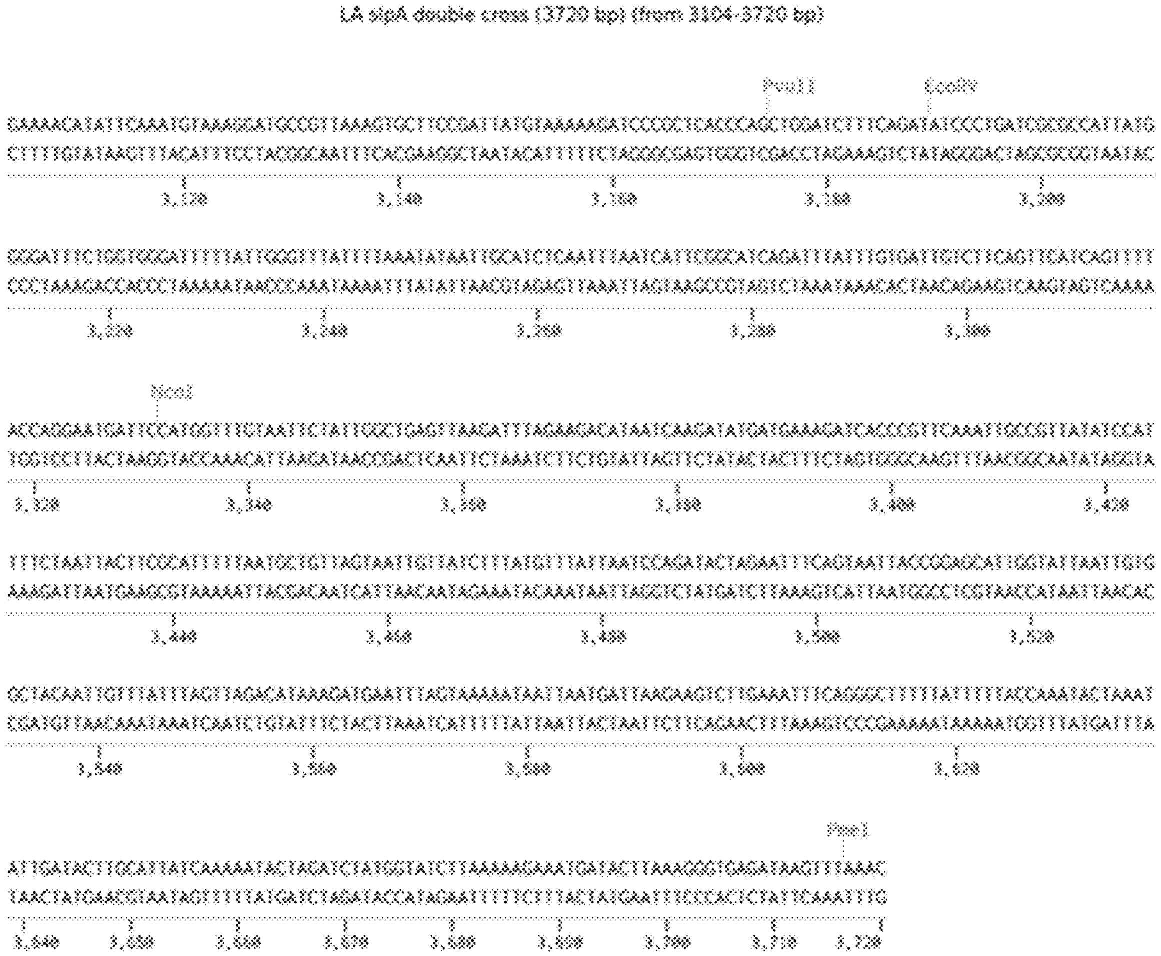

For the double homologous recombination, one vector is constructed for each species. Thus, a vector is constructed for specific use in *L. casei*, such that the vector includes a first nucleic acid sequence that is identical to a nucleic acid sequence of a fragment located at the 5' of the thyA gene in *L. casei* and a second nucleic acid sequence that is identical to a nucleic acid sequence of a fragment located at the 3' of the thyA gene in *L. casei*. Another vector is constructed for specific use in *L. acidophilus*, such that the vector includes a first nucleic acid sequence that is identical to a nucleic acid sequence of a first fragment located at the 5' of the thyA gene in *L. acidophilus* and a second nucleic acid sequence that is identical to a nucleic acid sequence of a second fragment located at the 3' of the thyA gene in *L. acidophilus*. The sequence of the vector for the specific use in *L. casei* for double recombination is shown in FIG. 7 and the sequence of the vector for the specific use in *L. acidophilus* for double homologous recombination is shown in FIG. 9.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An isolated polypeptide comprising, from the amino-terminus to the carboxy-terminus, a bacterial secretion signal, a *C. difficile* SlpA variable domain, and a *Lactobacillus* SlpA cell wall binding domain having the amino acid sequence SEQ ID NO:2.

2. The isolated polypeptide of claim 1, wherein the SlpA variable domain has the amino acid sequence SEQ ID NO: 1.

3. The isolated polypeptide of claim 1, wherein the bacterial secretion signal is a *Lactococcus* or *Lactobacillus* secretion signal.

4. The isolated polypeptide of claim 1, wherein the bacterial secretion signal has the amino acid sequence SEQ ID NO: 3.

5. The isolated polypeptide of claim 1, having the amino acid sequence SEQ ID NO: 4.

6. An isolated polypeptide comprising, from the amino-terminus to the carboxy-terminus, a bacterial secretion signal having the amino acid sequence SEQ ID NO: 3, a *C. difficile* SlpA variable domain, and a *Lactobacillus* SlpA cell wall binding domain.

7. The isolated polypeptide of claim 6, wherein the SlpA variable domain has the amino acid sequence SEQ ID NO: 1.

8. The isolated polypeptide of claim 6, wherein the SlpA cell wall binding domain is a *Lactobacillus acidophilus* or *Lactobacillus casei* SlpA cell wall binding domain.

9. The isolated polypeptide of claim 6, wherein the *Lactobacillus* SlpA cell wall binding domain has the amino acid sequence SEQ ID NO: 2.

10. The isolated polypeptide of claim 6, having the amino acid sequence SEQ ID NO: 4.

11. An isolated polypeptide comprising, from the amino-terminus to the carboxy-terminus, a bacterial secretion signal, a *C. difficile* SlpA variable domain, and a *Lactobacillus* SlpA cell wall binding domain, wherein the isolated polypeptide has the amino acid sequence SEQ ID NO: 4.

12. The isolated polypeptide of claim 3, wherein the bacterial secretion signal is a *Lactobacillus acidophilus* or *Lactobacillus casei* secretion signal.

* * * * *